(12) United States Patent
Thompson et al.

(10) Patent No.: US 11,208,386 B2
(45) Date of Patent: Dec. 28, 2021

(54) INHIBITORS OF PROTEIN ARGININE DEIMINASES (PADS) AND METHODS OF PREPARATION AND USE THEREOF

(71) Applicant: University of Massachusetts, Boston, MA (US)

(72) Inventors: Paul R. Thompson, Wellesley, MA (US); Aaron Muth, Brighton, MA (US); Venkataraman Subramanian, Worcester, MA (US)

(73) Assignee: University of Massachusetts, Boston, MA (US)

( * ) Notice: Subject to any disclaimer, the term of this patent is extended or adjusted under 35 U.S.C. 154(b) by 276 days.

(21) Appl. No.: 16/464,317

(22) PCT Filed: Nov. 27, 2017

(86) PCT No.: PCT/US2017/063324
§ 371 (c)(1),
(2) Date: May 28, 2019

(87) PCT Pub. No.: WO2018/102262
PCT Pub. Date: Jun. 7, 2018

(65) Prior Publication Data
US 2020/0339518 A1    Oct. 29, 2020

Related U.S. Application Data

(60) Provisional application No. 62/429,099, filed on Dec. 2, 2016.

(51) Int. Cl.
| C07D 235/14 | (2006.01) |
| C07D 403/12 | (2006.01) |
| C12Q 1/34 | (2006.01) |
| G01N 33/58 | (2006.01) |

(52) U.S. Cl.
CPC ......... *C07D 235/14* (2013.01); *C07D 403/12* (2013.01); *C12Q 1/34* (2013.01); *G01N 33/582* (2013.01); *G01N 2333/978* (2013.01)

(58) Field of Classification Search
CPC ...... C07D 235/14; C07D 403/12; C12Q 1/34; G01N 33/582
See application file for complete search history.

(56) References Cited

U.S. PATENT DOCUMENTS

| 2012/0277176 A1 | 11/2012 | Thompson et al. |
| 2015/0175600 A1 | 6/2015 | Atkinson et al. |

OTHER PUBLICATIONS

Knight, Ann Rheum Dis, Dec. 2015, vol. 74(12), 2199-2206. (Year: 2015).*
PCT/US17/63324, Int'l Search Report and Written Opinion of the ISA, dated Feb. 20, 2018.
Knight et al. "Peptidylarginine deiminase inhibition disrupts NET formation and protects against kidney, skin and vascular disease in lupus-prone MRL/lpr mice" Annals of the Rheumatic Diseases, vol. 74m, pp. 2199-2206, Dec. 2015.
Lewis et al. "Inhibition of PAD4 activity is sufficient to disrupt mouse and human NET formation" Nature Chemical Biology, vol. 11, pp. 189-191, Jan. 26, 2015.
Lavis et al. "Bright Building Blocks for Chemical Biology" ACS Chemical Biology, vol. 9, pp. 855-866, Feb. 28, 2014.

* cited by examiner

*Primary Examiner* — D Margaret M Seaman
(74) *Attorney, Agent, or Firm* — Milstein Zhang & Wu LLC

(57) ABSTRACT

The invention provides novel inhibitors or inactivators of protein arginine deiminases, pharmaceutical compositions and methods of use thereof. The invention also relates to molecular probes based on such compounds and methods of use thereof.

20 Claims, 5 Drawing Sheets

A TAMRA-N₃ visualization of probe labeled proteins.

B PAD2 pull down.

C Biotin pull down

A  TAMRA-N₃ visualization of probe labeled proteins.

B  PAD2 pull down.

C  Biotin pull down

A

B

INHIBITORS OF PROTEIN ARGININE DEIMINASES (PADS) AND METHODS OF PREPARATION AND USE THEREOF

PRIORITY CLAIMS AND RELATED APPLICATIONS

This application is the U.S. national phase of and claims priority to PCT/US2017/063324, filed Nov. 27, 2017, which claims the benefit of priority to U.S. Provisional Application Ser. No. 62/429,099, filed on Dec. 2, 2016, the entire content of each of which is incorporated herein by reference.

STATEMENT REGARDING FEDERALLY FUNDED RESEARCH OR DEVELOPMENT

This invention was made with government support under Grant No. GM079357 awarded by the National Institutes of Health. The Government has certain rights in the invention.

TECHNICAL FIELDS OF THE INVENTION

The invention generally relates to therapeutic compounds, pharmaceutical compositions and methods thereof. More particularly, the invention provides inhibitors or inactivators of protein arginine deiminases, pharmaceutical compositions and methods of preparation and use thereof. The invention also relates to molecular probes based on such compounds and methods of preparation and use thereof.

BACKGROUND OF THE INVENTION

A significant portion of the general population is affected by immune system disorders, which include abnormally low activity or over activity of the immune system. In cases of autoimmune diseases, the body's overly active immune system attacks and damages its own tissues. In cases of an overly inactive immune system, the body's ability to fight invaders decreases due to immune deficiency, leaving the patient vulnerable to infections. Currently, treatment for autoimmune diseases focuses on relieving symptoms because there is no curative therapy.

Immune system disorders, such as rheumatoid arthritis (RA), multiple sclerosis, lupus, and ulcerative colitis, are placing an increasing burden on society, impairing the health and lives of those affected. Although medications have been developed to treat some of these diseases and conditions, the available treatments are often limited in terms of clinical effectiveness and at the same time have undesirable side effects.

Protein arginine deiminases (PADs) are a unique family of enzymes that catalyzes a form of post-translational modification called arginine deimination or citrullination: the hydrolysis of peptidyl-arginine to form peptidyl-citrulline on histones, fibrinogen, and other biologically relevant proteins. The post-translational modification of histones has significant effects on overall chromatin function.

The PAD reaction involves the hydrolysis of the guanidinium group of arginine to generate citrullinated proteins. This reaction is a calcium-dependent process wherein calcium binding triggers a conformational change that moves a nucleophilic cysteine residue into the active site, resulting in a >10,000-fold increase in PAD activity. Overexpression and/or increased PAD activity is observed in several diseases, including rheumatoid arthritis, Alzheimer's disease, multiple sclerosis, lupus, Parkinson's disease, and cancer. (Liu, et al. 2011 *PLoS One* 6, e21314; Kearney, et al. 2005 *Biochemistry* 44, 10570-10582.)

There are five PAD isozymes (PADs 1-4 and 6) with unique cellular and tissue distribution patterns, where only PADs 1-4 have been isolated in their catalytically active form. The PADs are uniquely distributed both within the cell and throughout the body. Specifically, all the PADs can be found in the cellular cytoplasm while only PADs 2, 3 and 4 are expressed in the nucleus. (Jones, et al. 2009 *Curr Opin Drug Discov Devel* 12, 616-627. Vossenaar, et al. 2003 *Bioessays* 25, 1106-1118; Stone, et al. 2005 *Biochemistry* 44, 13744-13752; Fuhrmann, et al. 2015 *Chem Rev* 115, 5413-5461; Nakashima, et al. 2002 *J Biol Chem* 277, 49562-49568; Cherrington, et al. 2010 *PLoS One* 5, el 1768; Jang, et al. 2011 *J Neuropathol Exp Neurol* 70, 116-124; Li, et al. 2016 *PLoS One* 11, e0147503.)

There is an urgent and growing need for novel therapeutics and treatment methods that provide improved clinical effectiveness with reduced side effects, in particular through safe and effective inhibition or inactivation of PADs.

SUMMARY OF THE INVENTION

The invention provides novel inhibitors or inactivators of PADs, pharmaceutical compositions and methods of preparation and use thereof. The compounds and pharmaceutical compositions of the invention may be used to treat immune system disorders and inflammatory diseases and conditions (e.g., rheumatoid arthritis, lupus).

The invention also provides novel molecular probes (e.g., imaging probes) for PADs based on the inhibitors or inactivators of PADs disclosed herein in conjugation with detectable labels such as fluorescent dyes, and methods of preparation and use thereof. The molecular imaging probes of the invention may be used to screen or identify compounds for PAD inhibition or inactivation.

In one aspect, the invention generally relates to a compound having the structural formula (I),

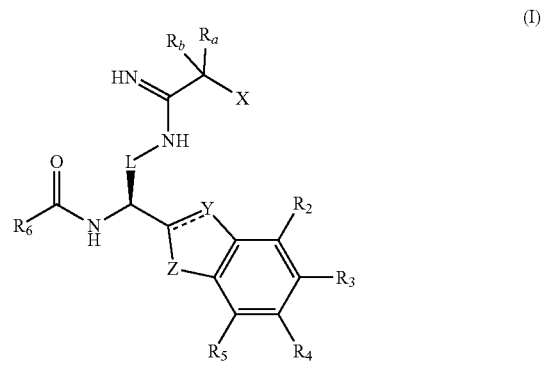

wherein
each of $R_a$ and $R_b$ is independently selected from the group consisting of H, D and F;
L is a bivalent hydrocarbyl linker, optionally with one or more carbon atoms replaced by a heteroatom selected from the group consisting of O, S and N;
X is a halogen atom;
Y is N, O or S; provided that when Y is S or O, its bonding to the adjacent carbons are single bonds;
Z is N—$R_1$, O or S;
$R_1$ is selected from the group consisting of: H, a $C_{1-6}$ alkyl, OH, a $C_{1-3}$ alkoxy, $CF_3$, $COCH_3$, and $COCF_3$ groups;

each of $R_2$, $R_3$, $R_4$ and $R_5$ is independently selected from the group consisting of: H, hydroxyl, halogen atom, $C_{1-6}$ alkyl, $C_{1-6}$ alkoxy, alkynyl, $CF_2R_c$, and $OCF_2R_c$ groups, where $R_c$ is H, F or alkyl; and $R_6$ is a group comprising a cyclic alkyl or aryl moiety, or a pharmaceutically acceptable form thereof.

In another aspect, the invention generally relates to a pharmaceutical composition comprising a compound having the structural formula of (I):

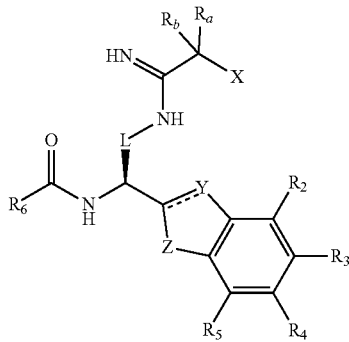

(I)

wherein, each of $R_a$ and $R_b$ is independently selected from the group consisting of H, D and F;

L is a bivalent hydrocarbyl linker, optionally with one or more carbon atoms replaced by a heteroatom selected from the group consisting of O, S and N;

X is a halogen atom;

Y is N, O or S; provided that when Y is S or O, its bonding to the adjacent carbons are single bonds;

Z is N—$R_1$, O or S;

$R_1$ is selected from the group consisting of: H, a $C_{1-6}$ alkyl, OH, a $C_{1-3}$ alkoxy, $CF_3$, $COCH_3$, and $COCF_3$ groups;

each of $R_2$, $R_3$, $R_4$ and $R_5$ is independently selected from the group consisting of: H, hydroxyl, halogen atom, $C_{1-6}$ alkyl, $C_{1-6}$ alkoxy, alkynyl, $CF_2R_c$, and $OCF_2R_c$ groups, where $R_c$ is H, F or alkyl; and $R_6$ is a group comprising a cyclic alkyl or aryl moiety, or a pharmaceutically acceptable form thereof, effective to treat, prevent, or reduce one or more diseases or disorders, in a mammal, including a human, and a pharmaceutically acceptable excipient, carrier, or diluent.

In yet another aspect, the invention generally relates to a unit dosage form comprising a pharmaceutical composition disclosed herein.

In yet another aspect, the invention generally relates to a method for treating, reducing, or preventing a disease or disorder. The method includes administering to a subject in need thereof a pharmaceutical composition comprising a compound having the structural formula of (I):

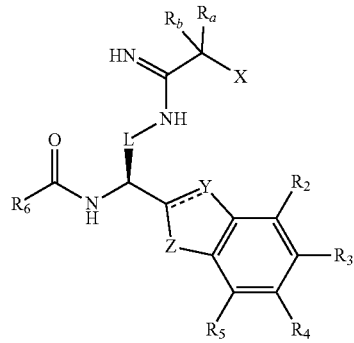

(I)

wherein, each of $R_a$ and $R_b$ is independently selected from the group consisting of H, D and F;

L is a bivalent hydrocarbyl linker, optionally with one or more carbon atoms replaced by a heteroatom selected from the group consisting of O, S and N;

X is a halogen atom;

Y is N, O or S; provided that when Y is S or O, its bonding to the adjacent carbons are single bonds;

Z is N—$R_1$, O or S;

$R_1$ is selected from the group consisting of: H, a $C_{1-6}$ alkyl, OH, a $C_{1-3}$ alkoxy, $CF_3$, $COCH_3$, and $COCF_3$ groups;

each of $R_2$, $R_3$, $R_4$ and $R_5$ is independently selected from the group consisting of: H, hydroxyl, halogen atom, $C_{1-6}$ alkyl, $C_{1-6}$ alkoxy, alkynyl, $CF_2R_c$, and $OCF_2R_c$ groups, where $R_c$ is H, F or alkyl; and $R_6$ is a group comprising a cyclic alkyl or aryl moiety, or a pharmaceutically acceptable form thereof, and a pharmaceutically acceptable excipient, carrier, or diluent, effective to treat, prevent, or reduce one or more diseases or disorders, in a mammal, including a human.

In yet another aspect, the invention generally relates to a method for inhibiting or inactivating a protein arginine deiminase, comprising administering to a subject in need thereof a pharmaceutical composition comprising a compound having the structural formula of (I):

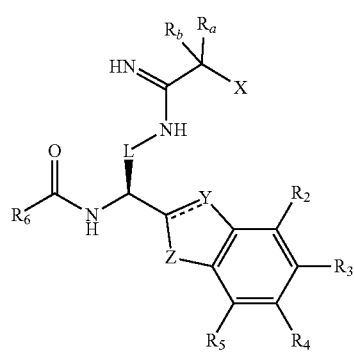

(I)

wherein, each of $R_a$ and $R_b$ is independently selected from the group consisting of H, D and F;

L is a bivalent hydrocarbyl linker, optionally with one or more carbon atoms replaced by a heteroatom selected from the group consisting of O, S and N;

X is a halogen atom;

Y is N, O or S; provided that when Y is S or O, its bonding to the adjacent carbons are single bonds;

Z is N—$R_1$, O or S;

$R_1$ is selected from the group consisting of: H, a $C_{1-6}$ alkyl, OH, a $C_{1-3}$ alkoxy, $CF_3$, $COCH_3$, and $COCF_3$ groups;

each of $R_2$, $R_3$, $R_4$ and $R_5$ is independently selected from the group consisting of: H, hydroxyl, halogen atom, $C_{1-6}$ alkyl, $C_{1-6}$ alkoxy, alkynyl, $CF_2R_c$ and $OCF_2R_c$ groups, where $R_c$ is H, F or alkyl; and $R_6$ is a group comprising a cyclic alkyl or aryl moiety, or a pharmaceutically acceptable form thereof, and a pharmaceutically acceptable excipient, carrier, or diluent, effective to inhibit or inactivate a biological function of a protein arginine deiminase, in a mammal, including a human.

In yet another aspect, the invention generally relates to a molecular imaging probe having the structural formula:

$$A_F\text{-}L_F\text{-}W \qquad (II)$$

wherein $A_F$ is a group comprising an optically detectable moiety;

$L_F$ is a linking group; and

W is group comprising a benzimidazole moiety, or a derivative or analog thereof, capable of inhibiting or inactivating a biological function of a protein arginine deiminase.

In yet another aspect, the invention generally relates to a method for identifying a protein arginine deiminase inhibitor or inactivator. The method includes: performing a competitive assay wherein a test compound competes with a molecular imaging probe disclosed herein to bind to a protein arginine deiminase; and measuring fluorescence to determine an amount of fluorescent protein arginine deiminase present in the test assay.

DEFINITIONS

Figure 1:
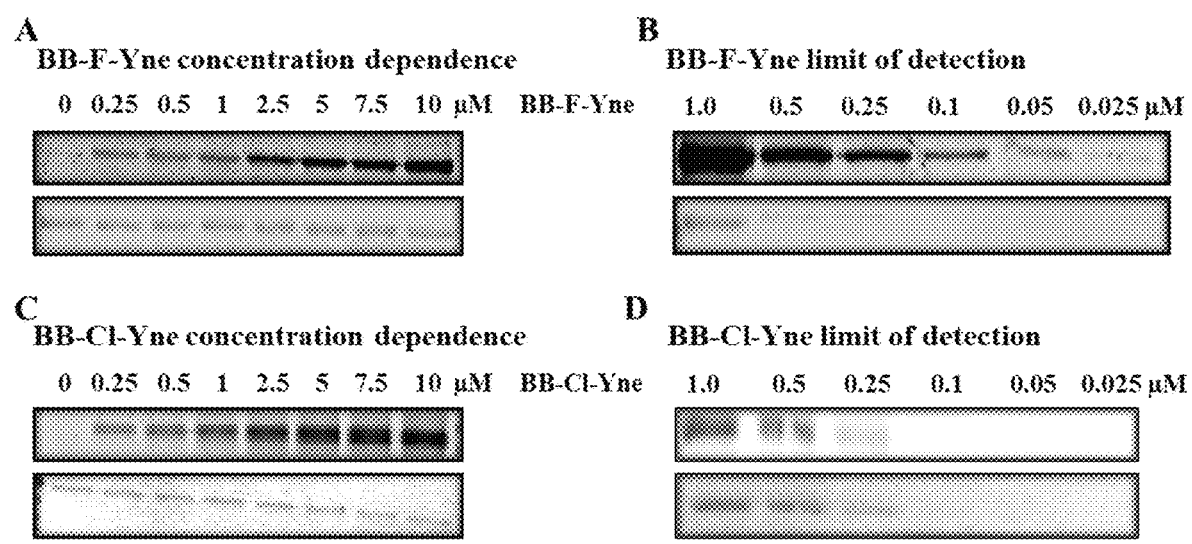
FIG. 1. (A) Concentration dependent labeling of recombinant PAD2 with BB-F-Yne (5u). PAD2 was treated with increasing concentrations of BB-F-Yne (5u) and then "Clicked" with TAMRA-$N_3$. (B) The limit of detection (LOD) of BB-F-Yne (5u) for PAD2. Decreasing concentrations of PAD2 treated with BB-F-Yne (5u) and "Clicked" with TAMRA-$N_3$. The LOD was found to be 375 fmol. (C) Concentration dependent labeling of recombinant PAD2 with BB-C-Yne (5v). PAD2 was treated with increasing concentrations of BB-Cl-Yne (5) and then "Clicked" with TAMRA-$N_3$. (D) The LOD of BB-Cl-Yne (5v) for PAD2. Decreasing concentrations of PAD2 were treated with BB-Cl-Yne (5v) and "Clicked" with TAMRA-$N_3$.

Unless defined otherwise, all technical and scientific terms used herein have the same meaning as commonly understood by one of ordinary skill in the art to which this invention belongs. General principles of organic chemistry, as well as specific functional moieties and reactivity, are described in "Organic Chemistry", Thomas Sorrell, University Science Books, Sausalito: 2006.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

As used herein, "administration" of a disclosed compound encompasses the delivery to a subject of a compound as described herein, or a prodrug or other pharmaceutically acceptable derivative thereof, using any suitable formulation or route of administration, as discussed herein.

As used herein, the terms "effective amount" or "therapeutically effective amount" refer to that amount of a compound or pharmaceutical composition described herein that is sufficient to effect the intended application including, but not limited to, disease treatment, as illustrated below.

In some embodiments, the amount is that effective for stop the progression or effect reduction of an inflammatory disease or disorder. In some embodiments, the amount is that effective for stop the progression or effect reduction of an immune system disorders. In some embodiments, the amount is that effective to stop the progression or effect reduction of an autoimmune disease or disorder. In some embodiments, the amount is that effective for stop the progression or effect reduction of a cardiovascular disease or disorder. In some embodiments, the amount is that effective for detectable killing or inhibition of the growth or spread of cancer cells; the size or number of tumors; or other measure of the level, stage, progression or severity of the cancer.

The therapeutically effective amount can vary depending upon the intended application, or the subject and disease condition being treated, e.g., the desired biological endpoint, the pharmacokinetics of the compound, the disease being treated, the mode of administration, and the weight and age of the patient, which can readily be determined by one of ordinary skill in the art. The term also applies to a dose that will induce a particular response in target cells, e.g., reduction of cell migration. The specific dose will vary depending on, for example, the particular compounds chosen, the species of subject and their age/existing health conditions or risk for health conditions, the dosing regimen to be followed, the severity of the disease, whether it is administered in combination with other agents, timing of administration, the tissue to which it is administered, and the physical delivery system in which it is carried.

As used herein, the terms "treatment" or "treating" a disease or disorder refers to a method of reducing, delaying or ameliorating such a condition before or after it has occurred. Treatment may be directed at one or more effects or symptoms of a disease and/or the underlying pathology. Treatment is aimed to obtain beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compounds and/or compositions can be administered to a patient at risk of developing a particular disease, or to a patient reporting one or more of the physiological symptoms of a disease, even though a diagnosis of this disease may not have been made. The treatment can be any reduction and can be, but is not limited to, the complete ablation of the disease or the symptoms of the disease. As compared with an equivalent untreated control, such reduction or degree of prevention is at least 5%, 10%, 20%, 40%, 50%, 60%, 80%, 90%, 95%, or 100% as measured by any standard technique.

As used herein, the term "therapeutic effect" refers to a therapeutic benefit and/or a prophylactic benefit as described herein. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, a "pharmaceutically acceptable form" of a disclosed compound includes, but is not limited to, pharmaceutically acceptable salts, esters, hydrates, solvates, isomers, prodrugs, and isotopically labeled derivatives of disclosed compounds. In one embodiment, a "pharmaceutically acceptable form" includes, but is not limited to, pharmaceutically acceptable salts, esters, isomers, prodrugs and isotopically labeled derivatives of disclosed compounds. In some embodiments, a "pharmaceutically acceptable form" includes, but is not limited to, pharmaceutically acceptable salts, esters, stereoisomers, prodrugs and isotopically labeled derivatives of disclosed compounds.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchioric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, lactic acid, trifluoracetic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The salts can be prepared in situ during the isolation and purification of the disclosed compounds, or separately, such as by reacting the free base or free acid of a parent compound with a suitable base or acid, respectively. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines, including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt can be chosen from ammonium, potassium, sodium, calcium, and magnesium salts.

In certain embodiments, the pharmaceutically acceptable form is a pharmaceutically acceptable ester. As used herein, the term "pharmaceutically acceptable ester" refers to esters that hydrolyze in vivo and include those that break down readily in the human body to leave the parent compound or a salt thereof. Such esters can act as a prodrug as defined herein. Pharmaceutically acceptable esters include, but are not limited to, alkyl, alkenyl, alkynyl, aryl, aralkyl, and cycloalkyl esters of acidic groups, including, but not limited to, carboxylic acids, phosphoric acids, phosphinic acids, sulfinic acids, sulfonic acids and boronic acids. Examples of esters include formates, acetates, propionates, butyrates, acrylates and ethylsuccinates. The esters can be formed with a hydroxy or carboxylic acid group of the parent compound.

As used herein, the term "pharmaceutically acceptable enol ethers" include, but are not limited to, derivatives of formula —C=C(OR) where R can be selected from alkyl, alkenyl, alkynyl, aryl, aralkyl and cycloalkyl. Pharmaceutically acceptable enol esters include, but are not limited to, derivatives of formula —C=C(OC(O)R) where R can be selected from hydrogen, alkyl, alkenyl, alkynyl, aryl, aralkyl and cycloalkyl.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or 1 to about 2, about 3 or about 4, solvent or water molecules. It will be understood that the term "compound" as used herein encompasses the compound and solvates of the compound, as well as mixtures thereof.

In certain embodiments, the pharmaceutically acceptable form is a prodrug. As used herein, the term "prodrug" (or "pro-drug") refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs can increase the bioavailability of the compound when administered to a subject (e.g., by permitting enhanced absorption into the blood following oral administration) or which enhance delivery to a biological compartment of interest (e.g., the brain or lymphatic system) relative to the parent compound. Exemplary prodrugs include derivatives of a disclosed compound with enhanced aqueous solubility or active transport through the gut membrane, relative to the parent compound.

The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it can enhance absorption from the digestive tract, or it can enhance drug stability for long-term storage.

As used herein, the term "pharmaceutically acceptable" excipient, carrier, or diluent refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

Compounds of the present invention are, subsequent to their preparation, preferably isolated and purified to obtain a composition containing an amount by weight equal to or greater than 95% ("substantially pure"), which is then used or formulated as described herein. In certain embodiments, the compounds of the present invention are more than 99% pure.

Solvates and polymorphs of the compounds of the invention are also contemplated herein. Solvates of the compounds of the present invention include, for example, hydrates.

Definitions of specific functional groups and chemical terms are described in more detail below. When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, the term "alkyl" refers to a straight or branched hydrocarbon chain radical consisting solely of carbon and hydrogen atoms, containing no unsaturation, having from one to ten carbon atoms (e.g., $C_{1-10}$ alkyl). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, etc., up to and including 10 carbon atoms, although the present definition also covers the occurrence of the term "alkyl" where no numerical range is designated. In some embodiments, "alkyl" can be a $C_{1-6}$ alkyl group. In some embodiments, alkyl groups have 1 to 10, 1 to 8, 1 to 6, or 1 to 3 carbon atoms. Representative saturated straight chain alkyls include, but are not limited to, -methyl, -ethyl, -n-propyl, -n-butyl, -n-pentyl, and -n-hexyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group is optionally substituted by one or more of substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —$OR^a$, —$SR^a$, —OC(O)—$R^a$, —$OR^a$, —$SR^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. In a non-limiting embodiment, a substituted alkyl can be selected from fluoromethyl, difluoromethyl, trifluoromethyl, 2-fluoroethyl, 3-fluoropropyl, hydroxymethyl, 2-hydroxyethyl, 3-hydroxypropyl, benzyl, and phenethyl.

As used herein, the term "alkoxy" refers to the group —O-alkyl, including from 1 to 10 carbon atoms ($C_{1-10}$) of a straight, branched, saturated cyclic configuration and combinations thereof, attached to the parent molecular structure through an oxygen. Examples include methoxy, ethoxy, propoxy, isopropoxy, butoxy, t-butoxy, pentoxy, cyclopropyloxy, cyclohexyloxy and the like. "Lower alkoxy" refers to alkoxy groups containing one to six carbons. In some embodiments, $C_{1-3}$ alkoxy is an alkoxy group that encompasses both straight and branched chain alkyls of from 1 to 3 carbon atoms. Unless stated otherwise in the specification, an alkoxy group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —$OR^a$, —$SR^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the terms "aromatic" or "aryl" refer to a radical with 6 to 14 ring atoms (e.g., $C_{6-14}$ aromatic or $C_{6-14}$ aryl) which has at least one ring having a conjugated pi electron system which is carbocyclic (e.g., phenyl, fluorenyl, and naphthyl). In some embodiments, the aryl is a $C_{6-10}$ aryl group. For example, bivalent radicals formed from substituted benzene derivatives and having the free valences at ring atoms are named as substituted phenylene radicals. In other embodiments, bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 14 aryl" refers to each integer in the given range; e.g., "6 to 14 ring atoms" means that the aryl group can consist of 6 ring atoms, 7 ring atoms, etc., up to and including 14 ring atoms. The term includes monocyclic or fused-ring polycyclic (i.e., rings which share adjacent pairs of ring atoms) groups. Polycyclic aryl groups include bicycles, tricycles, tetracycles, and the like. In a multi-ring group, only one ring is required to be aromatic, so groups such as indanyl are encompassed by the aryl definition. Non-limiting examples of aryl groups include phenyl, phenalenyl, naphthalenyl, tetrahydronaphthyl, phenanthrenyl, anthracenyl, fluorenyl, indolyl, indanyl, and the like. Unless stated otherwise in the specification, an aryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —$OR^a$, —$SR^a$, —OC(O)—$R^a$, —N($R^a$)$_2$, —C(O)$R_a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the terms "cycloalkyl" and "carbocyclyl" each refers to a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 13 ring atoms (i.e., $C_{3-13}$ cycloalkyl). Whenever it appears herein, a numerical range such as "3 to 10" refers to each integer in the given range; e.g., "3 to 13 carbon atoms" means that the cycloalkyl group can consist of 3 carbon atoms, 4 carbon atoms, 5 carbon atoms, etc., up to and including 13 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. Polycyclic aryl groups include bicycles, tricycles, tetracycles, and the like. In some embodiments, "cycloalkyl" can be a $C_{3-8}$ cycloalkyl radical. In some embodiments, "cycloalkyl" can be a $C_{3-5}$ cycloalkyl radical. Illustrative examples of cycloalkyl groups include, but are not limited to the following moieties: $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$) and the like. Examples of $C_{3-7}$ carbocyclyl groups include norbornyl ($C_7$). Examples of $C_{3-8}$ carbocyclyl groups include the aforementioned $C_{3-7}$ carbocyclyl groups as well as cycloheptyl ($C_7$), cycloheptadienyl ($C_7$), cycloheptatrienyl ($C_7$), cyclooctyl ($C_8$), bicyclo[2.2.1] heptanyl, bicyclo[2.2.2]octanyl, and the like. Examples of $C_{3-13}$ carbocyclyl groups include the aforementioned $C_{3-8}$ carbocyclyl groups as well as octahydro-1H indenyl, decahydronaphthalenyl, spiro[4.5]decanyl and the like. Unless stated otherwise in the specification, a cycloalkyl group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "cycloalkenyl" and "cycloalkynyl" mirror the above description of "cycloalkyl" wherein the prefix "alk" is replaced with "alken" or "alkyn" respectively, and the parent "alkenyl" or "alkynyl" terms are as described herein. For example, a cycloalkenyl group can have 3 to 13 ring atoms, such as 5 to 8 ring atoms. In some embodiments, a cycloalkynyl group can have 5 to 13 ring atoms.

As used herein, the term "halide", "halo", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine, such as, but not limited to, trifluoromethyl, difluoromethyl, 2,2,2-trifluoroethyl, 1-fluoromethyl-2-fluoroethyl, and the like. Each of the alkyl, alkenyl, alkynyl and alkoxy groups are as defined herein and can be optionally further substituted as defined herein.

As used herein, the term "heteroalkyl" refers to an alkyl radical, which have one or more skeletal chain atoms selected from an atom other than carbon, e.g., oxygen, nitrogen, sulfur, phosphorus or combinations thereof. A numerical range can be given, e.g., $C_{1-4}$ heteroalkyl which refers to the chain length in total, which in this example is 4 atoms long. For example, a —CH$_2$OCH$_2$CH$_3$ radical is referred to as a "$C_4$" heteroalkyl, which includes the heteroatom center in the atom chain length description. Connection to the parent molecular structure can be through either a heteroatom or a carbon in the heteroalkyl chain. For example, an N-containing heteroalkyl moiety refers to a group in which at least one of the skeletal atoms is a nitrogen atom. One or more heteroatom(s) in the heteroalkyl radical can be optionally oxidized. One or more nitrogen atoms, if present, can also be optionally quaternized. For example, heteroalkyl also includes skeletal chains substituted with one or more nitrogen oxide (—O—) substituents. Exemplary heteroalkyl groups include, without limitation, ethers such as methoxyethanyl (—CH$_2$CH$_2$OCH$_3$), ethoxymethanyl (—CH$_2$OCH$_2$CH$_3$), (methoxymethoxy)ethanyl (—CH$_2$CH$_2$OCH$_2$OCH$_3$), (methoxymethoxy) methanyl (—CH$_2$OCH$_2$OCH$_3$) and (methoxyethoxy)methanyl (—CH$_2$OCH$_2$CH$_2$OCH$_3$) and the like; amines such as (—CH$_2$CH$_2$NHCH$_3$, —CH$_2$CH$_2$N(CH$_3$)$_2$, —CH$_2$NHCH$_2$CH$_3$, —CH$_2$N(CH$_2$CH$_3$)(CH$_3$)) and the like.

As used herein, the term "heteroaryl" or, alternatively, "heteroaromatic" refers to a refers to a radical of a 5-18 membered monocyclic or polycyclic (e.g., bicyclic, tricyclic, tetracyclic and the like) aromatic ring system (e.g., having 6, 10 or 14×electrons shared in a cyclic array) having ring carbon atoms and 1-6 ring heteroatoms provided in the aromatic ring system, wherein each heteroatom is independently selected from nitrogen, oxygen, phosphorous and sulfur ("5-18 membered heteroaryl"). Heteroaryl polycyclic ring systems can include one or more heteroatoms in one or both rings. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. In some instances, a heteroaryl can have 5 to 14 ring atoms. In some embodiments, the heteroaryl has, for example, bivalent radicals derived from univalent heteroaryl radicals whose names end in "-yl" by removal of one hydrogen atom from the atom with the free valence are named by adding "-ene" to the name of the corresponding univalent radical, e.g., a pyridyl group with two points of attachment is a pyridylene.

For example, an N-containing "heteroaromatic" or "heteroaryl" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocycyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4] oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzopyranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno [2,3-d]pyrimidinyl, 5,6-dihydrobenzo[h]quinazolinyl, 5,6-dihydrobenzo[h]cinnolinyl, 6,7-dihydro-5H benzo[6,7]cyclohepta[1,2-c]pyridazinyl, dibenzofuranyl, dibenzothiophenyl, furanyl, furazanyl, furanonyl, furo [3,2-c]pyridinyl, 5,6,7,8,9,10-hexahydrocyclootca[d] pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo [4,5] thieno [2,3-d]pyrimidinyl, 6,7,8,9-tetrahydro-5H-cyclohepta[4,5]thieno [2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno [2,3-c]pridinyl, and thiophenyl (i.e., thienyl). Unless stated otherwise in the specification, a heteroaryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R_a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the term "antibody" refers to molecules that are capable of binding an epitope or antigenic determinant. The term is meant to include whole antibodies and antigen-binding fragments thereof, including single-chain antibodies. The antibodies can be from any animal origin. Preferably, the antibodies are mammalian, e.g., human, murine, rabbit, goat, guinea pig, camel, horse and the like, or other suitable animals. Antibodies may recognize polypeptide or polynucleotide antigens. The term includes active fragments, including for example, an antigen binding fragment of an immunoglobulin, a variable and/or constant region of a heavy chain, a variable and/or constant region of a light chain, a complementarity determining region (cdr), and a framework region. The terms include polyclonal and monoclonal antibody preparations, as well as preparations including hybrid antibodies, altered antibodies, chimeric antibodies, hybrid antibody molecules, F(ab)$_2$ and F(ab) fragments; Fv molecules (for example, noncovalent heterodimers), dimeric and trimeric antibody fragment constructs; minibodies, humanized antibody molecules, and any functional fragments obtained from such molecules, wherein such fragments retain specific binding.

As used herein, the term "epitope" refers to basic element or smallest unit of recognition by an individual antibody or T-cell receptor, and thus the particular domain, region or molecular structure to which said antibody or T-cell receptor binds. An antigen may consist of numerous epitopes while a hapten, typically, may possess few epitopes.

As used herein, the term "immune system" diseases or conditions refers to a group of conditions characterized by a dysfunctioning immune system. These disorders can be characterized in several different ways: by the component(s) of the immune system affected, by whether the immune system is overactive or underactive, or by whether the condition is congenital or acquired. Autoimmune diseases or conditions are among immune system diseases or conditions.

As used herein, the term "inflammatory" diseases or conditions refers to a group of conditions including, rheumatoid arthritis, osteoarthritis, juvenile idiopathic arthritis, psoriasis, allergic airway disease (e.g., asthma, rhinitis), inflammatory bowel diseases (e.g., Crohn's disease, colitis), endotoxin-driven disease states (e.g., complications after bypass surgery or chronic endotoxin states contributing to e.g. chronic cardiac failure), and related diseases involving cartilage, such as that of the joints.

As used herein, the term "autoimmune" diseases or conditions refers to conditions arising from an abnormal immune response to a normal body part. Examples of include, but not limited to rheumatoid arthritis, lupus, Alzheimer's disease, multiple sclerosis, Parkinson's disease, inflammatory bowel disease, and psoriasis.

As used herein, the term "cancer" refers to or describes the physiological condition in mammals that is typically characterized by unregulated cell growth. Examples of cancer include but are not limited to, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer.

As used herein, the term "tumor" refers to any malignant or neoplastic cell.

As used herein, the terms "polypeptide" and "protein" are used interchangeably to refer to a polymer of amino acid residues, and are not limited to a minimum length. Thus, peptides, oligopeptides, dimers, multimers, and the like, are included within the definition. Both full-length proteins and fragments thereof are encompassed by the definition. The terms also include post-expression modifications of the polypeptide, for example, glycosylation, acetylation, phosphorylation, and the like. Furthermore, a "polypeptide" may refer to a protein which includes modifications, such as deletions, additions, and substitutions (generally conservative in nature), to the native sequence, as long as the protein maintains the desired activity. These modifications may be deliberate or may be accidental.

As used herein, the term "sample" refers to a sample from a human, animal, or to a research sample, e.g., a cell, tissue, organ, fluid, gas, aerosol, slurry, colloid, or coagulated material. The "sample" may be tested in vivo, e.g., without removal from the human or animal, or it may be tested in vitro. The sample may be tested after processing, e.g., by histological methods. "Sample" also refers, e.g., to a cell comprising a fluid or tissue sample or a cell separated from a fluid or tissue sample. "Sample" may also refer to a cell, tissue, organ, or fluid that is freshly taken from a human or animal, or to a cell, tissue, organ, or fluid that is processed or stored.

As used herein, the term an "isolated" or "substantially isolated" molecule (such as a polypeptide or polynucleotide) is one that has been manipulated to exist in a higher concentration than in nature or has been removed from its native environment. For example, a subject antibody is isolated, purified, substantially isolated, or substantially purified when at least 10%, or 20%, or 40%, or 50%, or 70%, or 90% of non-subject-antibody materials with which it is associated in nature have been removed. For example, a polynucleotide or a polypeptide naturally present in a living animal is not "isolated," but the same polynucleotide or polypeptide separated from the coexisting materials of its natural state is "isolated." Further, recombinant DNA molecules contained in a vector are considered isolated for the purposes of the present invention. Isolated RNA molecules include in vivo or in vitro RNA replication products of DNA and RNA molecules. Isolated nucleic acid molecules further include synthetically produced molecules. Additionally, vector molecules contained in recombinant host cells are also isolated. Thus, not all "isolated" molecules need be "purified."

As used herein, the term "purified" when used in reference to a molecule, it means that the concentration of the molecule being purified has been increased relative to molecules associated with it in its natural environment, or environment in which it was produced, found or synthesized. Naturally associated molecules include proteins, nucleic acids, lipids and sugars but generally do not include water, buffers, and reagents added to maintain the integrity or facilitate the purification of the molecule being purified. According to this definition, a substance may be 5% or more, 10% or more, 20% or more, 30% or more, 40% or more, 50% or more, 60% or more, 70% or more, 80% or more, 90% or more, 95% or more, 98% or more, 99% or more, or 100% pure when considered relative to its contaminants.

DETAILED DESCRIPTION OF THE INVENTION

The invention provides novel, orally available, potent and selective inhibitors or inactivators of PADs, pharmaceutical compositions and methods of use thereof. The compounds and pharmaceutical compositions of the invention may be used to treat immune system disorders and inflammatory diseases and conditions (e.g., rheumatoid arthritis, lupus). Diseases and conditions that may benefit from treatment using the compounds and pharmaceutical compositions of the invention include ulcerative colitis, spinal cord injury, breast cancer, and atherosclerosis.

Certain benzimidazole-based PAD inhibitors or inactivators disclosed herein display improved metabolic stability, cell permeability and/or potency. It is believed that certain compounds of the invention can access binding regions within PAD2 and PAD4 that had not been previously accessed.

For example, certain compounds disclosed herein possess superior PAD2 inhibition ($kinact/K_I > 300,000$ $kinact/K_I$) and selectivity (~100-fold selective for PAD2 vs PAD4). Certain compounds disclosed herein exhibit improved cell permeability (e.g., over a 10-fold increase in Clog P compared to the peptide-based inhibitor Cl-amidine).

The invention also provides novel potent and selective molecular probes (e.g., imaging probes) for PADs based on the inhibitors or inactivators of PADs disclosed herein in conjugation with detectable labels such as fluorescent dyes, and methods of use thereof. The molecular imaging probes of the invention may be used to screen compounds for PAD inhibition or inactivation.

Aberrantly upregulated protein citrullination is associated with a variety of autoimmune diseases (e.g., rheumatoid arthritis, multiple sclerosis, lupus, and ulcerative colitis), as well as certain cancers. Given these disease links, the protein arginine deiminases have garnered significant recent interest. (Jones, et al. 2009 *Curr Opin Drug Discov Devel* 12, 616-627; Bicker, et al. 2013 *Biopolymers* 99, 155-163; Vossenaar, et al. 2003 *Bioessays* 25, 1106-1118.)

The most deeply investigated disease associated with aberrantly increased PAD activity is RA, where these patients produce autoantibodies that target numerous citrullinated proteins (e.g., citrullinated keratin, fibrin, vimentin and enolase). Importantly, the presence of these autoantibodies is the most specific diagnostic test available for RA. The presence of these anti-citrullinated protein antibodies (i.e., ACPA) is highly predictive of both disease incidence and severity. (Van Steendam, et al. 2011 *Rheumatology*

(Oxford) 50, 830-837; Puszczewicz, et al. 2011 Arch Med Sci 7, 189-194; van Boekel, et al. 2002 Arthritis Res 4, 87-93; Masson-Bessiere, et al. 2001 J Immunol 166, 4177-4184; Burska, et al. 2014 Mediators Inflamm 2014, 492873.)

In addition to ACPA, the PADs themselves are present in the synovial joints of patients with RA where they remain active and citrullinate proteins within the joints that bind ACPA, thereby setting up a classic positive feedback loop that recruits additional immune cells into the joint, the release of additional PAD isozymes into the synovium and enhanced protein citrullination and consequent inflammation. (Burska, et al. 2014 Mediators Inflamm 2014, 492873; Damgaard, et al. 2014 Arthritis Res Ther 16, 498.)

Without wishing to be bound by the theories discussed herein, the specific cells that release PAD isozymes into the joints of RA patients are likely neutrophils. Neutrophils are the predominant white blood cell in humans and are generally the first responders to signs of infection/inflammation. Depending on the environmental cues, a subset of these cells will undergo a novel form of cell death known as Neutrophil Extracellular trap formation (NET) or NETosis. Neutrophils have long been known to be important players in the development and progression of RA as they are the predominant cell type in the synovial fluid of RA patients. Enhanced NETosis, as is observed in RA, also results in the exposure of citrullinated autoantigens, which is key to the progression of RA. (Khandpur, et al. 2013 Sci Transl Med 5, 178ra140; Li, et al. 2010 J Exp Med 207, 1853-1862; Brinkmann, et al. 2004 Science 303, 1532-1535; Ottonello, et al. 2002 Rheumatology (Oxford) 41, 1249-1260; Weissmann, et al. 1984 Inflammation 8 Suppl, 53-14.)

In regard to characteristic features of other inflammatory diseases, enhanced citrullination in the inflamed regions indicates that abberant NETosis may contribute to these diseases as well. In addition, since the PADs are histone-modifying enzymes that contribute to the epigenetic control of gene expression, there is emerging evidence to suggest that enhanced PAD activity promotes an inflamed state by altering the expression and/or activity of key cytokines and chemokines. (Kawalkowska, et al. 2016 Sci Rep 6, 26430; Loos, et al. 2008 Blood 112, 2648-2656; Proost, et al. 2008 J Exp Med 205, 2085-2097; Struyf, et al. 2009 J Immunol 182, 666-674.)

The role the PADs play in these diseases is further highlighted by the efficacy of several PAD inhibitors in a variety of pre-clinical disease models. Specifically, the first-generation irreversible inhibitor Cl-amidine has demonstrated efficacy in animal models of rheumatoid arthritis, lupus, ulcerative colitis, spinal cord injury, breast cancer, and atherosclerosis. (Khandpur, et al. 2013 Sci Transl Med 5, 178ra140; Wang, et al. 2012 J Biol Chem 287, 25941-25953; Chumanevich, et al. 2011 Am J Physiol Gastrointest Liver Physiol 300, G929-938; Lange, et al. 2011 Dev Biol 355, 205-214; Causey, et al. 2011 J Med Chem 54, 6919-6935; Knight, et al. 2012 Curr Opin Rheumatol 24, 441-450; Knight, et al. 2013 J Clin Invest 123, 2981-2993; Smith, et al. 2014 Arthritis Rheumatol 66, 2532-2544; Knight, et al. 2014 Circ Res 114, 947-956; McElwee, et al. 2012 BMC Cancer 12, 500.)

The first-generation inhibitors suffer a number of limitations including their susceptibility to proteolysis and poor membrane permeability. This prompted the development of second-generation inhibitors predicated on improving metabolic stability and membrane permeability.

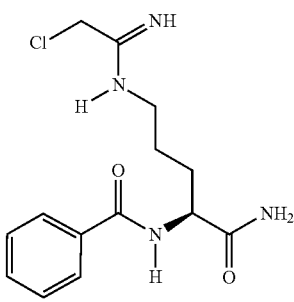

Cl-amidine

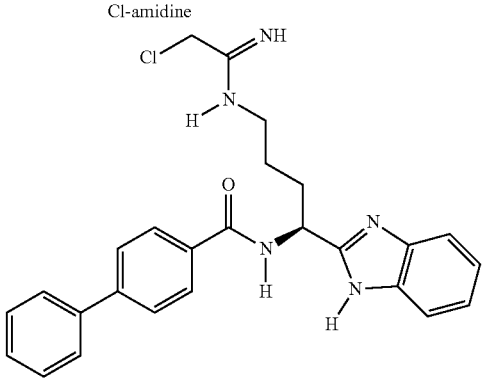

BB-Cl-amidine

Reports have shown that a second-generation inhibitor, BB-Cl-amidine, exhibits enhanced efficacy over Cl-amidine in animal models of lupus and RA. Moreover, the allosteric inhibitor GSK199 also shows efficacy in an RA model. Together, these findings have validated the PADs as viable therapeutic targets for a wide range of inflammatory conditions. (Kawalkowska, et al. 2016 Sci Rep 6, 26430; Knight, et al. 2015 Ann Rheum Dis 74, 2199-2206; Ghari, et al. 2016 Sci Adv 2, e1501257; Willis, V. C. The Role of Citrullination in the Development of Mouse and Human Inflammatory Arthritis. University of Colorado Boulder, Boulder, Colo., 2012.)

The novel PAD inhibitors or inactivators disclosed herein may be used to treat a variety of diseases where PAD activity is dysregulated, for example, RA, lupus, atherosclerosis as well as other inflammatory diseases. These PAD inhibitors may also find use in treating individuals with spinal cord injuries as well as psoriasis. Specifically, certain PAD inhibitors disclosed herein exhibit enhanced potency and selectivity for PAD2, and so they may be used to treat diseases where PAD2 activity is upregulated. Certain disclosed inhibitors may be useful in treating certain cancers such as HER2 overexpressing breast cancers and certain lung cancers, as well as in the treatment of multiple sclerosis.

The PAD molecular probes disclosed herein may be specifically designed with a terminal alkyne so they can covalently modify the PAD enzyme and undergo a subsequent "click" reaction with either TAMRA-$N_3$ or Biotin-$N_3$. These probes may find use in identifying particular diseases where the PADs are upregulated, as well as identifying PAD isozyme-specific diseases. These probes should also find utility in identifying proteins that interact with the PADs as well as in identifying compounds with inhibitory properties or binding affinities to PADs.

In one aspect, the invention generally relates to a compound having the structural formula (I),

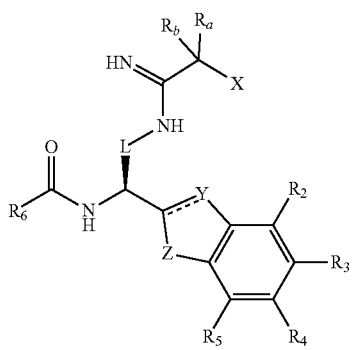

(I)

wherein
each of $R_a$ and $R_b$ is independently selected from the group consisting of H, D and F;

L is a bivalent hydrocarbyl linker, optionally with one or more carbon atoms replaced by a heteroatom selected from the group consisting of O, S and N;

X is a halogen atom;

Y is N, O or S; provided that when Y is S or O, its bonding to the adjacent carbons are single bonds;

Z is N—$R_1$, O or S;

$R_1$ is selected from the group consisting of: H, a $C_{1-6}$ alkyl, OH, a $C_{1-3}$ alkoxy, $CF_3$, $COCH_3$, and $COCF_3$ groups;

each of $R_2$, $R_3$, $R_4$ and $R_5$ is independently selected from the group consisting of: H, hydroxyl, halogen atom, $C_{1-6}$ alkyl, $C_{1-6}$ alkoxy, alkynyl, $CF_2R_c$ and $OCF_2R_c$ groups, where $R_c$ is H, F or alkyl; and $R_6$ is a group comprising a cyclic alkyl or aryl moiety, or a pharmaceutically acceptable form thereof.

In certain embodiments, each of $R_a$ and $R_b$ is H.

In certain embodiments, L is a —$(CH_2)_n$—, wherein n is an integer from 1 to about 4 (e.g., n is 1, 2, 3, or 4). In preferred certain embodiments, n is 3 and L is —$(CH_2)_3$—.

In certain embodiments, Y is N and Z is N—$R_1$ with the compound having the structural formula (II):

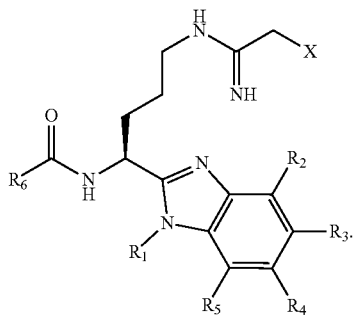

In certain embodiments, X is F. In certain embodiments, X is Cl.

In certain embodiments, $R_1$ is a $C_{1-6}$ alkyl group. In certain embodiments, $R_1$ is H.

In certain embodiments, each of $R_2$, $R_3$, $R_4$ and $R_5$ is H.

In certain embodiments, at least one of $R_2$, $R_3$, $R_4$ and $R_5$ is a group selected from the group consisting of hydroxyl, F, Cl, $C_{1-6}$ alkyl, $C_{1-6}$ alkoxy, alkynyl, $CF_2R_c$, and $OCF_2R$, groups, where $R_c$ is H, F or alkyl.

In certain embodiments, one of $R_2$ and $R_3$ is a group selected from the group consisting of hydroxyl, F, Cl, $C_{1-6}$ alkyl, $C_{1-6}$ alkoxy, alkynyl, $CF_2R_c$, and $OCF_2R_c$ groups, where $R_c$ is H, F or alkyl.

In certain embodiments, $R_6$ is a cyclic, nonaromatic, hydrocarbyl group.

In certain embodiments, $R_6$ is a cyclic, aromatic, hydrocarbyl group.

In certain embodiments, $R_6$ is a heterocyclic, nonaromatic, hydrocarbyl group.

In certain embodiments, $R_6$ is a heterocyclic, aromatic, hydrocarbyl group.

In certain embodiments, $R_6$ is selected from the group consisting of:

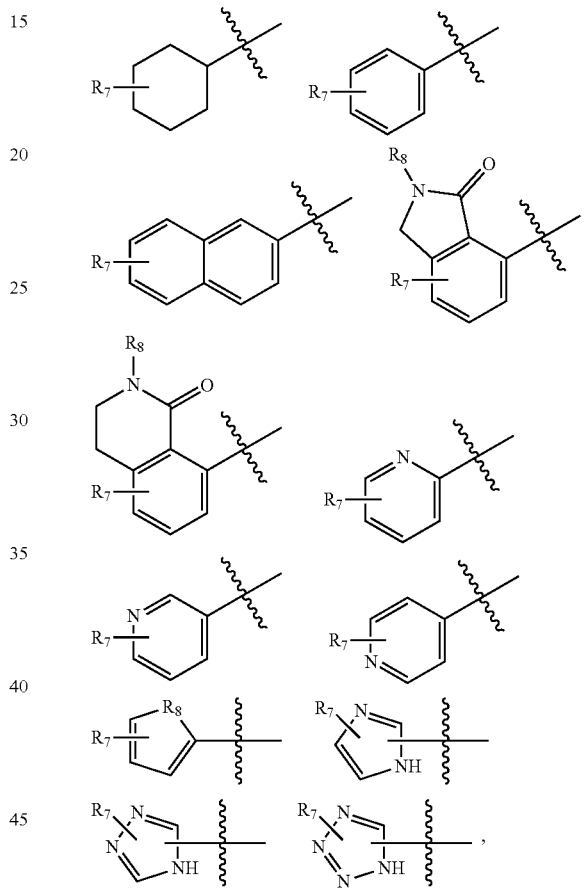

wherein
$R_7$ is independently selected from the group consisting of H, $C_{1-6}$ alkyl, $C_{1-6}$ alkoxy, hydroxyl, halogen atoms, aryl, —$COOR_8$, ethynyl, alkynyl, $CF_2R_c$, and $OCF_2R_c$, where $R_c$ is H, F or alkyl;

$R_8$ is independently selected from the group consisting of H and $C_{1-6}$ alkyl; and $R_9$ is $CH_2$, O, $NH_2$ or S.

In certain embodiments, $R_7$ is H.

In certain embodiments, R is a $C_{1-6}$ alkyl group.

In another aspect, the invention generally relates to a pharmaceutical composition comprising a compound having the structural formula of (I):

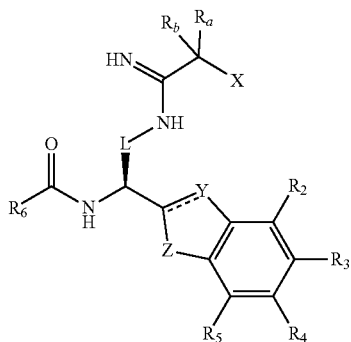

(I)

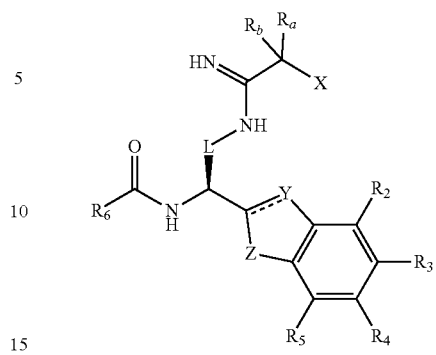

(I)

wherein, each of $R_a$ and $R_b$ is independently selected from the group consisting of H, D and F;

L is a bivalent hydrocarbyl linker, optionally with one or more carbon atoms replaced by a heteroatom selected from the group consisting of O, S and N;

X is a halogen atom;

Y is N, O or S; provided that when Y is S or O, its bonding to the adjacent carbons are single bonds;

Z is N—$R_1$, O or S;

$R_1$ is selected from the group consisting of: H, a $C_{1-6}$ alkyl, OH, a $C_{1-3}$ alkoxy, $CF_3$, $COCH_3$, and $COCF_3$ groups;

each of $R_2$, $R_3$, $R_4$ and $R_5$ is independently selected from the group consisting of: H, hydroxyl, halogen atom, $C_{1-6}$ alkyl, $C_{1-6}$ alkoxy, alkynyl, $CF_2R_c$, and $OCF_2R_c$ groups, where $R_c$ is H, F or alkyl; and $R_6$ is a group comprising a cyclic alkyl or aryl moiety, or a pharmaceutically acceptable form thereof, effective to treat, prevent, or reduce one or more diseases or disorders, in a mammal, including a human, and a pharmaceutically acceptable excipient, carrier, or diluent.

In certain embodiments, the one or more diseases or conditions are selected from the group consisting of immune system diseases or disorders, inflammatory diseases or disorders, and cancer or related diseases or disorders.

In certain embodiments, the one or more diseases or conditions are selected from autoimmune diseases or disorders.

In certain embodiments, the one or more diseases or conditions are selected from the group consisting of lupus, rheumatoid arthritis, Alzheimer's disease, multiple sclerosis and Parkinson's disease.

In certain embodiments, the disease or condition is lupus.

In certain embodiments, the disease or condition is rheumatoid arthritis.

Pharmaceutical compositions of the invention includes that of a compound of the invention disclosed herein.

In yet another aspect, the invention generally relates to a unit dosage form comprising a pharmaceutical composition disclosed herein.

In yet another aspect, the invention generally relates to a method for treating, reducing, or preventing a disease or disorder. The method includes administering to a subject in need thereof a pharmaceutical composition comprising a compound having the structural formula of (I):

wherein, each of $R_a$ and $R_b$ is independently selected from the group consisting of H, D and F;

L is a bivalent hydrocarbyl linker, optionally with one or more carbon atoms replaced by a heteroatom selected from the group consisting of O, S and N;

X is a halogen atom;

Y is N, O or S; provided that when Y is S or O, its bonding to the adjacent carbons are single bonds;

Z is N—$R_1$, O or S;

$R_1$ is selected from the group consisting of: H, a $C_{1-6}$ alkyl, OH, a $C_{1-3}$ alkoxy, $CF_3$, $COCH_3$, and $COCF_3$ groups;

each of $R_2$, $R_3$, $R_4$ and $R_5$ is independently selected from the group consisting of: H, hydroxyl, halogen atom, $C_{1-6}$ alkyl, $C_{1-6}$ alkoxy, alkynyl, $CF_2R_c$, and $OCF_2R_c$ groups, where $R_c$ is H, F or alkyl; and $R_6$ is a group comprising a cyclic alkyl or aryl moiety, or a pharmaceutically acceptable form thereof, and a pharmaceutically acceptable excipient, carrier, or diluent, effective to treat, prevent, or reduce one or more diseases or disorders, in a mammal, including a human.

In certain embodiments, the one or more diseases or conditions are selected from the group consisting of immune system diseases or disorders, inflammatory diseases or disorders, and cancer or related diseases or disorders.

In certain embodiments, the one or more diseases or conditions are selected from autoimmune diseases or disorders In certain embodiments, the one or more diseases or conditions are selected from the group consisting of lupus, rheumatoid arthritis, Alzheimer's disease, multiple sclerosis and Parkinson's disease.

In certain embodiments, the disease or condition is lupus.

In certain embodiments, the disease or condition is rheumatoid arthritis.

In yet another aspect, the invention generally relates to a method for inhibiting or inactivating a protein arginine deiminase, comprising administering to a subject in need thereof a pharmaceutical composition comprising a compound having the structural formula of (I):

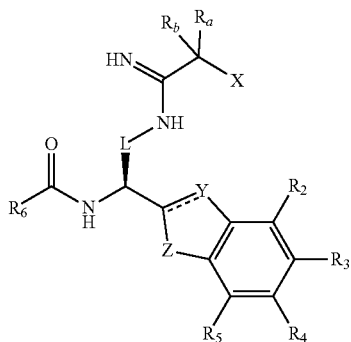

(I)

wherein, each of $R_a$ and $R_b$ is independently selected from the group consisting of H, D and F;

L is a bivalent hydrocarbyl linker, optionally with one or more carbon atoms replaced by a heteroatom selected from the group consisting of O, S and N;

X is a halogen atom;

Y is N, O or S; provided that when Y is S or O, its bonding to the adjacent carbons are single bonds;

Z is N—$R_1$, O or S;

$R_1$ is selected from the group consisting of: H, a $C_{1-6}$ alkyl, OH, a $C_{1-3}$ alkoxy, $CF_3$, $COCH_3$, and $COCF_3$ groups;

each of $R_2$, $R_3$, $R_4$ and $R_5$ is independently selected from the group consisting of: H, hydroxyl, halogen atom, $C_{1-6}$ alkyl, $C_{1-6}$ alkoxy, alkynyl, $CF_2R_c$ and $OCF_2R_c$ groups, where $R_c$ is H, F or alkyl; and $R_6$ is a group comprising a cyclic alkyl or aryl moiety, or a pharmaceutically acceptable form thereof, and a pharmaceutically acceptable excipient, carrier, or diluent, effective to inhibit or inactivate a biological function of a protein arginine deiminase, in a mammal, including a human.

In certain embodiments, the protein arginine deiminase is selected from the group consisting of: PAD1, PAD2, PAD3 and PAD4.

In certain embodiments, the protein arginine deiminase is PAD2.

In certain embodiments, the protein arginine deiminase is PAD4.

In yet another aspect, the invention generally relates to a molecular imaging probe having the structural formula:

$$A_F\text{-}L_F\text{-}W \quad (II)$$

wherein $A_F$ is a group comprising an optically detectable moiety;

$L_F$ is a linking group; and

W is group comprising a benzimidazole moiety, or a derivative or analog thereof, capable of inhibiting or inactivating a biological function of a protein arginine deiminase.

In certain embodiments, $A_F$ is a group comprising a fluorophore.

In certain embodiments, the fluorophore is selected from the group consisting of xanthene dyes, cyanine dyes, coumarin dyes and bodipy dyes.

In certain embodiments, the fluorophore is a xanthene dye selected from the group consisting of fluorescein, eosins, and rhodamines.

In certain embodiments, the fluorophore is a cyanine dye.

In certain embodiments, the fluorophore is a coumarin dye.

In certain embodiments, the fluorophore is a bodipy dye.

In certain embodiments, the protein arginine deiminase is selected from the group consisting of: PAD1, PAD2, PAD3 and PAD4.

In certain embodiments, the protein arginine deiminase is PAD2.

In certain embodiments, the protein arginine deiminase is PAD4.

In certain embodiments, W is a monovalent radical derived from a compound having the structural formula:

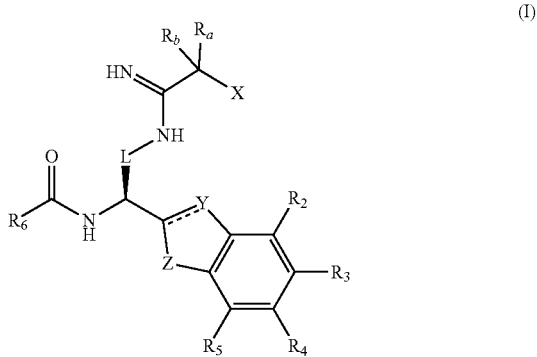

(I)

wherein, each of $R_a$ and $R_b$ is independently selected from the group consisting of H, D and F;

L is a bivalent hydrocarbyl linker, optionally with one or more carbon atoms replaced by a heteroatom selected from the group consisting of O, S and N;

X is a halogen atom;

Y is N, O or S; provided that when Y is S or O, its bonding to the adjacent carbons are single bonds;

Z is N—$R_1$, O or S;

$R_1$ is selected from the group consisting of: H, a $C_{1-6}$ alkyl, OH, a $C_{1-3}$ alkoxy, $CF_3$, $COCH_3$, and $COCF_3$ groups;

each of $R_2$, $R_3$, $R_4$ and $R_5$ is independently selected from the group consisting of: H, hydroxyl, halogen atom, $C_{1-6}$ alkyl, $C_{1-6}$ alkoxy, alkynyl, $CF_2R_c$ and $OCF_2R_c$ groups, where $R_c$ is H, F or alkyl; and $R_6$ is a group comprising a cyclic alkyl or aryl moiety.

In yet another aspect, the invention generally relates to a method for identifying a protein arginine deiminase inhibitor or inactivator. The method includes: performing a competitive assay wherein a test compound competes with a molecular imaging probe disclosed herein to bind to a protein arginine deiminase; and measuring fluorescence to determine an amount of fluorescent protein arginine deiminase present in the test assay.

In certain embodiments, the method further includes: performing a control assay wherein the molecular imaging probe binds to the protein arginine deiminase; and measuring fluorescence to determine an amount of fluorescent protein arginine deiminase present in the control assay.

In certain embodiments, a change in fluorescence in the assay greater than a pre-selected value when compared to the control assay is indicative that the test compound is an inhibitor to the protein arginine deiminase.

In certain embodiments, the change in fluorescence in the assay is a decrease in fluorescence in the assay.

EXAMPLES

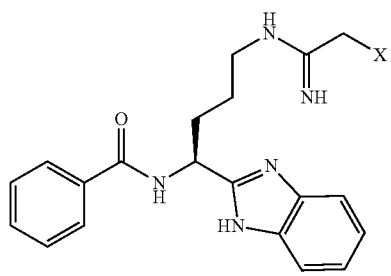

5a-b

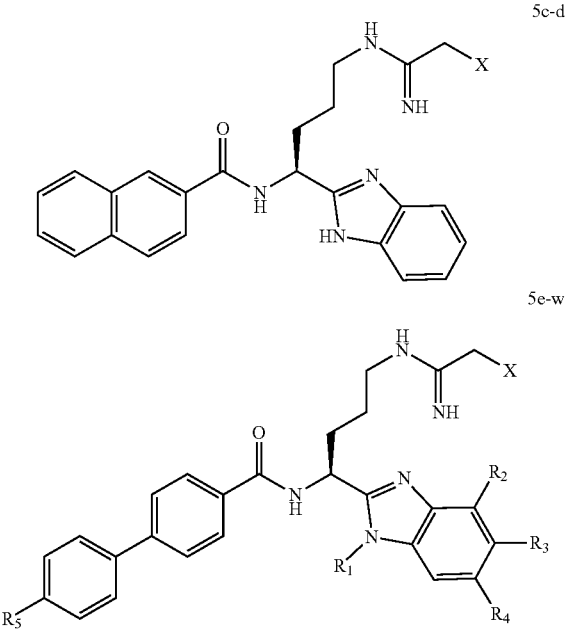

5c-d 5e-w

TABLE 1a $k_{inact}/K_I$ values for compounds 5a-w

| Compound | PAD1 $k_{inact}/K_I$ ($M^{-1}min^{-1}$) | PAD2 $k_{inact}/K_I$ ($M^{-1}min^{-1}$) | PAD3 $k_{inact}/K_I$ ($M^{-1}min^{-1}$) | PAD4 $k_{inact}/K_I$ ($M^{-1}min^{-1}$) |
|---|---|---|---|---|
| 5a (X=F) | 4500 (±300)[a] | 475 (±20)[a] | 900 (±200)[a] | 8500 (±1300)[a] |
| 5b (X=Cl) | 7950 (±675)[a] | 500 (±50)[a] | 9770 (±350)[a] | 15250 (±675)[a] |
| 5c (X=F) | 1500 (±400)[a] | 785 (±60)[a] | 2800 (±500)[a] | 6500 (±700)[a] |
| 5d (X=Cl) | 2800 (±550)[a] | 4275 (±250)[a] | 9875 (±500)[a] | 10000 (±1000)[a] |
| 5e ($R_1=R_2=R_3=R_4=R_5=H$, X=F) | 900 (±100)[a] | 1200 (±30)[a] | 3400 (±140)[a] | 3750 (±250)[a] |
| 5f ($R_1=R_2=R_3=R_4=R_5=H$, X=Cl) | 16100 (±1500)[a] | 4100 (±400)[a] | 6800 (±200)[a] | 13300 (±3000)[a] |
| 5g ($R_1=Me$, $R_2=R_3=R_4=R_5=H$, X=F) | 1280 (±120)[a] | 820 (±90)[b] | 1600 (±210)[a] | 450 (±50)[b] |
| 5h ($R_1=Me$, $R_2=H$, $R_2=R_3=R_4=R_5=H$, X=Cl) | 6750 (±500)[a] | 2430 (±400)[a] | 6020 (±650)[a] | 3110 (±420)[a] |
| 5i ($R_1=Et$, $R_2=H$, $R_2=R_3=R_4=R_5=H$, X=F) | 760 (±100)[a] | 1160 (±100)[b] | 1800 (±210)[a] | 30 (±5)[b] |
| 5j ($R_1=Et$, $R_2=H$, $R_2=R_3=R_4=R_5=H$, X=Cl) | 5060 (±650)[a] | 4850 (±320)[a] | 17040 (±2100)[a] | 4150 (±420)[a] |
| 5k ($R_1={}^iPr$, $R_2=H$, $R_2=R_3=R_4=R_5=H$, X=F) | 20 (±10)[a] | 680 (±50)[b] | 1700 (±190)[a] | 20 (±5)[b] |
| 5l ($R_1={}^iPr$, $R_2=H$, $R_2=R_3=R_4=R_5=H$, X=Cl) | 1220 (±190)[a] | 1490 (±180)[a] | 11500 (±1500)[a] | 950 (±130)[a] |
| 5m ($R_1=Me$, $R_2=R_3=R_4=R_5=H$, $R_2=OMe$, X=F) | 1870 (±180)[a] | 7920 (±1100)[a] | 2900 (±310)[a] | 790 (±95)[a] |
| 5n ($R_1=Me$, $R_2=R_3=R_4=R_5=H$, $R_2=OMe$, X=Cl) | 34800 (±4200)[a] | 27800 (±3500)[a] | 5500 (±810)[a] | 7900 (±710)[a] |
| 5o ($R_1=R_2=R_3=R_4=H$, $R_5=F$, X=F) | 1400 (±120)[a] | 1700 (±210)[a] | 1620 (±190)[a] | 3200 (±380)[a] |
| 5p ($R_1=R_2=R_3=R_4=H$, $R_5=F$, X=Cl) | 20600 (±2400)[a] | 5500 (±620)[a] | 10530 (±1100)[a] | 16800 (±1800)[a] |
| 5q ($R_1=R_2=R_5=H$, $R_3=R_4=F$, X=F) | 1860 (±190)[a] | 1570 (±200)[a] | 1530 (±140)[a] | 3600 (±420)[a] |
| 5r ($R_1=R_2=R_5=H$, $R_3=R_4=F$, X=Cl) | 27400 (±3100)[a] | 5600 (±610)[a] | 14360 (±1500)[a] | 20220 (±2150)[a] |
| 5s ($R_1=R_2=H$, $R_3=R_4=R_5=F$, X=F) | 1790 (±230)[a] | 1420 (±170)[a] | 1100 (±160)[a] | 4040 (±480)[a] |

TABLE 1a-continued k$_{inact}$/K$_I$ values for compounds 5a-w

| Compound | PAD1 k$_{inact}$/K$_I$ (M$^{-1}$min$^{-1}$) | PAD2 k$_{inact}$/K$_I$ (M$^{-1}$min$^{-1}$) | PAD3 k$_{inact}$/K$_I$ (M$^{-1}$min$^{-1}$) | PAD4 k$_{inact}$/K$_I$ (M$^{-1}$min$^{-1}$) |
|---|---|---|---|---|
| 5t (R$_1$=R$_2$=H, R$_3$=R$_4$=R$_5$=F, X=Cl) | 30480 (±5350)[a] | 5730 (±590)[a] | 7180 (±790)[a] | 21250 (±2500)[a] |
| 5u (R$_1$=R$_2$=R$_3$=R$_4$=H, R$_5$=CCH, X=F) | 4650 (±80)[a] | 975 (±30)[a] | 1025 (±25)[a] | 1770 (±110)[a] |
| 5v (R$_1$=R$_2$=R$_3$=R$_4$=H, R$_5$=CCH, X=Cl) | 415 (±70)[a] | 875 (±70)[a] | 375 (±50)[a] | 1300 (±100)[a] |

[a] A single k$_{obs}$ was determined.
[b] k$_{inact}$/K$_I$ was determined from a linear fit.

TABLE 1b

Summary of isozyme selectivity for compounds 5a-w

| Compound | Fold PAD1 Selectivity | Fold PAD2 Selectivity | Fold PAD3 Selectivity | Fold PAD4 Selectivity |
|---|---|---|---|---|
| 5a (X=F) | 9.5 | 1.0 | 1.9 | 18 |
| 5b (X=Cl) | 16 | 1.0 | 20 | 31 |
| 5c (X=F) | 1.9 | 1.0 | 3.6 | 8.3 |
| 5d (X=Cl) | 1.0 | 1.5 | 3.5 | 3.6 |
| 5e (R$_1$=R$_2$=R$_3$=R$_4$=R$_5$=H, X=F) | 1.0 | 1.3 | 3.8 | 4.2 |
| 5f (R$_1$=R$_2$=R$_3$=R$_4$=R$_5$=H, X=Cl) | 3.9 | 1.0 | 1.7 | 3.2 |
| 5g (R$_1$=Me, R$_2$=R$_3$=R$_4$=R$_5$=H, X=F) | 2.8 | 1.8 | 3.6 | 1.0 |
| 5h (R$_1$=Me, R$_2$=H, R$_2$=R$_3$=R$_4$=R$_5$=H, X=Cl) | 2.8 | 1.0 | 2.5 | 1.3 |
| 5i (R$_1$=Et, R$_2$=H, R$_2$=R$_3$=R$_4$=R$_5$=H, X=F) | 25 | 39 | 60 | 1.0 |
| 5j (R$_1$=Et, R$_2$=H, R$_2$=R$_3$=R$_4$=R$_5$=H, X=Cl) | 1.2 | 1.2 | 4.1 | 1.0 |
| 5k (R$_1$=$^i$Pr, R$_2$=H, R$_2$=R$_3$=R$_4$=R$_5$=H, X=F) | 1.0 | 34 | 85 | 1.0 |
| 5l (R$_1$=$^i$Pr, R$_2$=H, R$_2$=R$_3$=R$_4$=R$_5$=H, X=Cl) | 1.3 | 1.6 | 12 | 1.0 |
| 5m (R$_1$=Me, R$_2$=R$_3$=R$_4$=R$_5$=H, R$_2$=OMe, X=F) | 2.4 | 10 | 3.7 | 1.0 |
| 5n (R$_1$=Me, R$_2$=R$_3$=R$_4$=R$_5$=H, R$_2$=OMe, X=Cl) | 6.3 | 5.1 | 1.0 | 1.4 |
| 5o (R$_1$=R$_2$=R$_3$=R$_4$=H, R$_5$=F, X=F) | 1.0 | 1.2 | 1.2 | 2.3 |
| 5p (R$_1$=R$_2$=R$_3$=R$_4$=H, R$_5$=F, X=Cl) | 3.7 | 1.0 | 1.9 | 3.1 |
| 5q (R$_1$=R$_2$=R$_5$=H, R$_3$=R$_4$=F, X=F) | 1.2 | 1.0 | 1.0 | 2.4 |
| 5r (R$_1$=R$_2$=R$_5$=H, R$_3$=R$_4$=F, X=Cl) | 4.9 | 1.0 | 2.6 | 3.6 |
| 5s (R1=R$_2$=H, R$_3$=R$_4$=R$_5$=F, X=F) | 1.6 | 1.3 | 1.0 | 3.7 |
| 5t (R1=R$_2$=H, R$_3$=R$_4$=R$_5$=F, X=Cl) | 5.3 | 1.0 | 1.3 | 3.7 |
| 5u (R1=R$_2$=R$_3$=R$_4$=H, R$_5$=CCH, X=F) | 4.8 | 1.0 | 1.1 | 1.8 |
| 5v (R$_1$=R$_2$=R$_3$=R$_4$=H, R$_5$=CCH, X=Cl) | 1.1 | 2.3 | 1.0 | 3.5 |

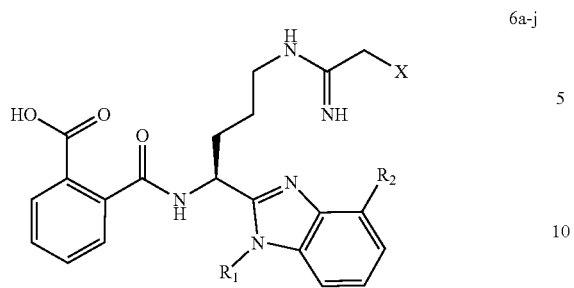

6a-j

TABLE 2a $k_{inact}/K_I$ values for compounds 6a-j

| Compound | PAD1 $k_{inact}/K_I$ ($M^{-1}min^{-1}$) | PAD2 $k_{inact}/K_I$ ($M^{-1}min^{-1}$) | PAD3 $k_{inact}/K_I$ ($M^{-1}min^{-1}$) | PAD4 $k_{inact}/K_I$ ($M^{-1}min^{-1}$) |
|---|---|---|---|---|
| 6a ($R_1$=$R_2$=H, X=F) | 16500 (±2200)[a] | 1500 (±300)[a] | 6500 (±300)[a] | 24300 (±1800)[a] |
| 6b ($R_1$=$R_2$=H, X=Cl) | 28500 (±2900)[a] | 3450 (±100)[a] | 21250 (±2750)[a] | 31000 (±1550)[a] |
| 6c ($R_1$=Me, $R_2$=H, X=F) | 32300 (±4400)[a] | 11800 (±1090)[b] | 1030 (±150)[a] | 800 (±90)[b] |
| 6d ($R_1$=Me, $R_2$=H, X=Cl) | 32200 (±3540)[a] | 14400 (±1230)[a] | 7500 (±810)[a] | 7800 (±770)[a] |
| 6e ($R_1$=Et, $R_2$=H, X=F) | 39000 (±4600)[a] | 31600 (±3030)[b] | 1750 (±180)[a] | 1010 (±170)[b] |
| 6f ($R_1$=Et, $R_2$=H, X=Cl) | 47100 (±4600)[a] | 17400 (±2100)[a] | 11000 (±1300)[a] | 13700 (±1500)[a] |
| 6g ($R_1$=$^i$Pr, $R_2$=H, X=F) | 22700 (±2400)[a] | 24700 (±2900)[a] | 2010 (±190)[a] | 460 (±80)[a] |
| 6h ($R_1$=$^i$Pr, $R_2$=H, X=Cl) | 49000 (±5100)[a] | 27100 (±2400)[a] | 2700 (±290)[a] | 720 (±90)[a] |
| 6i ($R_1$=Me, $R_2$=OMe, X=F) | 37600 (±3900)[a] | 20400 (±1900)[a] | 6800 (±770)[a] | 6040 (±610)[a] |
| 6j ($R_1$=Me, $R_2$=OMe, X=Cl) | 67300 (±7100)[a] | 18500 (±1900)[a] | 9600 (±1200)[a] | 14100 (±1600)[a] |

[a] A single $k_{obs}$ was determined.
[b] $k_{inact}/K_I$ was determined from a linear fit.

TABLE 2b

Summary of isozyme selectivity for compounds 6a-j

| Compound | Fold PAD1 Selectivity | Fold PAD2 Selectivity | Fold PAD3 Selectivity | Fold PAD4 Selectivity |
|---|---|---|---|---|
| 6a ($R_1$=$R_2$=H, X=F) | 11 | 1.0 | 4.3 | 16 |
| 6b ($R_1$=$R_2$=H, X=Cl) | 8.3 | 1.0 | 6.2 | 9.0 |
| 6c ($R_1$=Me, $R_2$=H, X=F) | 40 | 15 | 1.3 | 1.0 |
| 6d ($R_1$=Me, $R_2$=H, X=Cl) | 4.3 | 1.9 | 1.0 | 1.0 |
| 6e ($R_1$=Et, $R_2$=H, X=F) | 39 | 31 | 1.7 | 1.0 |
| 6f ($R_1$=Et, $R_2$=H, X=Cl) | 4.3 | 1.6 | 1.0 | 1.2 |
| 6g ($R_1$=$^i$Pr, $R_2$=H, X=F) | 49 | 54 | 4.4 | 1.0 |
| 6h ($R_1$=$^i$Pr, $R_2$=H, X=Cl) | 68 | 38 | 3.8 | 1.0 |
| 6i ($R_1$=Me, $R_2$=OMe, X=F) | 6.2 | 3.4 | 1.1 | 1.0 |
| 6j ($R_1$=Me, $R_2$=OMe, X=Cl) | 7.0 | 1.9 | 1.0 | 1.5 |

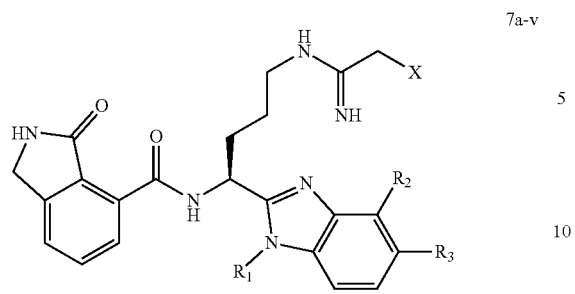

7a-v

TABLE 3a $k_{inact}/K_I$ values for compounds 7a-v

| Compound | PAD1 $k_{inact}/K_I$ ($M^{-1}min^{-1}$) | PAD2 $k_{inact}/K_I$ ($M^{-1}min^{-1}$) | PAD3 $k_{inact}/K_I$ ($M^{-1}min^{-1}$) | PAD4 $k_{inact}/K_I$ ($M^{-1}min^{-1}$) |
|---|---|---|---|---|
| 7a ($R_1$=H, $R_2$=H, $R_3$=H, X=F) | 77180 (±15000)[a] | 10600 (±3290)[c] | 3200 (±450)[a] | 33100 (±3350)[b] |
| 7b ($R_1$=H, $R_2$=H, $R_3$=H, X=Cl) | 180830 (±23500)[a] | 65400 (±9400)[a] | 28020 (±3100)[a] | 58100 (±4600)[a] |
| 7c ($R_1$=Me, $R_2$=H, $R_3$=H, X=F) | 68670 (±9600)[a] | 24800 (±3200)[a] | 2800 (±310)[a] | 2910 (±270)[a] |
| 7d ($R_1$=Me, $R_2$=H, $R_3$=H, X=Cl) | 146000 (±22500)[a] | 72900 (±9350)[a] | 48500 (±3750)[a] | 23900 (±2760)[a] |
| 7e ($R_1$=Et, $R_2$=H, $R_3$=H, X=F) | 40500 (±6400)[a] | 61600 (±7750)[d] | 1100 (±210)[a] | 1900 (±270)[b] |
| 7f ($R_1$=Et, $R_2$=H, $R_3$=H, X=Cl) | 132000 (±2200)[a] | 60500 (±8160)[a] | 22600 (±3400)[a] | 12600 (±1800)[a] |
| 7g ($R_1$=$^i$Pr, $R_2$=H, $R_3$=H, X=F) | 6220 (±790)[a] | 10300 (±1300)[a] | 510 (±75)[a] | 1230 (±160)[b] |
| 7h ($R_1$=$^i$Pr, $R_2$=H, $R_3$=H, X=Cl) | 57600 (±7560)[a] | 16900 (±2200)[a] | 6700 (±560)[a] | 2100 (±310)[a] |
| 7i ($R_1$=H, $R_2$=OMe, $R_3$=H, X=F) | 91600 (±12300)[a] | 17500 (±2130)[a] | 8250 (±980)[a] | 2180 (±420)[a] |
| 7j ($R_1$=H, $R_2$=OMe, $R_3$=H, X=Cl) | 130830 (±35600)[a] | 48140 (±6300)[a] | 30120 (±3820)[a] | 4340 (±620)[a] |
| 7k ($R_1$=Me, $R_2$=OMe, $R_3$=H, X=F) | 129100 (±26300)[a] | 210300 (±58200)[e] | 4430 (±510)[a] | 14300 (±4800)[a] |
| 7l ($R_1$=Me, $R_2$=OMe, $R_3$=H, X=Cl) | 77900 (±7500)[a] | 77800 (±10900)[a] | 19900 (±2120)[a] | 25300 (±2410)[a] |
| 7m ($R_1$=Me, $R_2$=OEt, $R_3$=H, X=F) | 64400 (±8320)[a] | 94450 (±17700)[f] | 1200 (±150)[a] | 990 (±110)[a] |
| 7n ($R_1$=Me, $R_2$=OEt, $R_3$=H, X=Cl) | 58900 (±4500)[a] | 71850 (±8320)[a] | 6470 (±680)[a] | 2410 (±320)[a] |
| 7o ($R_1$=Me, $R_2$=H, $R_3$=OMe, X=F) | 124900 (±33500)[a] | 117300 (±19500)[g] | 1030 (±90)[a] | 1230 (±140)[a] |
| 7p ($R_1$=Me, $R_2$=H, $R_3$=OMe, X=Cl) | 132800 (±27800)[a] | 54490 (±6230)[a] | 13100 (±1450)[a] | 5410 (±570)[a] |
| 7q ($R_1$=Et, $R_2$=OMe, $R_3$=H, X=F) | 59900 (±6320)[a] | 50700 (±4350)[a] | 1600 (±180)[a] | 1580 (±140)[a] |
| 7r ($R_1$=Et, $R_2$=OMe, $R_3$=H, X=Cl) | 107200 (±12300)[a] | 39440 (±4200)[a] | 6180 (±710)[a] | 2130 (±210)[a] |
| 7s ($R_1$=H, $R_2$=H, $R_3$=OMe, X=F) | 58410 (±4320)[a] | 24880 (±3120)[a] | 4570 (±630)[a] | 15850 (±1890) |
| 7t ($R_1$=H, $R_2$=H, $R_3$=OMe, X=Cl) | 127700 (±45300)[a] | 60240 (±8210)[a] | 17450 (±1560)[a] | 37800 (±4120)[a] |
| 7u ($R_1$=Et, $R_2$=H, $R_3$=OMe, X=F) | 18930 (±1900)[a] | 39460 (±3870)[a] | 1980 (±270)[a] | 790 (±160)[a] |
| 7v ($R_1$=Et, $R_2$=H, $R_3$=OMe, X=Cl) | 60530 (±8650)[a] | 46780 (±7410)[a] | 12830 (±1430)[a] | 2930 (±380)[a] |

[a] A single $k_{obs}$ was determined.
[b] $k_{inact}/K_I$ was determined from a linear fit.
[c] $k_{inact}$ = 2.24 min$^{-1}$, $K_I$ = 210 μM.
[d] $k_{inact}$ = 2.02 min$^{-1}$, $K_I$ = 32.9 μM.
[e] $k_{inact}$ = 3.47 min$^{-1}$, $K_I$ = 16.5 μM.
[f] $k_{inact}$ = 5.21 min$^{-1}$, $K_I$ = 55.2 μM.
[g] $k_{inact}$ = 2.42 min$^{-1}$, $K_I$ = 20.7 μM.

TABLE 3b

Summary of isozyme selectivity for compounds 7a-v

| Compound | Fold PAD1 Selectivity | Fold PAD2 Selectivity | Fold PAD3 Selectivity | Fold PAD4 Selectivity |
|---|---|---|---|---|
| 7a ($R_1$=H, $R_2$=H, $R_3$=H, X=F) | 24 | 3.3 | 1.0 | 10 |
| 7b ($R_1$=H, $R_2$=H, $R_3$=H, X=Cl) | 6.5 | 2.3 | 1.0 | 2.1 |
| 7c ($R_1$=Me, $R_2$=H, $R_3$=H, X=F) | 25 | 8.9 | 1.0 | 1.0 |
| 7d ($R_1$=Me, $R_2$=H, $R_3$=H, X=Cl) | 61 | 3.1 | 2.0 | 1.0 |
| 7e ($R_1$=Et, $R_2$=H, $R_3$=H, X=F) | 37 | 56 | 1.0 | 1.7 |
| 7f ($R_1$=Et, $R_2$=H, $R_3$=H, X=Cl) | 10 | 4.8 | 1.8 | 1.0 |
| 7g ($R_1$=$^i$Pr, $R_2$=H, $R_3$=H, X=F) | 12 | 20 | 1.0 | 2.4 |
| 7h ($R_1$=$^i$Pr, $R_2$=H, $R_3$=H, X=Cl) | 27 | 8.0 | 3.2 | 1.0 |
| 7i ($R_1$=H, $R_2$=OMe, $R_3$=H, X=F) | 42 | 8.0 | 3.8 | 1.0 |
| 7j ($R_1$=H, $R_2$=OMe, $R_3$=H, X=Cl) | 30 | 11 | 6.9 | 1.0 |
| 7k ($R_1$=Me, $R_2$=OMe, $R_3$=H, X=F) | 29 | 47 | 1.0 | 3.2 |
| 7l ($R_1$=Me, $R_2$=OMe, $R_3$=H, X=Cl) | 3.9 | 3.9 | 1.0 | 1.3 |
| 7m ($R_1$=Me, $R_2$=OEt, $R_3$=H, X=F) | 65 | 95 | 1.2 | 1.0 |
| 7n ($R_1$=Me, $R_2$=OEt, $R_3$=H, X=Cl) | 24 | 30 | 2.7 | 1.0 |
| 7o ($R_1$=Me, $R_2$=H, $R_3$=OMe, X=F) | 121 | 114 | 1.0 | 1.2 |
| 7p ($R_1$=Me, $R_2$=H, $R_3$=OMe, X=Cl) | 25 | 10 | 2.4 | 1.0 |
| 7q ($R_1$=Et, $R_2$=OMe, $R_3$=H, X=F) | 38 | 32 | 1.0 | 1.0 |
| 7r ($R_1$=Et, $R_2$=OMe, $R_3$=H, X=Cl) | 50 | 19 | 2.9 | 1.0 |
| 7s ($R_1$=H, $R_2$=H, $R_3$=OMe, X=F) | 13 | 5.4 | 1.0 | 3.5 |
| 7t ($R_1$=H, $R_2$=H, $R_3$=OMe, X=Cl) | 7.3 | 3.5 | 1.0 | 2.2 |
| 7u ($R_1$=Et, $R_2$=H, $R_3$=OMe, X=F) | 24 | 50 | 2.5 | 1.0 |
| 7v ($R_1$=Et, $R_2$=H, $R_3$=OMe, X=Cl) | 21 | 16 | 4.4 | 1.0 |

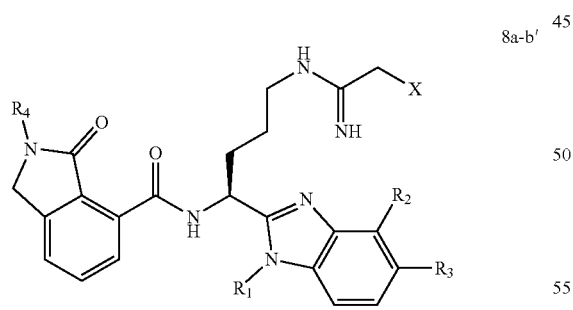

8a-b'

TABLE 4a $k_{inact}/K_I$ values for compounds 8a-b'

| Compound | PAD1 $k_{inact}/K_I$ ($M^{-1}min^{-1}$) | PAD2 $k_{inact}/K_I$ ($M^{-1}min^{-1}$) | PAD3 $k_{inact}/K_I$ ($M^{-1}min^{-1}$) | PAD4 $k_{inact}/K_I$ ($M^{-1}min^{-1}$) |
|---|---|---|---|---|
| 8a ($R_1$=H, $R_2$=H, $R_3$=H, $R_4$=Et, X=F) | 48400 (±5210)$^a$ | 14400 (±1320)$^a$ | 14900 (±1250)$^a$ | 14900 (±1510)$^a$ |

TABLE 4a-continued $k_{inact}/K_I$ values for compounds 8a-b'

| Compound | PAD1 $k_{inact}/K_I$ ($M^{-1}min^{-1}$) | PAD2 $k_{inact}/K_I$ ($M^{-1}min^{-1}$) | PAD3 $k_{inact}/K_I$ ($M^{-1}min^{-1}$) | PAD4 $k_{inact}/K_I$ ($M^{-1}min^{-1}$) |
|---|---|---|---|---|
| 8b ($R_1$=H, $R_2$=H, $R_3$=H, $R_4$=Et, X=Cl) | 151700 (±28900)[a] | 53300 (±6420)[a] | 35000 (±2740)[a] | 48600 (±4600)[a] |
| 8c ($R_1$=Me, $R_2$=H, $R_3$=H, $R_4$=Et, X=F) | 18500 (±2230)[a] | 32760 (±2890)[a] | 5750 (±610)[a] | 3030 (±280)[a] |
| 8d ($R_1$=Me, $R_2$=H, $R_3$=H, $R_4$=Et, X=Cl) | 78910 (±9480)[a] | 71350 (±5210)[a] | 3770 (±240)[a] | 4540 (±330)[a] |
| 8e ($R_1$=Et, $R_2$=H, $R_3$=H, $R_4$=Et, X=F) | 24100 (±1980)[a] | 40610 (±4050)[a] | 1250 (±130)[a] | 1240 (±110)[a] |
| 8f ($R_1$=Et, $R_2$=H, $R_3$=H, $R_4$=Et, X=Cl) | 57100 (±6050)[a] | 45100 (±3030)[a] | 6870 (±790)[a] | 3250 (±280)[a] |
| 8g ($R_1$=$^i$Pr, $R_2$=H, $R_3$=H, $R_4$=Et, X=F) | 4700 (±420)[a] | 10400 (±890)[a] | 1600 (±190)[a] | 470 (±50)[a] |
| 8h ($R_1$=$^i$Pr, $R_2$=H, $R_3$=H, $R_4$=Et, X=Cl) | 26900 (±1960)[a] | 16600 (±1540)[a] | 4800 (±520)[a] | 2430 (±270)[a] |
| 8i ($R_1$=H, $R_2$=OMe, $R_3$=H, $R_4$=Et, X=F) | 80210 (±9130)[a] | 23790 (±2830)[a] | 9170 (±1030)[a] | 750 (±95)[a] |
| 8j ($R_1$=H, $R_2$=OMe, $R_3$=H, $R_4$=Et, X=Cl) | 91900 (±5230)[a] | 43180 (±5180)[a] | 18790 (±2050)[a] | 18450 (±1750)[a] |
| 8k ($R_1$=Me, $R_2$=OMe, $R_3$=H, $R_4$=Et, X=F) | 70760 (±18200)[a] | 365400 (±84900)[c] | 4320 (±520)[a] | 4300 (±410)[b] |
| 8l ($R_1$=Me, $R_2$=OMe, $R_3$=H, $R_4$=Et, X=Cl) | 57800 (±5550)[a] | 74660 (±12330)[a] | 14840 (±1620)[a] | 19400 (±2100)[a] |
| 8m ($R_1$=Me, $R_2$=OEt, $R_3$=H, $R_4$=Et, X=F) | 29800 (±3140)[a] | 85600 (±7950)[a] | 3470 (±210)[a] | 3350 (±150)[a] |
| 8n ($R_1$=Me, $R_2$=OEt, $R_3$=H, $R_4$=Et, X=Cl) | 18100 (±1930)[a] | 65170 (±13200)[a] | 8280 (±910)[a] | 1510 (±80)[a] |
| 8o ($R_1$=Me, $R_2$=H, $R_3$=OMe, $R_4$=Et, X=F) | 50500 (±6120)[a] | 133700 (±19800)[d] | 1070 (±120)[a] | 4100 (±330)[a] |
| 8p ($R_1$=Me, $R_2$=H, $R_3$=OMe, $R_4$=Et, X=Cl) | 71100 (±14200)[a] | 61500 (±7800)[a] | 17750 (±1630)[a] | 1900 (±170)[a] |
| 8q ($R_1$=Me, $R_2$=OMe, $R_3$=H, $R_4$=Pr, X=F) | 51470 (±9100)[a] | 93300 (±10760)[a] | 1600 (±370)[a] | 4200 (±470)[a] |
| 8r ($R_1$=Me, $R_2$=OMe, $R_3$=H, $R_4$=Pr, X=Cl) | 43920 (±3300)[a] | 51200 (±8260)[a] | 14480 (±3140)[a] | 12400 (±1520)[a] |
| 8s ($R_1$=Me, $R_2$=OMe, $R_3$=H, $R_4$=cyclopropyl, X=F) | 45970 (±7300)[a] | 94320 (±14860)[a] | 1220 (±280)[a] | 4500 (±920)[a] |
| 8t ($R_1$=Me, $R_2$=OMe, $R_3$=H, $R_4$=cyclopropyl, X=Cl) | 40440 (±1750)[a] | 57500 (±7500)[a] | 9480 (±1720)[a] | 8580 (±3320)[a] |
| 8u ($R_1$=Et, $R_2$=OMe, $R_3$=H, $R_4$=Et, X=F) | 39100 (±4210)[a] | 55980 (±11400)[a] | 1400 (±130)[a] | 2800 (±190)[a] |
| 8v ($R_1$=Et, $R_2$=OMe, $R_3$=H, $R_4$=Et, X=Cl) | 54400 (±4180)[a] | 46570 (±3540)[a] | 5970 (±460)[a] | 1750 (±220)[a] |
| 8w ($R_1$=H, $R_2$=H, $R_3$=OMe, $R_4$=Et, X=F) | 9360 (±1020)[a] | 13540 (±1890)[a] | 7630 (±810)[a] | 2140 (±190)[a] |
| 8x ($R_1$=H, $R_2$=H, $R_3$=OMe, $R_4$=Et, X=Cl) | 30270 (±5660)[a] | 35400 (±4280)[a] | 16000 (±1890)[a] | 3890 (±420)[a] |
| 8y ($R_1$=Et, $R_2$=H, $R_3$=OMe, $R_4$=Et, X=F) | 15170 (±2130)[a] | 37780 (±4250)[a] | 1480 (±130)[a] | 540 (±110)[a] |
| 8z ($R_1$=Et, $R_2$=H, $R_3$=OMe, $R_4$=Et, X=Cl) | 30070 (±3190)[a] | 38210 (±4310)[a] | 11850 (±1540)[a] | 1410 (±120)[a] |
| 8a' ($R_1$=Me, $R_2$=OMe, $R_3$=H, $R_4$=Me, X=F) | 59760 (±6130)[a] | 212700 (±57650)[f] | 2010 (±180)[a] | 2300 (±410)[b] |
| 8b' ($R_1$=Me, $R_2$=OMe, $R_3$=H, $R_4$=Me, X=F) | 43150 (±5100)[a] | 69880 (±6430)[a] | 13650 (±1410)[a] | 6340 (±820)[a] |

[a] A single $k_{obs}$ was determined.
[b] $k_{inact}/K_I$ was determined from a linear fit.
[c] $k_{inact}$ = 1.94 min$^{-1}$, $K_I$ = 5.3 μM.
[d] $k_{inact}$ = 2.50 min$^{-1}$, $K_I$ = 18.7 μM.
[e] $k_{inact}$ = 1.31 min$^{-1}$, $K_I$ = 23.4 μM.
[f] $k_{inact}$ = 2.73 min$^{-1}$, $K_I$ = 12.8 μM.

TABLE 4b

Summary of isozyme selectivity for compounds 8a-b'

| Compound | Fold PAD1 Selectivity | Fold PAD2 Selectivity | Fold PAD3 Selectivity | Fold PAD4 Selectivity |
|---|---|---|---|---|
| 8a ($R_1$=H, $R_2$=H, $R_3$=H, $R_4$=Et, X=F) | 3.4 | 1.0 | 1.0 | 1.0 |
| 8b ($R_1$=H, $R_2$=H, $R_3$=H, $R_4$=Et, X=Cl) | 4.3 | 1.5 | 1.0 | 1.4 |
| 8c ($R_1$=Me, $R_2$=H, $R_3$=H, $R_4$=Et, X=F) | 6.1 | 11 | 1.9 | 1.0 |
| 8d ($R_1$=Me, $R_2$=H, $R_3$=H, $R_4$=Et, X=Cl) | 21 | 19 | 1.0 | 1.2 |
| 8e ($R_1$=Et, $R_2$=H, $R_3$=H, $R_4$=Et, X=F) | 19 | 33 | 1.0 | 1.0 |
| 8f ($R_1$=Et, $R_2$=H, $R_3$=H, $R_4$=Et, X=Cl) | 18 | 14 | 2.1 | 1.0 |
| 8g ($R_1$=$^i$Pr, $R_2$=H, $R_3$=H, $R_4$=Et, X=F) | 10 | 22 | 3.4 | 1.0 |
| 8h ($R_1$=$^i$Pr, $R_2$=H, $R_3$=H, $R_4$=Et, X=Cl) | 11 | 6.8 | 2.0 | 1.0 |
| 8i ($R_1$=H, $R_2$=OMe, $R_3$=H, $R_4$=Et, X=F) | 107 | 32 | 12 | 1.0 |
| 8j ($R_1$=H, $R_2$=OMe, $R_3$=H, $R_4$=Et, X=Cl) | 5.0 | 2.3 | 1.0 | 1.0 |
| 8k ($R_1$=Me, $R_2$=OMe, $R_3$=H, $R_4$=Et, X=F) | 16 | 85 | 1.0 | 1.0 |
| 8l ($R_1$=Me, $R_2$=OMe, $R_3$=H, $R_4$=Et, X=Cl) | 3.9 | 5.0 | 1.0 | 1.3 |
| 8m ($R_1$=Me, $R_2$=OEt, $R_3$=H, $R_4$=Et, X=F) | 8.9 | 26 | 1.0 | 1.0 |
| 8n ($R_1$=Me, $R_2$=OEt, $R_3$=H, $R_4$=Et, X=Cl) | 12 | 43 | 5.5 | 1.0 |
| 8o ($R_1$=Me, $R_2$=H, $R_3$=OMe, $R_4$=Et, X=F) | 47 | 125 | 1.0 | 3.8 |
| 8p ($R_1$=Me, $R_2$=H, $R_3$=OMe, $R_4$=Et, X=Cl) | 37 | 32 | 9.3 | 1.0 |
| 8q ($R_1$=Me, $R_2$=OMe, $R_3$=H, $R_4$=$^i$Pr, X=F) | 32 | 58 | 1.0 | 2.6 |
| 8r ($R_1$=Me, $R_2$=OMe, $R_3$=H, $R_4$=$^i$Pr, X=Cl) | 3.5 | 4.1 | 1.2 | 1.0 |
| 8s ($R_1$=Me, $R_2$=OMe, $R_3$=H, $R_4$=cyclopropyl, X=F) | 38 | 77 | 1.0 | 3.8 |
| 8t ($R_1$=Me, $R_2$=OMe, $R_3$=H, $R_4$=cyclopropyl, X=Cl) | 4.7 | 6.7 | 1.1 | 1.0 |
| 8u ($R_1$=Et, $R_2$=OMe, $R_3$=H, $R_4$=Et, X=F) | 28 | 40 | 2.0 | 1.0 |
| 8v ($R_1$=Et, $R_2$=OMe, $R_3$=H, $R_4$=Et, X=Cl) | 31 | 27 | 3.4 | 1.0 |
| 8w ($R_1$=H, $R_2$=H, $R_3$=OMe, $R_4$=Et, X=F) | 4.4 | 6.3 | 3.6 | 1.0 |
| 8x ($R_1$=H, $R_2$=H, $R_3$=OMe, $R_4$=Et, X=Cl) | 7.8 | 9.1 | 4.1 | 1.0 |
| 8y ($R_1$=Et, $R_2$=H, $R_3$=OMe, $R_4$=Et, X=F) | 28 | 70 | 2.7 | 1.0 |
| 8z ($R_1$=Et, $R_2$=H, $R_3$=OMe, $R_4$=Et, X=Cl) | 21 | 27 | 8.4 | 1.0 |
| 8a' ($R_1$=Me, $R_2$=OMe, $R_3$=H, $R_4$=Me, X=F) | 30 | 106 | 1.0 | 1.1 |
| 8b' ($R_1$=Me, $R_2$=OMe, $R_3$=H, $R_4$=Me, X=F) | 6.8 | 11 | 2.2 | 1.0 |

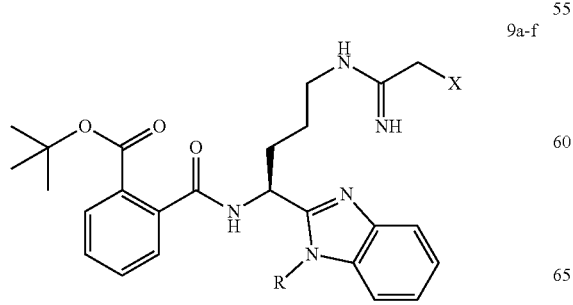

9a-f

TABLE 5a $k_{inact}/K_I$ values for compounds 9a-f

| Compound | PAD1 $k_{inact}/K_I$ (M$^{-1}$min$^{-1}$) | PAD2 $k_{inact}/K_I$ (M$^{-1}$min$^{-1}$) | PAD3 $k_{inact}/K_I$ (M$^{-1}$min$^{-1}$) | PAD4 $k_{inact}/K_I$ (M$^{-1}$min$^{-1}$) |
|---|---|---|---|---|
| 9a (R=Me, X=F) | 2470 (±270)[a] | 2400 (±220)[b] | 1200 (±90)[a] | 2430 (±370)[b] |
| 9b (R=Me, X=Cl) | 19500 (±2200)[a] | 3310 (±250)[b] | 5200 (±710)[a] | 3850 (±410)[b] |
| 9c (R=Et, X=F) | 950 (±70)[a] | 6100 (±760)[b] | 3100 (±440)[a] | 440 (±90)[b] |
| 9d (R=Et, X=Cl) | 12030 (±1100)[a] | 9150 (±760)[a] | 4700 (±920)[a] | 1300 (±220)[b] |
| 9e (R=$^i$Pr, X=F) | 1420 (±210)[a] | 3010 (±290)[a] | 2100 (±190)[a] | 160 (±80)[a] |
| 9f (R=$^i$Pr, X=Cl) | 3360 (±520)[a] | 7150 (±990)[a] | 4800 (±520)[a] | 680 (±110)[a] |

[a] A single $k_{obs}$ was determined.
[b] $k_{inact}/K_I$ was determined from a linear fit.

TABLE 5b

Summary of isozyme selectivity for compounds 9a-f

| Compound | Fold PAD1 Selectivity | Fold PAD2 Selectivity | Fold PAD3 Selectivity | Fold PAD4 Selectivity |
|---|---|---|---|---|
| 9a (R=Me, X=F) | 2.1 | 2.0 | 1.0 | 2.0 |
| 9b (R=Me, X=Cl) | 5.9 | 1.0 | 1.6 | 1.2 |
| 9c (R=Et, X=F) | 2.2 | 14 | 7.0 | 1.0 |
| 9d (R=Et, X=Cl) | 9.3 | 7.0 | 3.6 | 1.0 |
| 9e (R=$^i$Pr, X=F) | 8.9 | 19 | 13 | 1.0 |
| 9f (R=$^i$Pr, X=Cl) | 4.9 | 11 | 7.1 | 1.0 |

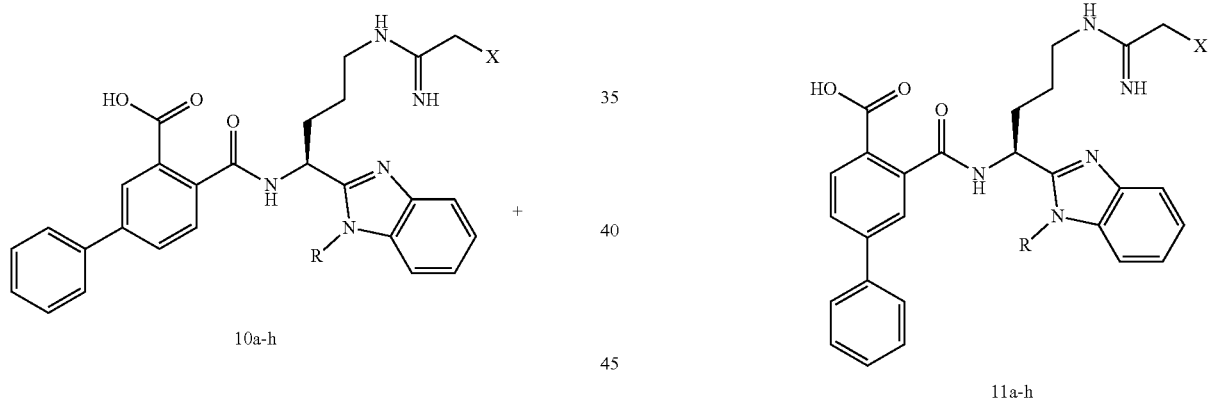

10a-h

-continued 11a-h

TABLE 6a $k_{inact}/K_I$ values for compounds 10a-h and 11a-h

| Compound | PAD1 $k_{inact}/K_I$ (M$^{-1}$min$^{-1}$) | PAD2 $k_{inact}/K_I$ (M$^{-1}$min$^{-1}$) | PAD3 $k_{inact}/K_I$ (M$^{-1}$min$^{-1}$) | PAD4 $k_{inact}/K_I$ (M$^{-1}$min$^{-1}$) |
|---|---|---|---|---|
| 10a + 11a (R=H, X=F) | 12600 (±1450)[a] | 10400 (±930)[b] | 20030 (±1980)[a] | 27300 (±2910)[b] |
| 10b + 11b (R=H, X=Cl) | 57300 (±9800)[a] | 34300 (±4200)[b] | 32800 (±2890)[a] | 41400 (±3800)[b] |
| 10c + 11c (R=Me, X=F) | 28850 (±2760)[a] | 27700 (±3100)[a] | 29800 (±1980)[a] | 3250 (±670)[a] |
| 10d + 11d (R=Me, X=Cl) | 65800 (±9500)[a] | 63800 (±9800)[a] | 44100 (±8200)[a] | 14400 (±4200)[a] |
| 10e + 11e (R=Et, X=F) | 29900 (±3400)[a] | 43300 (±3500)[a] | 9500 (±1020)[a] | 1930 (±180)[a] |
| 10f + 11f (R=Et, X=Cl) | 71600 (±8700)[a] | 78300 (±6400)[a] | 30100 (±2870)[a] | 32090 (±3050)[a] |
| 10g + 11g (R=$^i$Pr, X=F) | 10050 (±1100)[a] | 13600 (±1200)[a] | 10300 (±960)[a] | 380 (±50)[a] |
| 10h + 11h (R=$^i$Pr, X=Cl) | 57300 (±4070)[a] | 26900 (±2900)[b] | 7100 (±830)[a] | 3700 (±320)[b] |

[a] A single $k_{obs}$ was determined.
[b] $k_{inact}/K_I$ was determined from a linear fit.

TABLE 6b

Summary of isozyme selectivity for compounds 10a-h and 11a-h

| Compound | Fold PAD1 Selectivity | Fold PAD2 Selectivity | Fold PAD3 Selectivity | Fold PAD4 Selectivity |
|---|---|---|---|---|
| 10a + 11a (R=H, X=F) | 1.2 | 1.0 | 1.9 | 2.6 |
| 10b + 11b (R=H, X=Cl) | 1.7 | 1.0 | 1.0 | 1.3 |
| 10c + 11c (R=Me, X=F) | 8.9 | 8.5 | 9.2 | 1.0 |
| 10d + 11d (R=Me, X=Cl) | 4.6 | 4.4 | 3.1 | 1.0 |
| 10e + 11e (R=Et, X=F) | 15 | 22 | 4.9 | 1.0 |
| 10f + 11f (R=Et, X=Cl) | 2.4 | 2.6 | 1.0 | 1.1 |
| 10g + 11g (R=$^i$Pr, X=F) | 26 | 36 | 27 | 1.0 |
| 10h + 11h (R=$^i$Pr, X=Cl) | 15 | 7.3 | 1.9 | 1.0 |

FIG. 1 shows exemplary concentration dependent labeling of recombinant PAD2 with BB-F-Yne (5u) (FIG. 1A) and with BB-Cl-Yne (5v) (FIG. 1C) and the limit of detection (LOD) of BB-F-Yne (5u) and of BB-Cl-Yne (5v) for PAD2, (FIG. 1B) and (FIG. 1D), respectively. Decreasing concentrations of PAD2 treated with BB-F-Yne (5u) and "Clicked" with TAMRA-N$_3$. Decreasing concentrations of PAD2 were treated with BB-Cl-Yne (5v) and "Clicked" with TAMRA-N$_3$.

Figure 2:
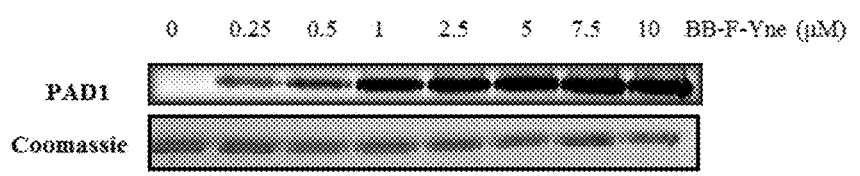
FIG. 2. In vitro labeling of the four active PAD isozymes with BB-F-Yne (5u). (A) Concentration dependent labeling of recombinant PAD1 with BB-F-Yne (5u). PAD1 was treated with increasing concentrations of BB-F-Yne (5u) and then "Clicked" with TAMRA-$N_3$. (B) Concentration dependent labeling of recombinant PAD2 with BB-F-Yne (5u). PAD2 was treated with increasing concentrations of BB-F-Yne (5u) and then "Clicked" with TAMRA-$N_3$. This data can also be seen in FIG. 1 and is repeated here for clarity. (C) Concentration dependent labeling of recombinant PAD3 with BB-F-Yne (5u). PAD3 was treated with increasing concentrations of BB-F-Yne (5u) and then "Clicked" with TAMRA-$N_3$. (D) Concentration dependent labeling of recombinant PAD4 with BB-F-Yne (5u). PAD4 was treated with increasing concentrations of BB-F-Yne (5u) and then "Clicked" with TAMRA-$N_3$.
Figure 2:
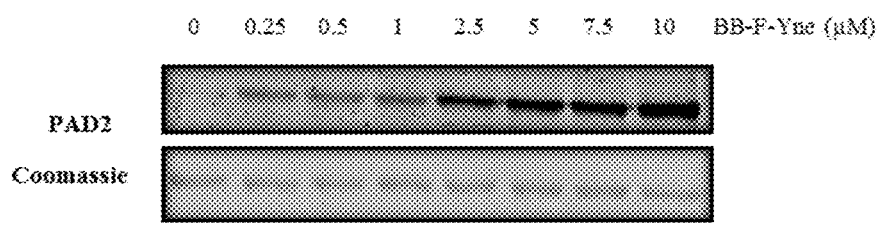
Figure 2:
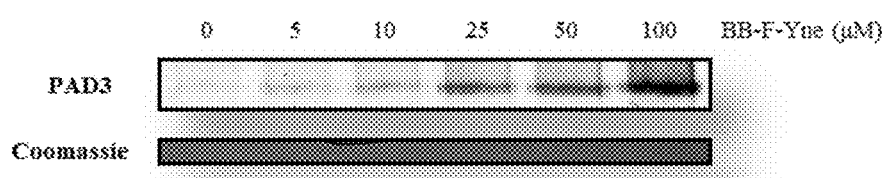
Figure 2:
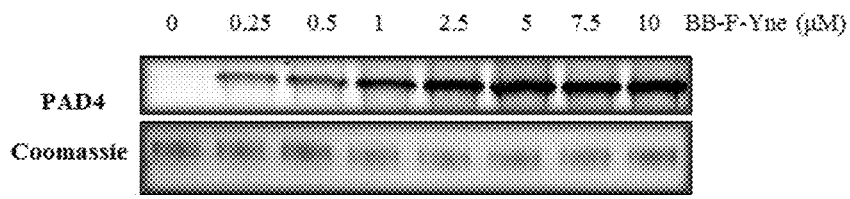

FIG. 2 shows exemplary in vitro labeling of the four active PAD isozymes with BB-F-Yne (5u). FIG. 2A shows concentration dependent labeling of recombinant PAD1 with BB-F-Yne (5u). PAD1 was treated with increasing concentrations of BB-F-Yne (5u) and then "Clicked" with TAMRA-N$_3$. FIG. 2B shows concentration Concentration dependent labeling of recombinant PAD2 with BB-F-Yne (5u). PAD2 was treated with increasing concentrations of BB-F-Yne (5u) and then "Clicked" with TAMRA-N$_3$. FIG. 2C shows concentration dependent labeling of recombinant PAD3 with BB-F-Yne (5u). PAD3 was treated with increasing concentrations of BB-F-Yne (5u) and then "Clicked" with TAMRA-N$_3$. FIG. 2D shows concentration dependent labeling of recombinant PAD4 with BB-F-Yne (5u). PAD4 was treated with increasing concentrations of BB-F-Yne (5u) and then "Clicked" with TAMRA-N$_3$.

Figure 3:
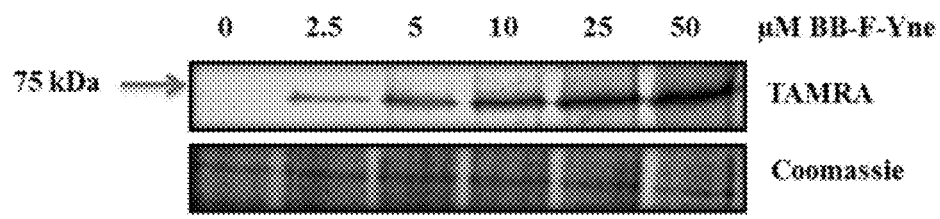
FIG. 3. Cellular labeling of PAD2 with BB-F-Yne (5u) in ionophore stimulated HEK293T/PAD2 cells. (A) HEK293T/PAD2 cells were treated with increasing concentrations of BB-F-Yne (5u) for 1 h. The cells were then harvested and probe labeled proteins were tagged with TAMRA-$N_3$ to facilitate visualization after SDS-PAGE. (B&C) HEK293T/PAD2 cells were treated with increasing concentrations of BB-F-Yne (5u) for 1 h. The cells were then harvested and probe labeled proteins were tagged with Biotin-TEV-$N_3$. Biotin tagged proteins were then isolated on streptavidin agarose and the eluted proteins were probed for PAD2 (panel B) or biotinylated proteins using streptavidin-HRP (panel C).
Figure 3:
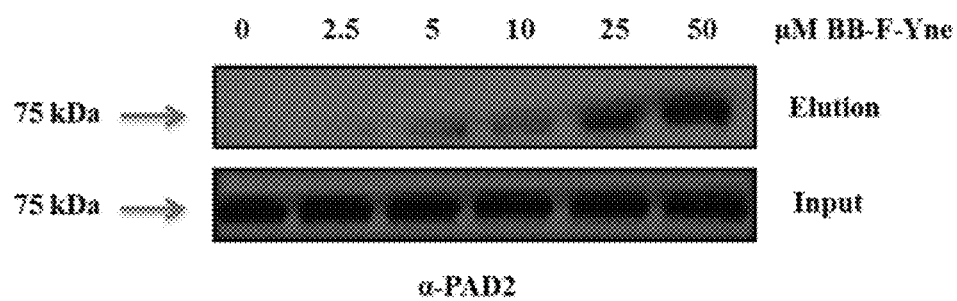
Figure 3:
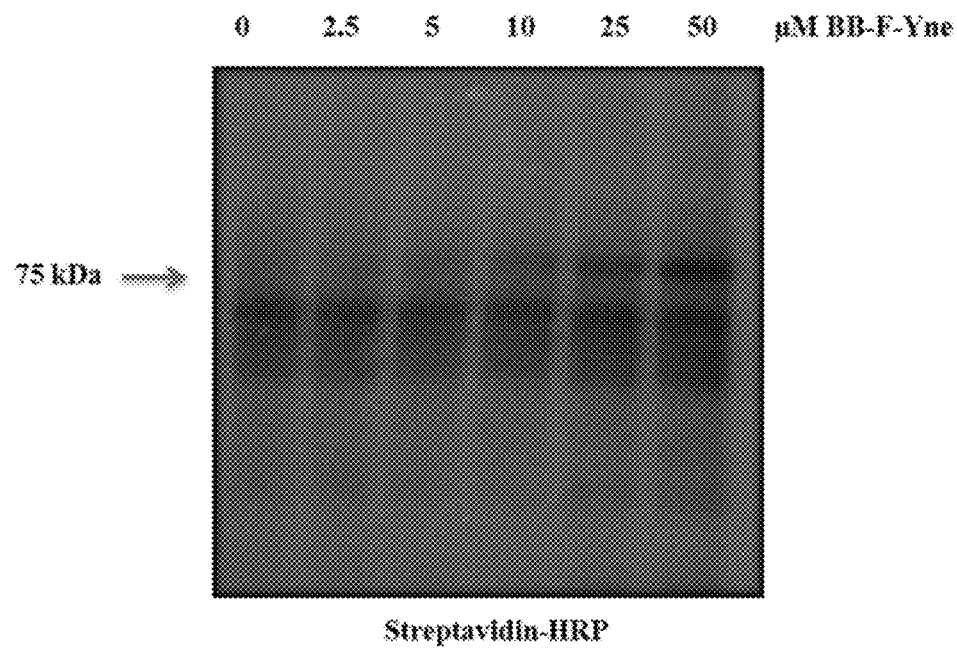

FIG. 3 shows exemplary cellular labeling of PAD2 with BB-F-Yne (5u) in ionophore stimulated HEK293T/PAD2 cells. FIG. 3A shows HEK293T/PAD2 cells treated with increasing concentrations of BB-F-Yne (5u) for 1 h. The cells were then harvested and probe labeled proteins were tagged with TAMRA-N$_3$ to facilitate visualization after SDS-PAGE. (B&C) HEK293T/PAD2 cells were treated with increasing concentrations of BB-F-Yne (5u) for 1 h. The cells were then harvested and probe labeled proteins were tagged with Biotin-TEV-N$_3$. Biotin tagged proteins were then isolated on streptavidin agarose and the eluted proteins were probed for PAD2 (FIG. 3B) or biotinylated proteins using streptavidin-RP (FIG. 3C).

Figure 4:
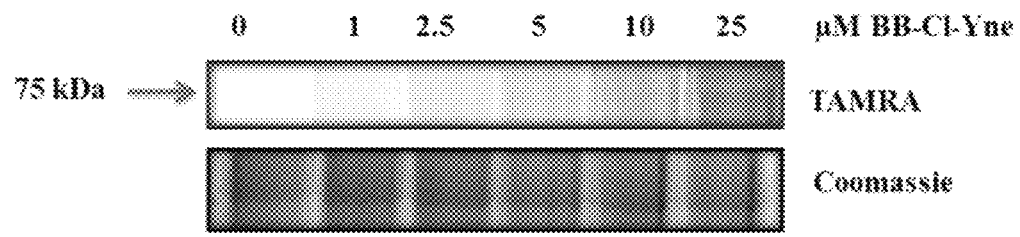
FIG. 4. Cellular labeling of PAD2 with BB-C-Yne (5v) in ionophore stimulated HEK293T/PAD2 cells. (A) HEK293T/PAD2 cells were treated with increasing concentrations of BB-C-Yne (5) for 1 h. The cells were then harvested and probe labeled proteins were tagged with TAMRA-$N_3$ to facilitate visualization after SDS-PAGE. (B&C) HEK293T/PAD2 cells were treated with increasing concentrations of BB-C-Yne (5v) for 1 h. The cells were then harvested and probe labeled proteins were tagged with Biotin-TEV-$N_3$. Biotin tagged proteins were then isolated on streptavidin agarose and the eluted proteins were probed for PAD2 (panel B) or biotinylated proteins using streptavidin-HRP (panel C).
Figure 4:
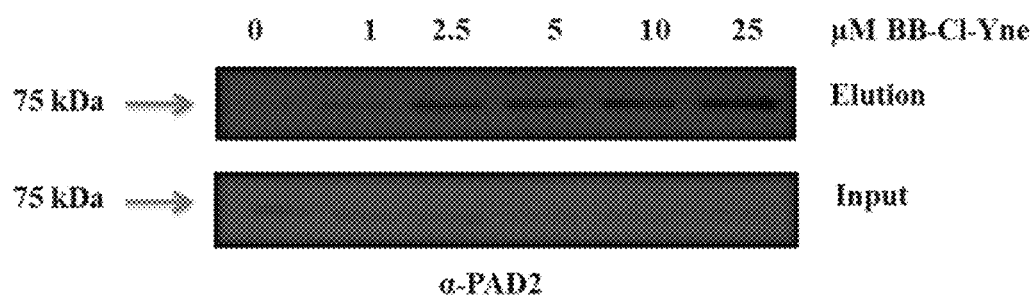
Figure 4:
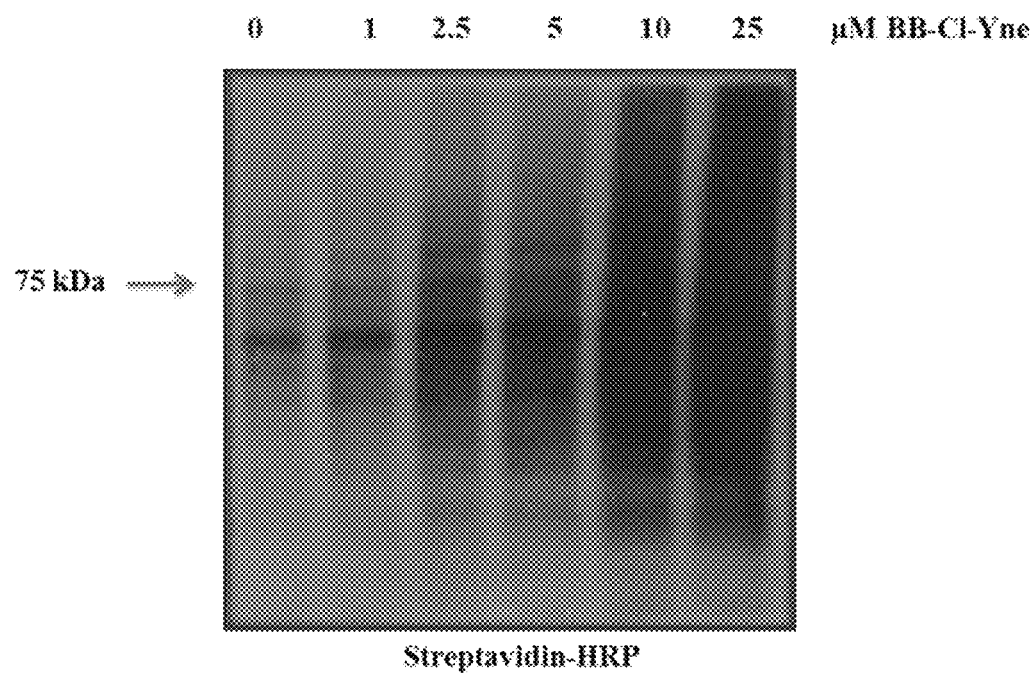

FIG. 4 shows exemplary cellular labeling of PAD2 with BB-C-Yne (5v) in ionophore stimulated HEK293T/PAD2 cells. FIG. 4A shows HEK293T/PAD2 cells treated with increasing concentrations of BB-C-Yne (5v) for 1 h. The cells were then harvested and probe labeled proteins were tagged with TAMRA-N$_3$ to facilitate visualization after SDS-PAGE. FIG. 4B-4C show HEK293T/PAD2 cells treated with increasing concentrations of BB-C-Yne (5v) for 1 h. The cells were then harvested and probe labeled proteins were tagged with Biotin-TEV-N$_3$. Biotin tagged proteins were then isolated on streptavidin agarose and the eluted proteins were probed for PAD2 (FIG. 4B) or biotinylated proteins using streptavidin-RP (FIG. 4C).

Figure 5:
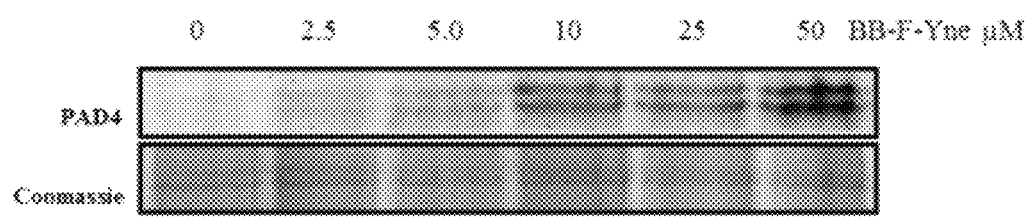
FIG. 5. Cellular labeling of PAD4 with BB-F-Yne (5u). (A) HEK293T/PAD4 cells were treated with increasing concentrations of BB-F-Yne (5u) for 1 h. The cells were then harvested and probe labeled proteins were tagged with TAMRA-$N_3$ to facilitate visualization after SDS-PAGE. (B) HEK293T/PAD4 cells were treated with increasing concentrations of BB-F-Yne (5u) for 1 h. The cells were then harvested and probe labeled proteins were tagged with Biotin-TEV-$N_3$. Biotin tagged proteins were then isolated on streptavidin agarose and the eluted proteins were probed for PAD2.
Figure 5:
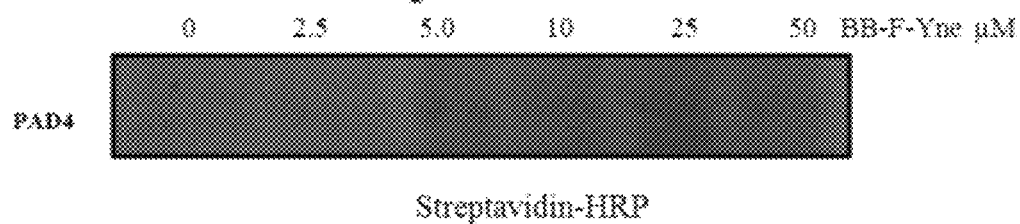

FIG. 5 shows exemplary cellular labeling of PAD4 with BB-F-Yne (5u). FIG. 5A shows HEK293T/PAD4 cells were treated with increasing concentrations of BB-F-Yne (5u) for 1 h. The cells were then harvested and probe labeled proteins were tagged with TAMRA-N$_3$ to facilitate visualization after SDS-PAGE. FIG. 5B shows HEK293T/PAD4 cells treated with increasing concentrations of BB-F-Yne (5u) for 1 h. The cells were then harvested and probe labeled proteins were tagged with Biotin-TEV-N$_3$. Biotin tagged proteins were then isolated on streptavidin agarose and the eluted proteins were probed for PAD2.

Experimental

Chemistry $^1$H NMR were recorded at 400 (Bruker DRX-400 with a H/C/P/F QNP gradient probe) or 500 MHz (Bruker BioSpin 500 MHz Advance III Digital NMR) spectrometer and $^{13}$C NMR spectra were recorded at 100 or 125 MHz; chemical shifts are reported in δ (ppm) relative to the internal chloroform-d (CDCl$_3$, 7.26 ppm) or methanol-d (CD$_3$OD, 3.31 ppm). ESI (HRMS) were recorded with a Micromass Q-TQF I. The purity of all compounds was determined to be >95% purity as determined by $^1$H NMR and $^{13}$C NMR spectra, unless otherwise noted. TLC was performed on glass backed silica gel plates (Uniplate) with spots visualized by UV light. All solvents were reagent grade and, when necessary, were purified and dried by standard methods. Concentrations of solutions after reactions and extractions involved the use of a rotary evaporator operating at reduced pressure.

Chemicals and Proteins

Dithiothreitol (DTT), 4-(2-hydroxyethyl)-1-piperazineethanesulfonic acid (HEPES), ammonium iron (III) sulfate dodecahydrate, tris(2-carboxyethyl)phosphine (TCEP), and thiosemicarbazide were acquired from Sigma-Aldrich. Diacetylmonooxime (DAMO), N-α-benzoyl-L-arginine ethyl ester (BAEE), and N-α-benzoyl-L-arginine amide (BAA) were obtained from Acros. Detailed synthetic procedures are described below. PADs 1, 2, 3, and 4 were purified as reported. (Causey, et al. 2011 *J Med Chem* 54, 6919-6935; Knuckley, et al. 2010 *Biochemistry* 49, 4852-4863.) HEK293T and HEK293T cells stably expressing human PAD2 (HEK293T/PAD2) or PAD4 (HEK293T/PAD4) were cultured as previously described. (Lewallen, et al. 2014 *ACS Chem Biol* 9, 913-921.) Biotin-TEV-N$_3$ was synthesized as previously reported. (Weerapana, et al., 2007 *Nat Protoc* 2, 1414-1425.) TAMRA-N$_3$ was obtained from Lumiprobe.

Inactivation Kinetics

Inactivation kinetic parameters were determined by incubating PAD1, 2, or 4 (2.0 µM) or PAD3 (5.0 µM) in a pre-warmed (10 min; 37° C.) inactivation mixture (50 mM HEPES, 10 mM CaCl₂, and 2 mM DTT, pH 7.6, with a final volume of 60 µL) containing various concentrations of inhibitor. Aliquots were removed at various time points and added to a pre-warmed (10 min, 37° C.) reaction mixture (50 mM HEPES, 50 mM NaCl, 10 mM CaC₂, 2 mM DTT, and 10 mM BAEE or 10 mM BAA in the case of PAD3; pH 7.6). After 15 min, reactions were quenched in liquid nitrogen and citrulline production quantified using the COLDER assay. (Kearney, et al. 2005 Biochemistry 44, 10570-10582; Knipp, et al. 2000 *Anal Biochem* 286, 257-264.) Data were plotted as a function of time and fit to eq 1, $$v = v_o e^{-kt} \qquad \text{eq 1,}$$

using GraFit version 5.0.11, where v is velocity, $v_o$ is initial velocity, k (or $k_{obs}$) is the pseudo-first order rate constant of inactivation, and t is time. When saturation was reached upon plotting $k_{obs}$ versus inactivator concentration, the data were fit to eq 2, $$k_{obs} = k_{inact}[I]/(K_I + [I]) \qquad \text{eq 2,}$$

using GraFit version 5.0.11, where $k_{inact}$ corresponds to the maximal rate of inactivation and $K_I$ is the concentration of inhibitor that gives half-maximal inactivation. If the plot of $k_{obs}$ versus [I] was linear and did not saturate, then the value for $k_{inact}/K_I$ equaled the slope of the line.

In Vitro Labeling of PADs with "Clickable" Probes BB-F-Yne (5u), BB-Cl-Yne (5v) and BIFYne (5w)

Increasing concentrations of 5u-w (0 to 10 µM) were incubated with recombinant PADs (1 µM) in the presence of CaCl₂ in 1×PBS (2 mM) at 37° C. for 1 h. The probe labeled enzymes were coupled to TAMRA-N₃ (20 µM) in the presence of 1×TBTA (0.31 mM), sodium ascorbate (2 mM) and freshly prepared CuSO₄ (1 mM). The tubes were gently tumbled for 1 h. The reactions were quenched with 6×SDS loading buffer and separated by SDS-PAGE (12.5% gel). The bands were visualized by scanning the gel in a typhoon scanner (approximate excitation/emission maxima 546/579, respectively).

In Vitro Labeling o f PAD2 with BB-F-Yne (5u) and BB-C-Yne (5v) to Determine their Limit of detection (LOD)

BB-F-Yne (5u) or BB-Cl-Yne (5v) (10 µM) were incubated with decreasing concentrations of recombinant PAD2 (1.0 to 0.025 µM) in the presence of CaCl₂ in 1×PBS (2 mM) at 37° C. for 1 h. The probe labeled enzymes were coupled to TAMRA-N₃ (20 µM) in the presence of 1×TBTA (0.31 mM), sodium ascorbate (2 mM) and freshly prepared CuSO₄ (1 mM). The tubes were gently tumbled for 1 h. The reactions were quenched with 6×SDS loading buffer and separated by SDS-PAGE (12.5% gel). The bands were visualized by scanning the gel in a typhoon scanner (approximate excitation/emission maxima 546/579, respectively).

Cellular Labeling of PAD2 with BB-F-Yne (5u) and BB-Cl-Yne (5v) in Ionomycin Stimulated HEK293T/PAD2 Cells HEK293T cells stably expressing human PAD2 (HEK293T PAD2) were cultured. Cells were grown to ~80% confluence (8×10⁶ cells), trypsinized, and quenched trypsin activity with complete media. The cells were harvested by centrifugation at 1000×g for 2 min and washed 4× with 1×PBS. Cells were resuspended in PBS at 8×10⁶ cells/mL and 4×105 cells were added to 0.65 mL tubes for subsequent assays.

HEK293T PAD2 cells were treated with increasing concentrations of BB-F-Yne (5u) or BB-Cl-Yne (5v) (0 to 50 µM) in the presence of CaCl₂ (2 mM) at 37° C. After 20 min, ionomycin (10 µM) was added and the cells incubated for 1 h before addition of Triton X-100 (1% final in PBS) and sonication at 4° C. for 1 h. Lysates were cleared by centrifugation at 21,000×g for 15 min. The soluble protein fraction was isolated and quantified by the DC assay (Biorad). Lysates (2 µg/µL, 50 µL total) were "Clicked" with TAMRA-N₃ (20 µM), 1×TBTA (0.31 mM), sodium ascorbate (2 mM) and freshly prepared CuSO₄ (1 mM). The tubes were gently tumbled for 2 h. The reactions were quenched by the addition of 6×SDS loading buffer and separated by SDS-PAGE (12.5% gel). The bands were visualized by scanning the gel in a typhoon scanner (approximate excitation/emission maxima ~546/579, respectively).

Lysates (2 µg/µL, 500 µL total) were also "Clicked" with Bio-TEV-N₃ (100 µM), 1×TBTA (0.31 mM), sodium ascorbate (2 mM) and freshly prepared CuSO₄ (1 mM). The tubes were gently tumbled for 2 h. The cloudy solution was transferred to a microconcentrator (10 kDa molecular weight cutoff) and centrifuged at 10000×g for 5 min at 4° C. to remove the excess biotin azide. The protein was then resolubilized in 1×PBS with 0.2% SDS. Resolubilized protein samples were incubated with 100 µL streptavidin-agarose beads (Thermo Scientific) at 4° C. for 16 h. The solutions were then incubated at rt for 1 h. The beads were washed with 0.2% SDS/PBS, PBS, and water. The beads were pelleted by centrifugation (1,600×g, 3 min) between washes. To the washed beads, 2×SDS loading buffer was added and heated to 95° C. heat block for 15 min. The resolubilized protein was separated by SDS-PAGE (12.5% gel) and transferred to PVDF membranes (Biorad) at 80 V for 60 min. The membranes were analyzed for PAD2 and for biotinylated proteins.

1. General Procedure for Synthesis of Benzene-1,2-diamine Intermediates

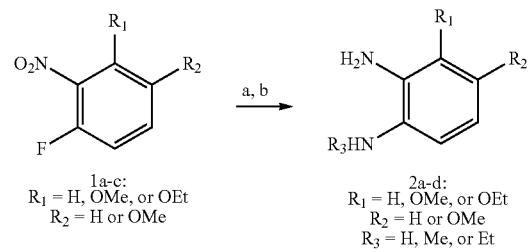

1a-c:
$R_1$ = H, OMe, or OEt
$R_2$ = H or OMe 2a-d:
$R_1$ = H, OMe, or OEt
$R_2$ = H or OMe
$R_3$ = H, Me, or Et

<sup>a</sup>Reagents: (a) NHR₃, DMF, 70° C.; (b) Na₂S₂O₄, THF/EtOH/H₂O

To a stirred solution of 1a-c (1.0 eq) in DMF was added NHR₃ (3.0 eq) in a sealed tube. The reaction mixture was then heated to 70° C. for 12 h, cooled, and diluted with water. The product was then filtered, washed with water, dried under vacuum, and obtained in 78-89% yield. This product was then dissolved in a THF/EtOH/H₂O (3:1:1) solvent system, and cooled to 0° C. A solution of Na₂S₂O₄ in water was then added dropwise to the stirred mixture. The reaction mixture was then warmed to rt and allowed to stir for 4 h. Upon completion, saturated NaHCO₃ solution was added followed by EtOAc extraction. The combined organic layers were then washed with deionized water. The organic layer was then separated, dried over anhydrous Na₂SO₄, filtered, and concentrated to give desired products 2a-d in 64-76% yield.

N¹-ethyl-3-methoxybenzene-1,2-diamine (2a)

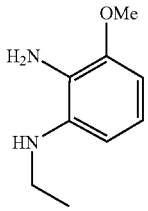

¹H NMR (CDC₃; 400 MHz): δ 6.78 (t, J=8.2 Hz, 1H), 6.41 (t, J=8.4 Hz, 2H), 3.85 (s, 3H), 3.19-3.14 (m, 2H), 1.30 (t, J=7.3 Hz, 3H). ¹³C NMR (CDCl₃; 100 MHz): δ 148.3, 138.6, 122.6, 119.6, 117.1, 111.8, 106.0, 105.3, 101.7, 55.8, 55.6, 43.6, 38.9, 15.1. LRMS m/z calculated for $C_9H_{14}N_2O$ (M+H⁺) 167.1; found 167.2.

3-ethoxy-N¹-methylbenzene-1,2-diamine (2b)

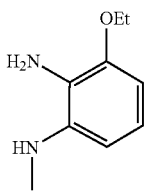

¹H NMR (CDC₃; 400 MHz): δ 6.78 (t, J=8.3 Hz, 1H), 6.43-6.37 (m, 2H), 4.09-4.03 (m, 2), 2.87 (s, 3H), 1.42 (t, J=7.4 Hz, 3H). ¹³C NMR (CDCl₃; 100 MHz): δ 147.4, 139.6, 122.9, 119.6, 104.4, 102.9, 64.1, 31.2, 15.1. LRMS m/z calculated for $C_9H_{14}N_2O$ (M+H⁺) 167.1; found 167.2.

4-methoxy-N¹-methylbenzene-1,2-diamine (2c)

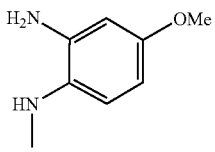

¹H NMR (CDC₃; 400 MHz): δ 6.89 (dd, J=2.2 Hz, J=8.7 Hz, 1H), 6.52 (d, J=8.2 Hz, 1H), 6.27-6.24 (m, 1H), 3.79 (s, 3H), 3.66 (s, 3H). ¹³C NMR (CDC₃; 100 MHz): δ 153.6, 143.6, 136.4, 132.1, 118.2, 113.2, 112.8, 109.6, 103.8, 103.2, 102.2, 55.5, 31.8, 31.0, 29.3. LRMS m/z calculated for $C_8H_{12}N_2O$ (M+H⁺) 152.1; found 152.2.

4-methoxy-N¹-ethylbenzene-1,2-diamine (2d)

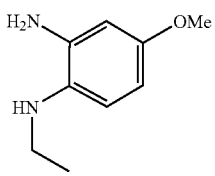

¹H NMR (CDC₃; 400 MHz): δ 7.10 (dd, J=2.3 Hz, J=8.2 Hz, 1H), 6.54 (d, J=8.2 Hz, 1H), 6.30-6.27 (m, 1H), 3.77 (s, 3H), 3.00 (m, 2H), 1.19 (t, 3H). ¹³C NMR (CDC₃; 100 MHz): δ 153.8, 137.1, 131.0, 118.3, 114.2, 111.5, 109.1, 104.1, 103.8, 103.1, 102.8, 101.7, 55.9, 55.5, 39.7, 38.5, 15.2, 14.9. LRMS m/z calculated for $C_9H_{14}N_2O$ (M+H⁺) 167.1; found 167.1.

2. General Procedure for Synthesis of Benzimidazole Intermediates

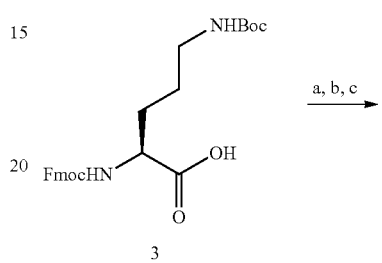

3

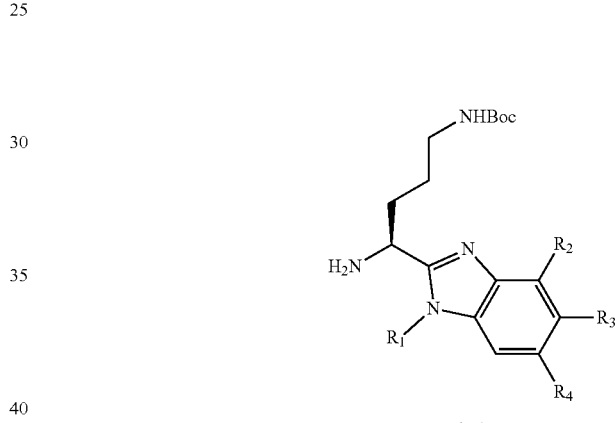

4a-l:
R₁ = H, Me, Et, or ⁱPr
R₂ = H, OMe, or OEt
R₃ = H, OMe or F
R₄ = H or F

ᵃReagents: (a) N¹R₁benzene-1,2-diamine, HOBt, HBTU, DIPEA, DMF; (b) AcOH/Toluene, 70° C.; (c) piperidine/DMF To a stirred solution of Fmoc-Orn(Boc)-OH (3, 1.0 eq) in DMF was added N¹R₁benzene-1,2-diamine (1.0 eq), DIPEA (3.0 eq), followed by HBTU (2.0 eq) and HOBt, (2.0 eq). This reaction mixture was stirred at rt under N₂ atmosphere for 12 h, and then diluted with water. The product was filtered, washed with water, and dried under vacuum, and obtained in 81-92% yield. This product was dissolved in glacial AcOH/toluene (1:1) and heated at 80° C. for 16 h. The reaction mixture was evaporated to dryness and diluted with water to precipitate the desired product (Fmoc-Orn (Boc)-benzimidazole) which was isolated by vacuum filtration in 84-96% yield. This compound was then treated with 20% piperidine in DMF for 20 min at rt to cleave the Fmoc group and the reaction was diluted with hexanes to remove the byproduct. The oily product was further purified by column chromatography using MeOH and CH₂Cl₂ as the eluent to give 4a-j in 45-56% yield.

tert-butyl-(4-amino-4-(1H-benzo[d]imidazol-2-yl)butyl)carbamate-L-ornithine (4a)

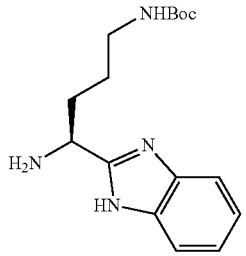 [SMILES: CC(C)(C)OC(=O)NCCC[C@H](N)c1nc2ccccc2[nH]1]

$^1$H NMR (CDCl$_3$; 400 MHz): δ 7.55-7.52 (m, 2H), 7.22-7.19 (m, 2H), 4.33 (t, J=6.7 Hz, 1H), 3.31-3.22 (m, 1H), 3.11-3.02 (m, 1H), 2.01-1.92 (m, 1H), 1.83-1.75 (m, 1H), 1.69-1.49 (m, 2H), 1.44 (s, 9H). $^{13}$C NMR (CDC$_3$; 100 MHz): δ 156.5, 122.1, 115.1, 79.5, 49.6, 39.5, 34.4, 28.3, 26.5. LRMS m/z calculated for C$_{16}$H$_{24}$N$_4$O$_2$ (M+H$^+$) 305.2; found 305.1.

tert-butyl-(4-amino-4-(1-methyl-benzo[d]imidazol-2-yl)butyl)carbamate-L-ornithine (4b)

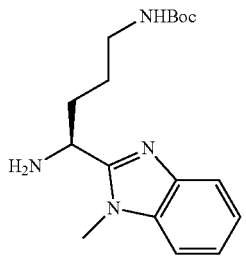 [SMILES: Cn1c([C@@H](N)CCCNC(=O)OC(C)(C)C)nc2ccccc21]

$^1$H NMR (CDC$_3$; 400 MHz): δ 7.73 (dd, J=2.6 Hz, 6.7 Hz, 1H), 7.33-7.29 (m, 1H), 7.28-7.25 (m, 2H), 4.28 (t, J=6.8 Hz, 1H), 3.79 (s, 3H), 3.18-3.13 (m, 2H), 2.10-2.01 (m, 1H), 1.94-1.83 (m, 1H), 1.71-1.53 (m, 2H), 1.41 (s, 9H). $^{13}$C NMR (CDCl$_3$; 100 MHz): δ 149.6, 145.2, 139.2, 127.0, 126.1, 122.6, 113.6, 100.0, 51.5, 43.8, 37.7, 33.7, 32.1, 29.8. LRMS m/z calculated for C$_{17}$H$_{26}$N$_4$O$_2$ (M+H$^+$) 319.2; found 319.2.

tert-butyl-(4-amino-4-(1-ethyl-benzo[d]imidazol-2-yl)butyl)carbamate-L-ornithine (4c)

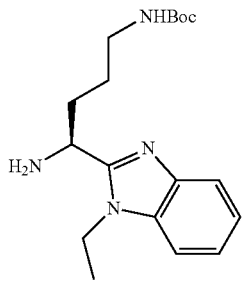 [SMILES: CCn1c([C@@H](N)CCCNC(=O)OC(C)(C)C)nc2ccccc21]

$^1$H NMR (CDCl$_3$; 400 MHz): δ 7.67 (dd, J=2.2 Hz, J=7.2 Hz, 1H), 7.32-7.30 (m, 1H), 7.24-7.19 (m, 2H), 4.27-4.22 (m, 1H), 4.21-4.12 (m, 2H), 3.10-3.07 (m, 2H), 2.05-1.96 (m, 1H), 1.91-1.82 (m, 1H), 1.64-1.46 (m, 2H), 1.37 (m, 12H). $^{13}$C NMR (CDCl$_3$; 100 MHz): δ 156.2, 155.9, 141.8, 134.3, 122.7, 122.0, 119.3, 109.5, 79.0, 48.1, 39.9, 38.5, 34.2, 28.3, 26.3, 15.1. LRMS m/z calculated for C$_{18}$H$_{28}$N$_4$O$_2$ (M+H$^+$) 333.2; found 333.3.

tert-butyl-(4-amino-4-(1-isopropyl-benzo[d]imidazol-2-yl)butyl)carbamate-L-ornithine (4d)

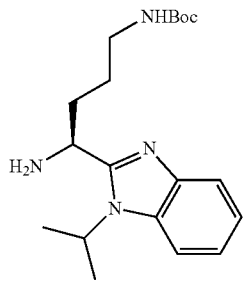 [SMILES: CC(C)n1c([C@@H](N)CCCNC(=O)OC(C)(C)C)nc2ccccc21]

$^1$H NMR (CDCl$_3$; 400 MHz): δ 7.71 (dd, J=2.4 Hz, 7.3 Hz, 1H), 7.52 (dd, J=2.1 Hz, J=6.3 Hz, 1H), 7.21-7.19 (m, 2H), 4.89-4.77 (m, 1H), 4.19 (t, J=6.8 Hz, 1H), 3.18-3.08 (m, 2H), 2.06-1.96 (m, 1H), 1.86-1.77 (m, 1H), 1.65-1.62 (m, 6H), 1.60-1.52 (m, 2H), 1.40 (s, 9H). $^{13}$C NMR (CDCl$_3$; 100 MHz): δ 156.7, 155.9, 142.8, 133.7, 121.9, 121.6, 119.5, 111.9, 78.8, 49.0, 47.5, 40.3, 34.4, 28.2, 26.4, 21.3. LRMS m/z calculated for C$_{19}$H$_{30}$N$_4$O$_2$ (M+H$^+$) 347.2; found 347.2.

tert-butyl-(4-amino-4-(5,6-difluoro-benzo[d]imidazol-2-yl)butyl)carbamate-L-ornithine (4e)

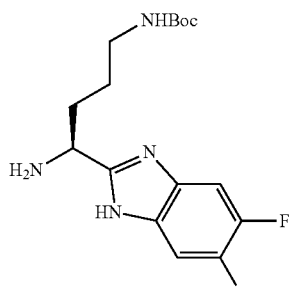

$^1$H NMR (CDC$_3$; 400 MHz): δ 7.28 (t, J=8.6 Hz, 2H), 4.38-4.35 (m, 1H), 3.31-3.22 (m, 1H), 3.11-3.03 (m, 1H), 1.99-1.90 (m, 1H), 1.85-1.77 (m, 1H), 1.68-1.58 (m, 1H), 1.56-1.49 (m, 1H), 1.43 (s, 9H). $^{13}$C NMR (CDCl$_3$; 100 MHz): δ 156.8, 148.9, 147.0, 133.4, 102.5, 79.8, 49.5, 39.4, 33.7, 28.4, 26.5. LRMS m/z calculated for C$_{16}$H$_{22}$F$_2$N$_4$O$_2$ (M+H$^+$) 341.2; found 341.1.

tert-butyl-(4-amino-4-(4-methoxy-benzo[d]imidazol-2-yl)butyl)carbamate-L-ornithine (4f)

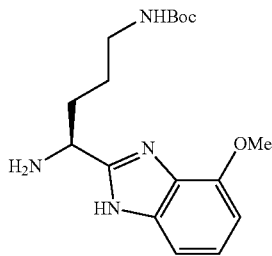 [SMILES: COc1cccc2[nH]c([C@@H](N)CCCNC(=O)OC(C)(C)C)nc12]

$^1$H NMR (CDC$_3$; 400 MHz): δ 7.08 (s, 2H), 6.58 (s, 1H), 4.58-4.53 (m, 1H), 3.87 (s, 3H), 3.14-3.06 (m, 1H), 3.03-2.96 (m, 1H), 2.11-2.00 (m, 1H), 1.97-1.90 (m, 1H), 1.51-1.39 (m, 2H), 1.36 (s, 9H). $^{13}$C NMR (CDC$_3$; 100 MHz): δ 177.1, 162.6, 156.5, 149.4, 138.2, 129.6, 123.6, 106.9, 102.8, 79.4, 55.8, 55.5, 49.6, 39.5, 36.5, 32.6, 31.4, 28.3, 26.3, 22.5. LRMS m/z calculated for C$_{17}$H$_{26}$N$_4$O$_3$ (M+H$^+$) 335.2; found 335.2.

tert-butyl-(4-amino-4-(4-methoxy-1-methyl-benzo[d]imidazol-2-yl)butyl)carbamate-L-ornithine (4g)

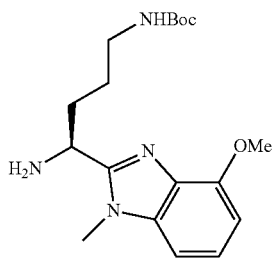 [SMILES: COc1cccc2c1nc([C@@H](N)CCCNC(=O)OC(C)(C)C)n2C]

$^1$H NMR (CDC$_3$; 400 MHz): δ 7.19 (t, J=8.5 Hz, 1H), 6.92 (d, J=8.6 Hz, 1H), 6.67 (d, J=8.3 Hz, 1H), 4.23-4.19 (m, 1H), 4.00 (s, 3H), 3.75 (s, 3H), 3.17-3.11 (m, 2H), 2.05-1.96 (m, 1H), 1.92-1.82 (m, 1H), 1.70-1.53 (m, 2H), 1.40 (s, 9H). $^{13}$C NMR (CDC$_3$; 100 MHz): δ 156.2, 151.3, 137.3, 132.0, 123.1, 102.5, 102.3, 79.2, 55.6, 48.5, 40.0, 34.1, 30.0, 28.2, 26.5. LRMS m/z calculated for C$_{18}$H$_{28}$N$_4$O$_3$ (M+H$^+$) 349.2; found 349.1.

tert-butyl-(4-amino-4-(4-methoxy-1-ethyl-benzo[d]imidazol-2-yl)butyl)carbamate-L-ornithine (4h)

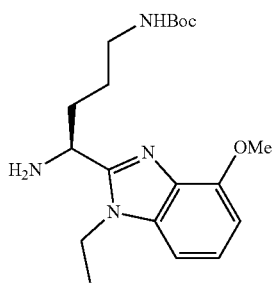 [SMILES: CCn1c([C@@H](N)CCCNC(=O)OC(C)(C)C)nc2c(OC)cccc21]

$^1$H NMR (CDCl$_3$; 400 MHz): δ 7.15 (t, J=8.4 Hz, 1H), 6.92 (d, J=7.5 Hz, 1H), 6.62 (d, J=8.4 Hz, 1H), 4.23-4.12 (m, 1H), 3.91 (s, 3H), 3.11-3.03 (m, 2H), 2.01-1.92 (m, 1H), 1.88-1.79 (m, 1H), 1.61-1.44 (m, 2H), 1.38 (t, J=7.5 Hz, 3H), 1.35 (s, 9H). $^{13}$C NMR (CDCl$_3$; 100 MHz): δ 156.1, 155.2, 151.23, 135.9, 132.1, 123.2, 102.8, 79.0, 55.5, 50.5, 48.2, 39.9, 38.4, 34.4, 28.2, 26.3, 15.1. LRMS m/z calculated for C$_{19}$H$_3$N$_4$O$_3$ (M+H$^+$) 363.2; found 363.3.

tert-butyl-(4-amino-4-(5-methoxy-1H-benzo[d]imidazol-2-yl)butyl)carbamate-L-ornithine (4i)

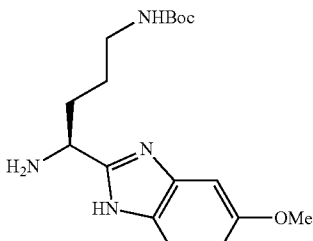

$^1$H NMR (CDC$_3$; 400 MHz): δ 7.32 (d, J=8.4 Hz, 1H), 6.91 (s, 1H), 6.75 (dd, J=2.3 Hz, J=8.6 Hz, 1H), 4.19 (m, 1H), 3.71 (s, 3H), 3.39 (s, 3H), 1.91-1.83 (m, 1H), 1.76-1.69 (m, 1H), 1.48-1.42 (m, 2H), 1.34 (s, 9H). $^{13}$C NMR (CDCl$_3$; 100 MHz): δ 156.7, 156.2, 138.2, 133.2, 115.8, 111.7, 97.7, 79.2, 55.8, 50.3, 49.8, 39.7, 33.8, 28.5, 26.2. LRMS m/z calculated for C$_{17}$H$_{26}$N$_4$O$_3$ (M+H$^+$) 335.2; found 335.3.

tert-butyl-(4-amino-4-(5-methoxy-1-methyl-benzo[d]imidazol-2-yl)butyl)carbamate-L-ornithine (4j)

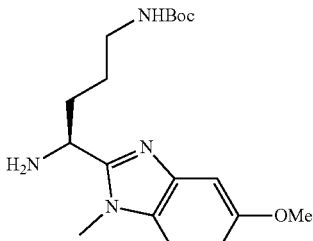

$^1$H NMR (CDC$_3$; 400 MHz): δ 7.21 (d, J=2.4 Hz, 1H), 7.17 (d, J=8.7 Hz, 1H), 6.90 (dd, J=2.4 Hz, J=8.7 Hz, 1H), 4.20-4.18 (m, 1H), 3.82 (s, 3H), 3.72 (s, 3H), 3.15-3.10 (m, 2H), 2.05-1.95 (m, 1H), 1.90-1.80 (m, 1H), 1.68-1.49 (m, 2H), 1.40 (s, 9H). $^{13}$C NMR (CDCl$_3$; 100 MHz): δ 157.1, 156.3, 155.9, 142.5, 130.4, 112.4, 109.7, 101.5, 79.0, 55.6, 48.3, 39.9, 33.9, 29.9, 28.5, 26.6. LRMS m/z calculated for C$_{18}$H$_{28}$N$_4$O$_3$ (M+H$^+$) 349.2; found 349.2.

tert-butyl-(4-amino-4-(5-methoxy-1-ethyl-benzo[d]imidazol-2-yl)butyl)carbamate-L-ornithine (4k)

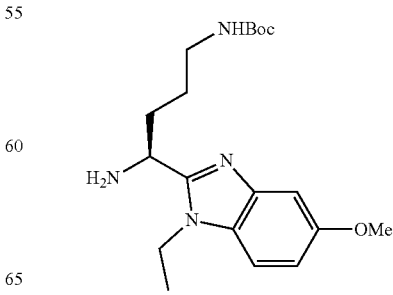

¹H NMR (CDCl₃; 400 MHz): δ 7.15-7.12 (m, 2H), 6.83 (dd, J=2.4 Hz, J=8.6 Hz, 1H), 4.17-4.10 (m, 2H), 4.08-4.05 (m, 1H), 3.76 (s, 3H), 2.00-1.92 (m, 1H), 1.84-1.77 (m, 1H), 1.61-1.53 (m, 1H), 1.50-1.43 (m, 1H), 1.34 (s, 12H). ¹³C NMR (CDCl₃; 100 MHz): δ 156.1, 142.9, 129.2, 112.5, 109.9, 101.8, 55.9, 50.3, 48.2, 40.1, 38.5, 34.5, 28.3, 26.5, 15.4. LRMS m/z calculated for $C_{19}H_3N_4O_3$ (M+H⁺) 363.2; found 363.2.

tert-butyl-(4-amino-4-(4-ethoxy-1-methyl-benzo[d]imidazol-2-yl)butyl)carbamate-L-ornithine (41)

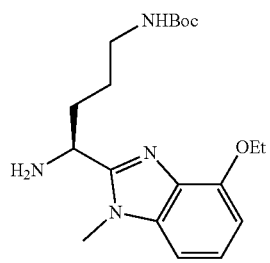 [SMILES: CCOc1cccc2c1nc([C@@H](N)CCCNC(=O)OC(C)(C)C)n2C]

¹H NMR (CDCl₃; 400 MHz): δ 7.16 (t, J=7.8 Hz, 1H), 6.89 (d, J=7.7 Hz, 1H), 6.67 (d, J=7.8 Hz, 1H), 4.31-4.26 (m, 1H), 4.25-4.22 (m, 2H), 3.75 (s, 3H), 3.16-3.11 (m, 2H), 2.04-1.95 (m, 1H), 1.90-1.82 (m, 1H), 1.69-1.55 (m, 2H), 1.52 (t, J=7.2 Hz, 3H), 1.40 (s, 9H). ¹³C NMR (CDC₃; 100 MHz): δ 156.0, 150.2, 137.5, 132.4, 123.1, 103.7, 101.7, 79.1, 64.1, 48.7, 39.8, 33.7, 30.2, 28.4, 26.5, 14.6. LRMS m/z calculated for $C_{19}H_{30}N_4O_3$ (M+H⁺) 363.2; found 363.1.

3a. General Procedure for Synthesis of Benzimidazole Haloacetamidines 5a-b.ᵃ

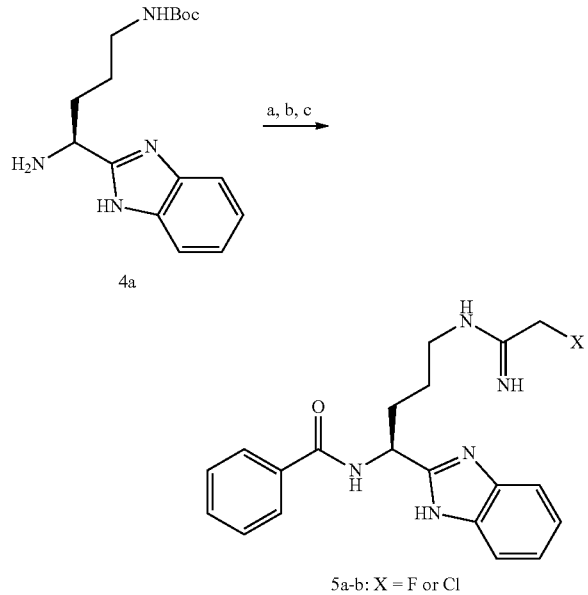

ᵃReagents: (a) benzoyl chloride, TEA, THF/H₂O; (b) TFA, CH₂Cl₂; (c) ethyl 2-haloacetimidate, TEA, MeOH To a stirred solution of 4a (1.0 eq) in THF/H₂O (1:1) was added TEA (3.0 eq) followed by benzoyl chloride (1.0 eq) and allowed to stir at rt for 3 h. Solvents were evaporated and the crude product was purified by reverse phase HPLC using MeCN:H₂O (0.5% TFA) as the eluent to give the product in 72-76% yield. This product was then treated with TFA to remove the Boc group giving the Bz-Om-benzimidazole intermediate. The solvent was then evaporated to dryness and the crude material was dried in vacuo. To a stirred solution of the corresponding Bz-Om-benzimidazole intermediate in dry MeOH was added TEA (4.0 eq) followed by ethyl haloacetimidate HCl (2.0 eq). The reaction was stirred under N₂ at rt for 3 h. Solvents were then evaporated under reduced pressure and the crude product was purified by reverse phase HPLC using MeCN:H₂O (0.5% TFA) as an eluent to give compound 5a-b in 72-78% yield.

(N1-benzoyl-N5-(2-fluoro-1-iminoethyl)-1-(1H-benzo[d]imidazol-2-yl)-L-ornithine) (5a)

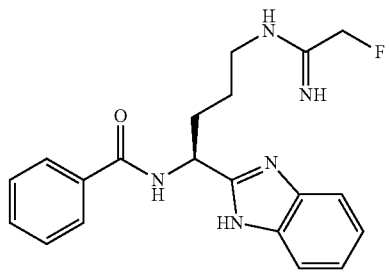 [SMILES: N=C(CF)NCCC[C@H](NC(=O)c1ccccc1)c1nc2ccccc2[nH]1]

¹H NMR (CD₃OD; 400 MHz): δ 8.00-7.97 (m, 2H), 7.81-7.76 (m, 5H), 5.66-5.63 (m, 1H), 5.30 (d, J=45.6 Hz, 2H), 3.55-3.50 (m, 2H), 2.39-2.34 (m, 2H), 2.05-0.192 (m, 1H), 1.90-1.83 (m, 1H). ¹³C NMR (100 MHz, CD₃OD) 170.5, 155.4, 134.1, 133.5, 133.3, 129.7, 128.8, 127.2, 115.2, 79.8, 78.1, 42.8, 30.6, 25.2. HRMS m/z calculated for $C_2H_{23}FN_5O$ (M+H⁺) 368.1878; found 368.1880.

(N1-benzoyl-N5-(2-chloro-1-iminoethyl)-1-(1H-benzo[d]imidazol-2-yl)-L-ornithine) (5b)

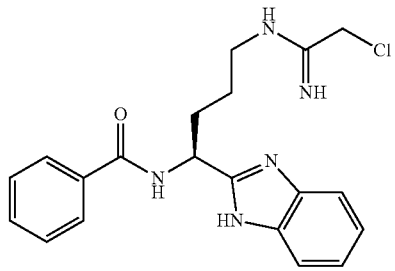 [SMILES: N=C(CCl)NCCC[C@H](NC(=O)c1ccccc1)c1nc2ccccc2[nH]1]

¹H NMR (CD₃OD; 400 MHz): δ 8.06-7.97 (m, 2H), 7.85-7.78 (m, 2H), 7.62-7.59 (m, 3H), 7.58-7.50 (m, 2H), 5.67-5.63 (m, 1H), 4.39 (s, 2H), 3.54-3.41 (m, 2H), 2.40-2.35 (m, 2H), 2.05-1.92 (m, 1H), 1.90-1.81 (m, 1H). ¹³C NMR (100 MHz, CD₃OD) δ 170.5, 164.5, 162.5, 155.3, 134.1, 133.6, 133.0, 129.7, 128.8, 127.4, 115.1, 43.3, 40.1, 30.4, 25.0. HRMS m/z calculated for $C_{20}H_{23}ClN_5O$ (M+H⁺) 384.1583; found 384.1588.

3b. General Procedure for Synthesis of Benzimidazole Haloacetamidines 5c-d[a]

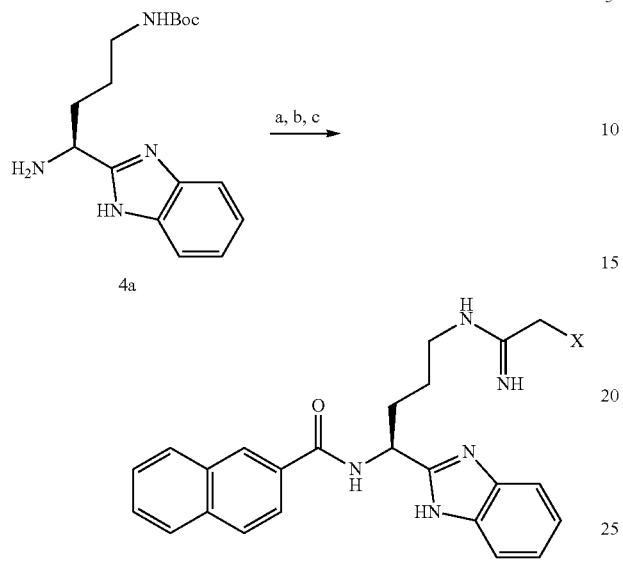

5c-d:
X = F or Cl

[a]Reagents: (a) naphthoyl chloride, TEA, THF/H$_2$O; (b) TFA, CH$_2$Cl$_2$; (c) ethyl 2-haloacetimidate, TEA, MeOH To a stirred solution of 4a (1.0 eq) in THF/H$_2$O (1:1) was added TEA (3.0 eq) followed by naphthoyl chloride (1.0 eq) and allowed to stir at rt for 3 h. Solvents were evaporated and the crude product was purified by reverse phase HPLC using MeCN:H$_2$O (0.5% TFA) as the eluent to give the product in 68-73% yield. This product was then treated with TFA to remove the Boc group giving the Naphthyl-Orn-benzimidazole intermediate. The solvent was then evaporated to dryness and the crude material was dried in vacuo. To a stirred solution of the corresponding Naphthyl-Orn-benzimidazole intermediate in dry MeOH was added TEA (4.0 eq) followed by ethyl haloacetimidate HCl (2.0 eq). The reaction was stirred under N$_2$ at rt for 3 h. Solvents were then evaporated under reduced pressure and the crude product was purified by reverse phase HPLC using MeCN:H$_2$O (0.5% TFA) as an eluent to give compound 5c-d in 30-40% yield.

(N1-[2-naphthol-N5-(2-fluoro-1-iminoethyl)-1-(1H-benzod[d]imidazol-2-yl)-L-ornithine) (5c)

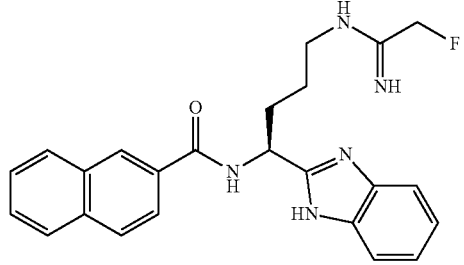 [SMILES: N=C(CF)NCCC[C@H](NC(=O)c1ccc2ccccc2c1)c1nc2ccccc2[nH]1]

$^1$H NMR (CD$_3$OD; 400 MHz): δ 8.58 (s, 1H), 8.11-7.93 (m, 4H), 7.81-7.74 (m, 2H), 7.66-7.56 (m, 4H), 5.74-5.70 (m, 1H), 5.30 (d, J=45.6 Hz, 2H), 3.58-3.50 (m, 2H), 2.44-2.40 (m, 2H), 2.10-1.86 (m, 2H). $^{13}$C NMR (100 MHz, CD$_3$OD) δ 170.5, 164.6, 164.4, 136.6, 133.9, 132.9, 131.3, 130.2, 129.6, 129.5, 129.3, 128.8, 128.1, 127.4, 125.0, 115.1, 79.8, 78.1, 42.8, 30.5, 25.2. HRMS m/z calculated for C$_{24}$H$_{25}$FN$_5$O (M+H$^+$) 418.2035; found 418.2040.

(N1-[2-naphthoyl-N5-(2-chloro-1-iminoethyl)-1-(1H-benzo[d]imidazol-2-yl)-L-ornithine) (5d)

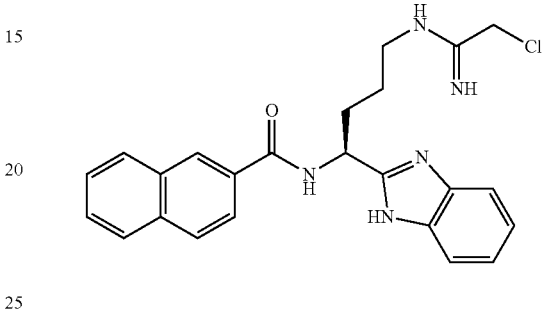

$^1$H NMR (CD$_3$OD; 400 MHz): δ 8.58 (s, 1H), 8.12-7.92 (m, 4H), 7.81-7.73 (m, 2H), 7.67-7.55 (m, 4H), 5.74-5.70 (m, 1H), 4.42 (s, 2H), 3.57-3.49 (m, 2H), 2.43-2.39 (m, 2H), 2.10-1.85 (m, 2H). $^{13}$C NMR (100 MHz, CD$_3$OD) δ 170.4, 169.4, 164.9, 163.0, 162.6, 154.6, 139.1, 133.8, 133.7, 131.7, 131.2, 130.3, 128.9, 127.2, 115.2, 43.3, 40.1, 30.4, 25.0. HRMS m/z calculated for C$_{24}$H$_{25}$ClN$_5$O (M+H$^+$) 434.1739; found 434.1741.

3c. General Procedure for Synthesis of Benzimidazole Haloacetamidines 5e-w.[a]

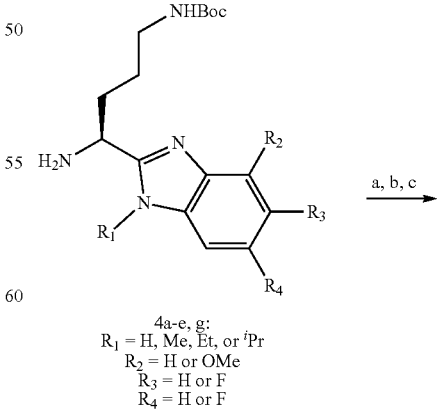

4a-e, g:
R$_1$ = H, Me, Et, or $^i$Pr
R$_2$ = H or OMe
R$_3$ = H or F
R$_4$ = H or F

-continued

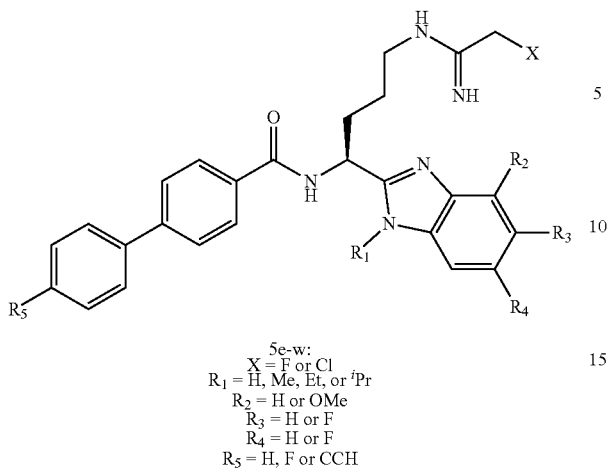

5e-w:
X = F or Cl
R₁ = H, Me, Et, or ⁱPr
R₂ = H or OMe
R₃ = H or F
R₄ = H or F
R₅ = H, F or CCH

ªReagents: (a) biphenyl-4-carbonyl chloride, TEA, CH₂Cl₂; (b) TFA, CH₂Cl₂; (c) ethyl 2-haloacetimidate, TEA, MeOH To a stirred solution of 4a-e, g (1.0 eq) in CH₂Cl₂ was added TEA (3.0 eq) followed by biphenyl-4-carbonyl chloride (1.0 eq) and allowed to stir at rt for 3 h. Solvents were evaporated and the crude product was purified by reverse phase HPLC using MeCN:H₂O (0.5% TFA) as the eluent to give the product in 69-80% yield. This product was then treated with TFA to remove the Boc group giving the 4-Ph-Bz-Om-benzimidazole intermediate. The solvent was then evaporated to dryness and the crude material was dried in vacuo. To a stirred solution of the corresponding 4-Ph-Bz-Orn-benzimidazole intermediate in dry MeOH was added TEA (4.0 eq) followed by ethyl haloacetimidate HCl (2.0 eq). The reaction was stirred under N₂ at rt for 3 h. Solvents were then evaporated under reduced pressure and the crude product was purified by reverse phase HPLC using MeCN:H₂O (0.5% TFA) as an eluent to give compound 5a-p in 53-75% yield. (N1-[1,4'-Phenyl]benzol-N5-(2-fluoro-1-iminoethyl)-1-(1H-benzo[d]imidazol-2-yl)-L-ornithine) (5e)

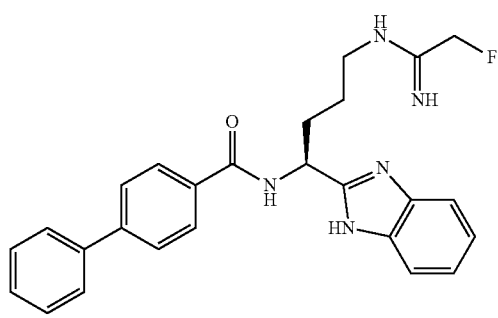 [SMILES: N=C(CF)NCCC[C@H](NC(=O)c1ccc(-c2ccccc2)cc1)c1nc2ccccc2[nH]1]

¹H NMR (CD₃OD; 400 MHz): δ 8.07 (d, J=8.4 Hz, 2H), 7.87-7.76 (m, 4H), 7.77 (d, J=8.4 Hz, 2H), 7.69-7.58 (m, 2H), 7.51-7.47 (m, 2H), 7.43-7.39 (m, 1H), 5.70-5.56 (m, 1H), 5.30 (d, J=45.2 Hz, 2H), 3.51-3.49 (m, 2H), 2.42-2.36 (m, 2H), 2.06-1.83 (m, 2H). ¹³C NMR (100 MHz, CD₃OD) δ 170.2, 164.5, 155.4, 146.5, 141.0, 132.8, 132.7, 130.1, 129.5, 129.3, 128.2, 127.5, 115.3, 79.8, 78.1, 42.8, 30.5, 25.2. HRMS m/z calculated for C₂₆H₂₇FN₅O (M+H⁺) 444.2191; found 444.2194.

(N1-[1,4'-Phenyl]benzoyl-N5-(2-chloro-1-iminoethyl)-1-(1H-benzo[d]imidazol-2-yl)-L-ornithine)

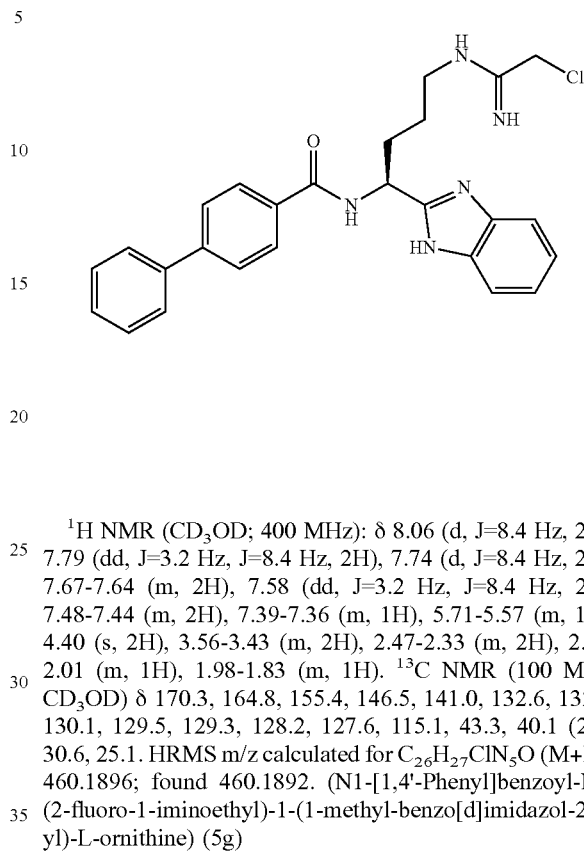

¹H NMR (CD₃OD; 400 MHz): δ 8.06 (d, J=8.4 Hz, 2H), 7.79 (dd, J=3.2 Hz, J=8.4 Hz, 2H), 7.74 (d, J=8.4 Hz, 2H), 7.67-7.64 (m, 2H), 7.58 (dd, J=3.2 Hz, J=8.4 Hz, 2H), 7.48-7.44 (m, 2H), 7.39-7.36 (m, 1H), 5.71-5.57 (m, 1H), 4.40 (s, 2H), 3.56-3.43 (m, 2H), 2.47-2.33 (m, 2H), 2.09-2.01 (m, 1H), 1.98-1.83 (m, 1H). ¹³C NMR (100 MHz, CD₃OD) δ 170.3, 164.8, 155.4, 146.5, 141.0, 132.6, 132.5, 130.1, 129.5, 129.3, 128.2, 127.6, 115.1, 43.3, 40.1 (2C), 30.6, 25.1. HRMS m/z calculated for C₂₆H₂₇ClN₅O (M+H⁺) 460.1896; found 460.1892. (N1-[1,4'-Phenyl]benzoyl-N5-(2-fluoro-1-iminoethyl)-1-(1-methyl-benzo[d]imidazol-2-yl)-L-ornithine) (5g)

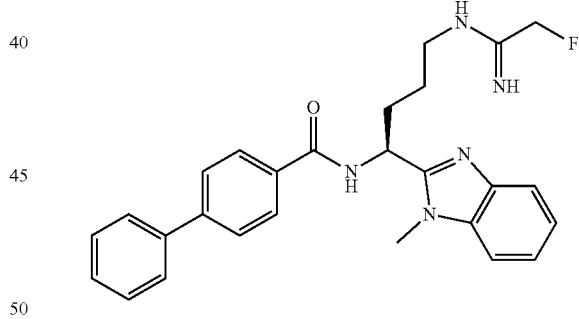

¹H NMR (CD₃OD; 400 MHz): δ 8.01 (d, J=8.4 Hz, 2H), 7.87 (dd, J=2.3 Hz, J=8.1 Hz, 1H), 7.81 (dd, J=2.3 Hz, J=7.2 Hz, 1H), 7.75 (d, J=8.3 Hz, 2H), 7.66 (d, J=8.3 Hz, 2H), 7.63-7.58 (m, 2H), 7.47 (t, J=7.3 Hz, 2H), 7.39 (t, J=7.8 Hz, 1H), 5.78-5.74 (m, 1H), 5.27 (d, J=45.4 Hz, 2H), 4.17 (s, 3H), 3.54-3.44 (m, 2H), 2.45-2.26 (m, 2H), 2.06-2.01 (m, 1H), 1.91-1.80 (m, 1H). ¹³C NMR (100 MHz, CD₃OD) 168.5, 163.2, 162.9, 161.4, 160.9, 153.0, 145.1, 139.6, 133.6, 131.21, 128.7 (2C), 127.9, 127.9, 126.8, 126.7, 125.5, 125.4, 115.2, 111.6, 78.5, 76.7, 45.7, 41.4, 30.3, 28.9, 23.7. HRMS m/z calculated for C₂₇H₂₈FN₅O (M+H⁺) 458.2351; found 458.2349.

59

(N1-[1,4'-Phenyl]benzol-N5-(2-chloro-1-imino-ethyl)-1-(1-methyl-benzo[d]imidazol-2-yl)-L-ornithine) (5h)

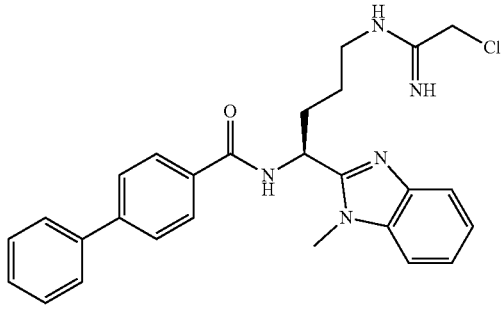 [SMILES: Cn1c([C@H](CCCNC(=N)CCl)NC(=O)c2ccc(-c3ccccc3)cc2)nc2ccccc21]

¹H NMR (CD₃OD; 400 MHz): δ 8.00 (d, J=8.3 Hz, 2H), 7.86 (dd, J=2.4 Hz, J=7.6 Hz, 1H), 7.80 (dd, J=2.4 Hz, J=7.2 Hz, 1H), 7.75 (d, J=8.7 Hz, 2H), 7.68-7.65 (m, 2H), 7.62-7.57 (m, 2H), 7.47 (t, J=7.2 Hz, 2H), 7.39 (t, J=7.2 Hz, 1H), 5.77-5.73 (m, 1H), 4.38 (s, 2H), 4.14 (s, 3H), 3.53-3.41 (m, 2H), 2.46-2.29 (m, 2H), 2.08-1.97 (m, 1H), 1.93-1.81 (m, 1H). ¹³C NMR (100 MHz, CD₃OD) δ 168.5, 163.4, 161.3, 155.3, 152.9, 145.1, 139.5, 134.9, 133.9, 133.7, 131.3, 128.7 (2C), 127.9, 127.9, 126.8, 126.7, 125.3, 125.3, 115.3, 111.5, 45.7, 42.0, 38.7, 30.2, 29.0, 23.5. HRMS m/z calculated for $C_{27}H_{28}ClN_5O$ (M+H⁺) 474.2055; found 474.2056.

(N1-[1,4'-Phenyl]benzoyl-N5-(2-fluoro-1-imino-ethyl)-1-(1-ethyl-benzo[d]imidazol-2-yl)-L-ornithine) (5i)

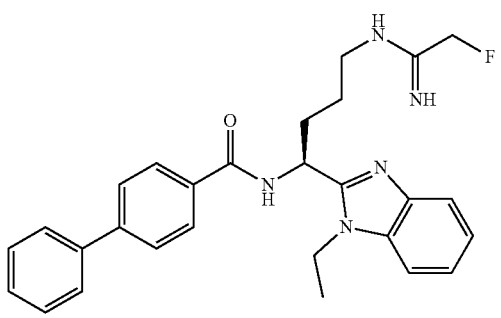 [SMILES: CCn1c([C@H](CCCNC(=N)CF)NC(=O)c2ccc(-c3ccccc3)cc2)nc2ccccc21]

¹H NMR (CD₃OD; 400 MHz): δ 7.99 (d, J=8.6 Hz, 2H), 7.88 (dd, J=2.1 Hz, J=7.2 Hz, 1H), 7.81 (dd, J=2.2 Hz, J=7.1 Hz, 1H), 7.75 (d, J=8.6 Hz, 2H), 7.66 (d, J=7.7 Hz, 2H), 7.61-7.56 (m, 2H), 7.47 (t, J=7.3 Hz, 2H), 7.39 (t, J=7.7 Hz, 1H), 5.78-5.74 (m, 1H), 5.27 (d, J=45.2 Hz, 2H), 4.66-4.58 (m, 2H), 3.54-3.45 (m, 2H), 2.45-2.36 (m, 1H), 2.34-2.25 (m, 1H), 2.06-1.97 (m, 1H), 1.93-1.81 (m, 1H), 1.41 (t, J=7.1 Hz, 3H). ¹³C NMR (100 MHz, CD₃OD) δ 168.2, 163.1, 163.0, 152.5, 145.1, 139.5, 132.8, 132.3, 131.9, 131.4, 128.7 (2C), 127.9, 126.8, 126.7, 125.1, 124.9, 123.2, 115.9, 111.6, 78.5, 76.7, 45.5, 41.6, 39.7, 29.4, 23.8, 13.6. HRMS m/z calculated for $C_{28}H_{30}FN_5O$ (M+H⁺) 472.2507; found 472.2506.

60

(N1-[1,4'-Phenyl]benzoyl-N5-(2-chloro-1-imino-ethyl)-1-(1-ethyl-benzo[d]imidazol-2-yl)-L-ornithine) (5j)

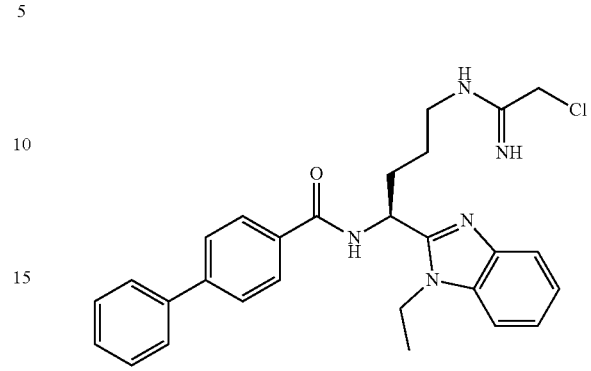

¹H NMR (CD₃OD; 400 MHz): δ 7.99 (d, J=8.3 Hz, 2H), 7.90 (dd, J=2.1 Hz, J=7.4 Hz, 1H), 7.81 (dd, J=2.4 Hz, J=7.3 Hz, 1H), 7.75 (d, J=8.3 Hz, 2H), 7.66 (d, J=8.4 Hz, 2H), 7.62-7.56 (m, 2H), 7.46 (t, J=7.2 Hz, 2H), 7.40 (t, J=7.3 Hz, 1H), 5.78-5.74 (m, 1H), 4.67-4.60, 4.37 (s, 2H), 3.52-3.42 (m, 2H), 2.46-2.36 (m, 1H), 2.34-2.26 (m, 1H), 2.08-1.97 (m, 1H), 1.93-1.82 (m, 1H), 1.54 (t, J=7.5 Hz, 3H). ¹³C NMR (100 MHz, CD₃OD) δ 168.3, 163.4, 161.3, 161.0, 152.4, 145.1, 139.6, 134.6, 132.7, 131.3, 128.7 (2C), 127.9, 126.8, 126.7, 125.2, 125.1, 115.7, 111.7, 100.0, 56.1, 45.5, 42.1, 39.8, 38.7, 29.3, 23.7, 13.5. HRMS m/z calculated for $C_{28}H_{30}ClN_5O$ (M+H⁺) 488.2212; found 488.2214.

(N1-[1,4'-Phenyl]benzoyl-N5-(2-fluoro-1-imino-ethyl)-1-(1-isopropyl-benzo[d]imidazol-2-yl)-L-ornithine) (5k)

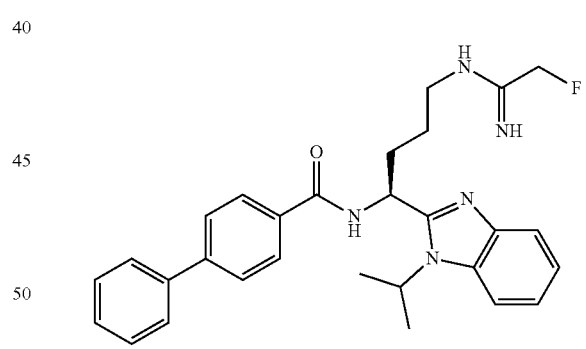

¹H NMR (CD₃OD; 400 MHz): δ 8.06-8.02 (m, 1H), 7.98 (d, J=8.5 Hz, 2H), 7.83-7.79 (m, 1H), 7.75 (d, J=8.5 Hz, 2H), 7.66 (dd, J=2.1 Hz, J=8.1 Hz, 2H), 7.57-7.53 (m, 2H), 7.47 (t, J=7.4 Hz, 2H), 7.39 (t, J=7.4 Hz, 1H), 5.80-5.76 (m, 1H), 5.28 (d, J=45.3 Hz, 2H), 5.21-5.16 (m, 1H), 3.57-3.44 (m, 2H), 2.45-2.36 (m, 1H), 2.35-2.27 (m, 1H), 2.06-1.96 (m, 1H), 1.93-1.84 (m, 1H), 1.81 (d, J=6.6 Hz, 3H), 1.71 (d, J=6.6 Hz, 3H). ¹³C NMR (100 MHz, CD₃OD) δ 168.4, 166.0, 165.1, 162.5, 161.4, 152.1, 145.1, 139.5, 133.0, 131.1, 130.6, 128.7 (2C), 127.9, 126.8, 126.6, 125.7, 125.4, 115.1, 114.4, 78.4, 76.7, 50.8, 46.0, 41.4, 29.0, 23.7, 19.6 (2C). HRMS m/z calculated for $C_{29}H_{32}FN_5O$ (M+H) 486.2664; found 486.2666.

61
(N1-[1,4'-Phenyl]benzoyl-N5-(2-chloro-1-imino-ethyl)-1-(1-isopropyl-benzo[d]imidazol-2-yl)-L-ornithine) (5l)

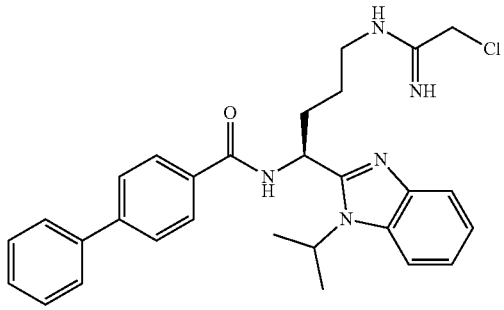 [SMILES: CC(C)n1c([C@H](CCCNC(=N)CCl)NC(=O)c2ccc(-c3ccccc3)cc2)nc2ccccc21]

$^1$H NMR (CD$_3$OD; 400 MHz): δ 8.05-8.03 (m, 1H), 7.99 (d, J=8.3 Hz, 2H), 7.83-7.79 (m, 1H), 7.75 (d, J=8.4 Hz, 2H), 7.67 (dd, J=2.2 Hz, J=8.3 Hz, 2H), 7.58-7.53 (m, 2H), 7.47 (t, J=7.3 Hz, 2H), 7.39 (t, J=7.6 Hz, 1H), 5.80-5.76 (m, 1H), 5.25-5.15 (m, 1H), 4.38 (s, 2H), 3.55-3.42 (m, 2H), 2.46-2.36 (m, 1H), 2.35-2.27 (m, 1H), 2.07-1.96 (m, 1H), 1.93-1.85 (m, 1H), 1.81 (d, J=6.7 Hz, 3H), 1.72 (d, J=6.5 Hz, 3H). $^{13}$C NMR (100 MHz, CD$_3$OD) δ 168.4, 166.2, 165.3, 163.3, 160.9, 152.1, 145.1, 139.5, 131.0, 130.4, 128.6 (2C), 127.9, 126.8, 126.7, 125.9, 125.5, 115.6, 115.0, 114.5, 52.8, 50.9, 46.1, 41.9, 38.6, 29.0, 23.6, 19.6 (2C). HRMS m/z calculated for C$_{29}$H$_{32}$ClN$_5$O (M+H$^+$) 502.2368; found 502.2370.

(N1-[1,4'-Phenyl]benzoyl-N5-(2-fluoro-1-imino-ethyl)-1-(4-methoxy-1-methyl-benzo[d]imidazol-2-yl)-L-ornithine) (5m)

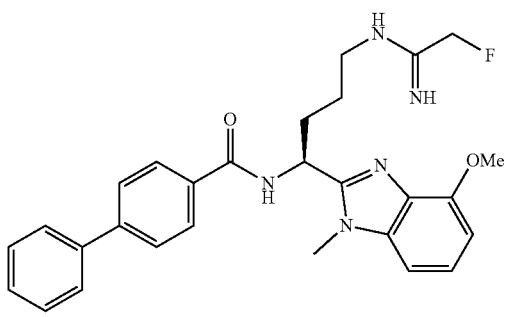 [SMILES: COc1cccc2c1nc([C@H](CCCNC(=N)CF)NC(=O)c1ccc(-c3ccccc3)cc1)n2C]

$^1$H NMR (CD$_3$OD; 400 MHz): δ 7.97 (d, J=8.5 Hz, 2H), 7.75 (d, J=8.6 Hz, 2H), 7.66 (dd, J=1.8 Hz, J=7.2 Hz, 2H), 7.49-7.37 (m, 4H), 7.28 (d, J=8.4 Hz, 2H), 6.99 (d, J=8.1 Hz, 2H), 5.69-5.64 (m, 1H), 5.27 (d, J=45.1 Hz, 2H), 4.03 (s, 3H), 4.01 (s, 3H), 3.51-3.41 (m, 2H), 2.34-2.28 (m, 2H), 2.00-1.89 (m, 1H), 1.86-1.75 (m, 1H). $^{13}$C NMR (100 MHz, CD$_3$OD) δ 168.5, 163.0, 162.9, 161.3, 160.9, 152.1, 148.1, 144.9, 139.5, 134.6, 131.0, 128.6, 127.9, 126.8, 126.7, 122.7, 117.9, 115.0, 105.9, 103.6, 78.3, 76.6, 55.1, 46.0, 41.4, 30.7, 28.7, 23.5. HRMS m/z calculated for C$_{28}$H$_3$FN$_5$O$_2$ (M+H$^+$) 488.2456; found 488.2455.

62
(N1-[1,4'-Phenyl]benzoyl-N5-(2-chloro-1-imino-ethyl)-1-(4-methoxy-1-methyl-benzo[d]imidazol-2-yl)-L-ornithine) (5n)

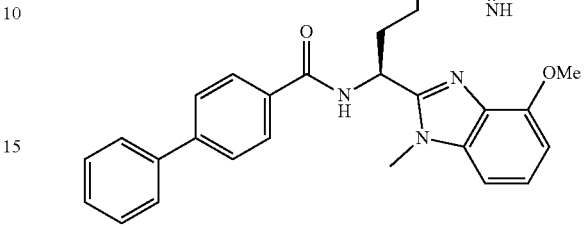

$^1$H NMR (CD$_3$OD; 400 MHz): δ 7.98 (d, J=8.5 Hz, 2H), 7.74 (d, J=8.6 Hz, 2H), 7.65 (dd, J=1.8 Hz, J=8.4 Hz, 2H), 7.48-7.36 (m, 4H), 7.29 (d, J=8.4 Hz, 2H), 7.00 (d, J=8.2 Hz, 2H), 5.69-5.64 (m, 1H), 4.36 (s, 2H), 4.03 (s, 3H), 4.02 (s, 3H), 3.49-3.39 (m, 2H), 2.35-2.28 (m, 2H), 2.00-1.91 (m, 1H), 1.85-1.75 (m, 1H). $^{13}$C NMR (100 MHz, CD$_3$OD) δ 168.5, 163.2, 158.1, 157.7, 152.1, 148.5, 145.0, 139.6, 134.8, 131.1, 128.6, 127.9, 127.9, 126.8, 126.7, 126.6, 105.7, 103.6, 85.2, 55.1, 46.0, 43.0, 42.0, 38.6, 30.5, 28.8, 28.6, 23.5. HRMS m/z calculated for C$_{28}$H$_3$ClN$_5$O$_2$ (M+H$^+$) 504.2161; found 504.2162.

(N1-4'-[1,1'-Phenyl]benzoyl-N5-(2-fluoro-1-imino-ethyl)-1-(1H-benzo[d]imidazol-2-yl)-L-ornithine) (5o)

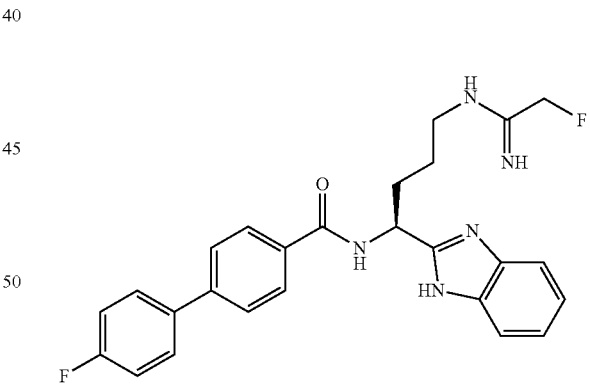

$^1$H NMR (CD$_3$OD; 500 MHz): δ 7.94 (d, J=9.3 Hz, 2H), 7.67-7.63 (m, 4H), 7.47-7.43 (m, 2H), 7.12-7.09 (m, 2H), 5.56-5.53 (m, 1H), 5.16 (d, J=45.1 Hz, 2H), 3.44-3.35 (m, 2H), 2.29-2.24 (m, 2H), 1.94-1.86 (m, 1H), 1.81-1.72 (m, 1H). $^{13}$C NMR (125 MHz, CD$_3$OD) δ 168.7, 163.9, 163.1, 163.0, 162.0, 161.7, 161.3, 153.9, 143.8, 136.0, 131.9, 131.4, 128.7, 128.6, 128.1, 126.5, 125.7, 115.4, 115.3, 113.8, 109.2, 78.2, 76.9, 41.4, 29.1, 23.7. HRMS m/z calculated for C$_{26}$H$_{25}$F$_2$N$_5$O (M+H) 462.2100; found 462.2097.

63

(N1-4'-F-[1,1'-Phenyl]benzol-N5-(2-chloro-1-imino-ethyl)-1-(1H-benzo[d]imidazol-2-yl)-L-ornithine) (5p)

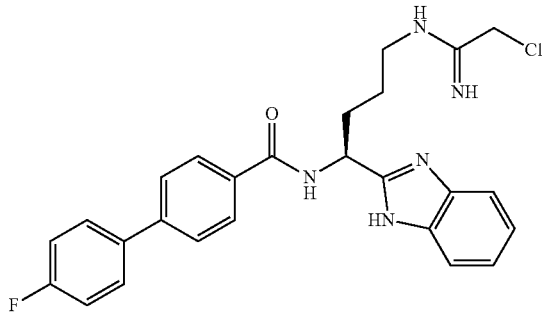 [SMILES: N=C(CCl)NCCC[C@H](NC(=O)c1ccc(-c2ccc(F)cc2)cc1)c1nc2ccccc2[nH]1]

$^1$H NMR (CD$_3$OD; 500 MHz): δ 7.94 (d, J=9.3 Hz, 2H), 7.68-7.63 (m, 4H), 7.61-7.57 (m, 2H), 7.47-7.44 (m, 2H), 7.12-7.08 (m, 2H), 5.57-5.54 (m, 1H), 4.28 (s, 2H), 3.42-3.32 (m, 2H), 2.30-2.24 (m, 2H), 1.94-1.86 (m, 1H), 1.80-1.72 (m, 1H). $^{13}$C NMR (125 MHz, CD$_3$OD) δ 168.6, 164.0, 163.3, 162.0, 162.0, 161.8, 161.4, 153.9, 143.9, 136.0, 135.9, 131.9, 131.3, 128.8, 128.7, 128.1, 126.5, 125.8, 117.8, 115.5, 115.3, 113.8, 41.9, 38.7, 29.1, 23.6. HRMS m/z calculated for C$_{26}$H$_{25}$FClN$_5$O (M+H$^+$) 478.1804; found 478.1803.

(N1-[1,1'-Phenyl]benzoyl-N5-(2-fluoro-1-imino-ethyl)-1-(5,6-difluoro-1H-benzo[d]imidazol-2-yl)-L-ornithine) (5q)

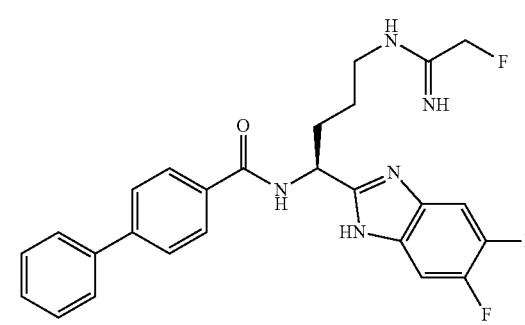

$^1$H NMR (CD$_3$OD; 500 MHz): δ 7.92 (d, J=9.4 Hz, 2H), 7.63 (d, J=9.4 Hz, 2H), 7.56-7.50 (m, 4H), 7.38-7.34 (m, 2H), 7.29-7.26 (m, 1H), 5.50-5.47 (m, 1H), 5.17 (d, J=45.3 Hz, 2H), 3.43-3.34 (m, 2H), 2.27-2.14 (m, 2H), 1.91-1.82 (m, 1H), 1.79-1.69 (m, 1H). $^{13}$C NMR (125 MHz, CD$_3$OD) δ 168.6, 163.1, 162.9, 161.4, 161.3, 160.8, 156.1, 150.0, 149.9, 148.1, 147.8, 144.9, 139.6, 131.6, 129.9, 128.7, 128.0, 127.8, 126.7, 102.3, 102.2, 78.3, 76.8, 41.5, 29.5, 23.7. HRMS m/z calculated for C$_{26}$H$_{24}$F$_3$N$_5$O (M+H$^+$) 480.2006; found 480.1998.

64

(N1-[1,1'-Phenyl]benzoyl-N5-(2-chloro-1-imino-ethyl)-1-(5,6-difluoro-1H-benzo[d]imidazol-2-yl)-L-ornithine) (5r)

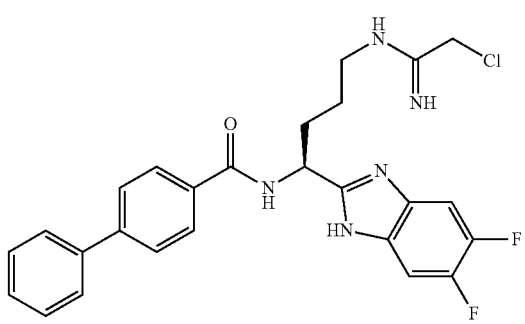 [SMILES: N=C(CF)NCCC[C@H](NC(=O)c1ccc(-c2ccccc2)cc1)c1nc2cc(F)c(F)cc2[nH]1]

$^1$H NMR (CD$_3$OD; 500 MHz): δ 7.92 (d, J=9.3 Hz, 2H), 7.63 (d, J=9.4 Hz, 2H), 7.56-7.49 (m, 4H), 7.37-7.34 (m, 2H), 7.29-7.26 (m, 1H), 5.50-5.47 (m, 1H), 4.27 (s, 2H), 3.38-3.33 (m, 2H), 2.28-2.15 (m, 2H), 1.90-1.82 (m, 1H), 1.79-1.71 (m, 1H). $^{13}$C NMR (125 MHz, CD$_3$OD) δ 168.6, 163.3, 161.3, 161.0, 156.2, 150.0, 149.8, 148.1, 147.9, 144.9, 139.6, 131.5, 129.9, 128.71, 128.0, 127.8, 126.7, 126.7, 102.4, 102.4, 102.3, 102.2, 42.0, 38.7, 29.5, 23.6. HRMS m/z calculated for C$_{26}$H$_{24}$F$_2$ClN$_5$O (M+H$^+$) 496.1710; found 496.1706.

(N1-4'-F-[1,1'-Phenyl]benzoyl-N5-(2-fluoro-1-iminoethyl)-1-(5,6-difluoro-1H-benzo[d]imidazol-2-yl)-L-ornithine) (5s)

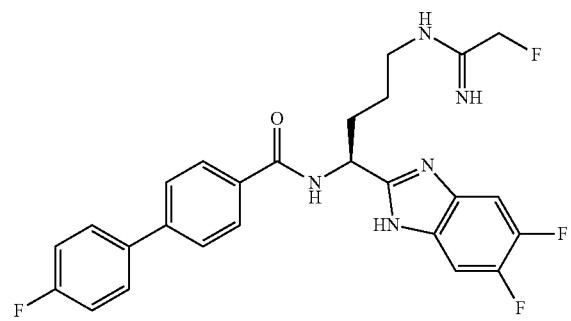 [SMILES: N=C(CF)NCCC[C@H](NC(=O)c1ccc(-c2ccc(F)cc2)cc1)c1nc2cc(F)c(F)cc2[nH]1]

$^1$H NMR (CD$_3$OD; 500 MHz): δ 7.93-7.90 (d, J=9.1 Hz, 2H), 7.63-7.60 (d, J=9.1 Hz, 2H), 7.59-7.55 (m, 2H), 7.52-7.49 (m, 2H), 7.11-7.07 (m, 2H), 5.49-5.46 (m, 1H), 5.16 (d, J=45.4 Hz, 2H), 3.42-3.33 (m, 2H), 2.28-2.14 (m, 2H), 1.92-1.81 (m, 1H), 1.79-1.70 (m, 1H). $^{13}$C NMR (125 MHz, CD$_3$OD) 168.6, 163.9, 163.1, 162.8, 162.1, 161.2, 161.0, 156.1, 150.0, 149.8, 148.0, 147.8, 143.8, 136.0, 131.6, 130.0, 128.7, 128.6, 128.0, 126.5, 115.5, 115.3, 102.4, 102.3, 102.3, 102.2, 78.3, 76.9, 41.4, 29.5, 23.8. HRMS m/z calculated for C$_{26}$H$_{23}$F$_4$N$_5$O (M+H$^+$) 498.1911; found 498.1903.

65

(N1-4'-F-[1,1'-Phenyl]benzoyl-N5-(2-chloro-1-iminoethyl)-1-(5,6-difluoro-1H-benzo[d]imidazol-2-yl)-L-ornithine) (5t)

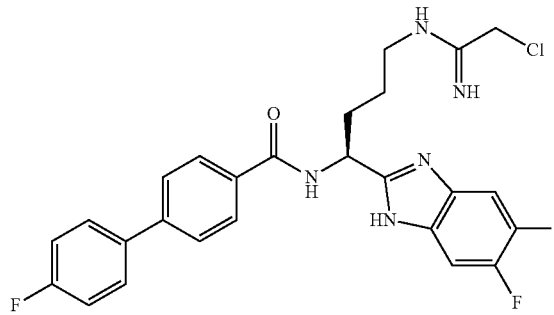

¹H NMR (CD₃OD; 500 MHz): δ 7.91 (d, J=9.4 Hz, 2H), 7.61 (d, J=9.3 Hz, 2H), 7.59-7.56 (m, 2H), 7.52-7.50 (m, 2H), 7.11-7.07 (m, 2H), 5.50-5.46 (m, 1H), 4.27 (s, 2H), 3.39-3.31 (m, 2H), 2.28-2.14 (m, 2H), 1.92-1.82 (m, 1H), 1.79-1.70 (m, 1H). ¹³C NMR (125 MHz, CD₃OD) δ 168.6, 163.9, 163.3, 162.0, 161.2, 160.9, 156.2, 150.0, 149.8, 148.0, 147.8, 143.8, 135.9, 131.6, 129.8, 128.7, 128.0, 126.6, 115.4, 115.3, 102.4, 102.3, 102.3, 102.2, 42.0, 38.7, 29.6, 23.6. HRMS m/z calculated for $C_{26}H_{23}F_3ClN_5O$ (M+H⁺) 514.1616; found 514.1612.

66

(N1-4'-ethynyl-[1,1'-Phenyl]benzol-N5-(2-chloro-1-iminoethyl)-1-(1H-benzo[d]imidazol-2-yl)-L-ornithine) (5v)

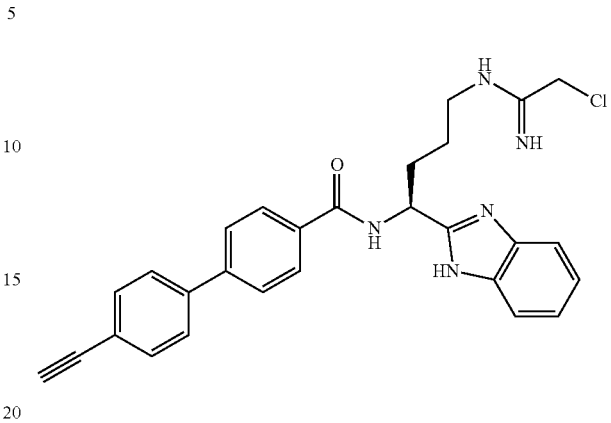

¹H NMR (CD₃OD; 400 MHz): δ 8.07 (d, J=8.4 Hz, 2H), 7.82-7.78 (m, 4H), 7.72-7.69 (m, 2H), 7.60-7.57 (m, 4H), 5.67 (t, J=7.6 Hz, 1H), 4.39 (s, 2H), 3.61 (s, 1H), 3.52-3.47 (m, 2H), 2.42-2.36 (m, 2H), 2.07-1.83 (m, 2H). ¹³C NMR (100 MHz, CD₃OD) b 170.0, 164.8, 155.3, 145.3, 141.2, 133.7, 133.3, 133.2, 129.6, 128.2, 128.1, 127.3, 123.7, 115.2, 84.0, 79.9, 43.4, 40.1, 30.5, 25.0. HRMS m/z calculated for $C_{28}H_{26}ClN_5O$ (M+H⁺) 484.1896; found 484.1902.

(N1-4'-ethynyl-[1,1'-Phenyl]benzol-N5-(2-fluoro-1-iminoethyl)-1-(1H-benzo[d]imidazol-2-yl)-L-ornithine) (5u)

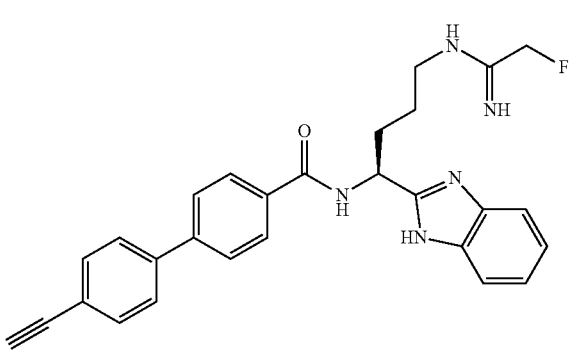 [SMILES: C#Cc1ccc(-c2ccc(C(=O)N[C@@H](CCCNC(=N)CF)c3nc4ccccc4[nH]3)cc2)cc1]

¹H NMR (CD₃OD; 400 MHz): δ 8.08 (d, J=8.4 Hz, 2H), 7.81-7.69 (m, 4H), 7.65-7.63 (m, 2H), 7.58-7.57 (m, 4H), 5.67 (t, J=7.6 Hz, 1H), 5.30 (d, J=45.2 Hz, 2H), 3.61 (s, 1H), 3.56-3.48 (m, 2H), 2.41-2.35 (m, 2H), 2.07-1.85 (m, 2H). ¹³C NMR (100 MHz, CD₃OD) δ 170.0, 164.5, 164.4, 163.2, 162.8, 155.4, 145.3, 141.2, 133.7, 133.4, 133.2, 129.9, 129.6, 128.2, 128.1, 127.2, 123.7, 115.2, 84.0, 79.9, 79.8, 78.1, 71.4, 55.8, 43.8, 42.8, 30.6, 25.1. HRMS m/z calculated for $C_{28}H_{26}FN_5O$ (M+H⁺) 468.2192; found 468.2191.

(N1-4-ethynyl-benzoyl-N5-(2-fluoro-1-iminoethyl)-1-(1-isopropyl-benzo[d]imidazol-2-yl)-L-ornithine) (5w)

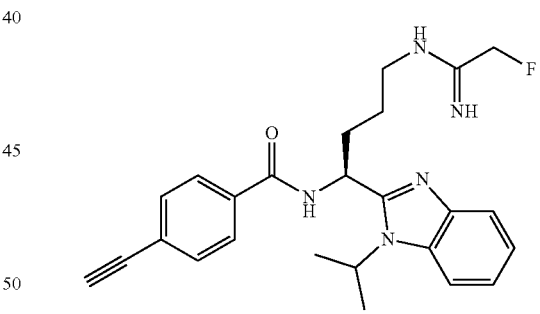

¹H NMR (CD₃OD; 500 MHz): δ 8.13-8.11 (m, 1H), 7.93 (d, J=8.3 Hz, 2H), 7.87-7.85 (m, 1H), 7.65-7.62 (m, 2H), 7.58 (d, J=8.3 Hz, 2H), 5.80-5.77 (m, 1H), 5.35-5.29 (m, 1H), 5.30 (d, J=45.5 Hz, 2H), 3.74 (s, 1H), 3.58-3.48 (m, 2H), 2.50-2.42 (m, 1H), 2.34-2.26 (m, 1H), 2.11-2.02 (m, 1H), 1.94-1.87 (m, 1H), 1.85 (d, J=6.8 Hz, 3H), 1.79 (d, J=7.2 Hz, 3H). ¹³C NMR (125 MHz, CD₃OD) δ 167.9, 163.1, 163.0, 161.1, 152.1, 132.4, 131.8, 131.5, 130.2, 127.5, 126.6, 126.3, 125.9, 114.8, 114.6, 81.9, 80.3, 78.3, 76.9, 51.4, 46.3, 41.4, 28.9, 23.8, 19.6. HRMS m/z calculated for $C_{25}H_{28}FN_5O$ (M+H⁺) 434.2349; found 434.2348.

4. General Procedure for Synthesis of Benzimidazole Haloacetamidines 6a-j.[a]

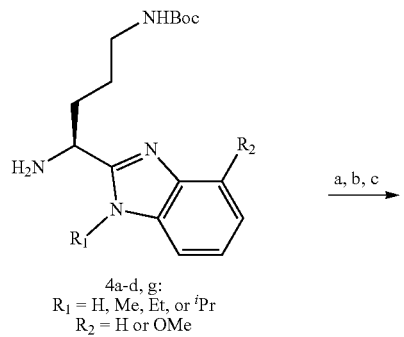

4a-d, g:
R₁ = H, Me, Et, or $^i$Pr
R₂ = H or OMe

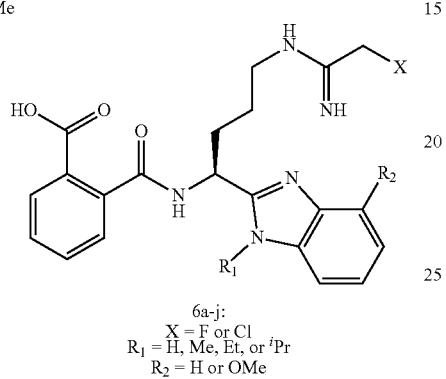

6a-j:
X = F or Cl
R₁ = H, Me, Et, or $^i$Pr
R₂ = H or OMe

[a]Reagents: (a) phthalic anhydride, THF; (b) TFA, CH₂Cl₂; (c) ethyl 2-haloacetimidate, TEA, MeOH To a stirred solution of 4a-d, g (1.0 eq) in THF was added phthalic anhydride (1.0 eq) and allowed to stir at rt under N₂ for 18 h. Solvents were evaporated and the crude product was purified by reverse phase HPLC using MeCN:H₂O (0.5% TFA) as the eluent to give the product in 78-86% yield. This product was then treated with TFA to remove the Boc group giving the desired 2-CO₂H-Bz-Orn-benzimidazole intermediate. The solvent was then evaporated to dryness and the crude material was dried in vacuo. To a stirred solution of the corresponding 2-CO₂H-Bz-Orn-benzimidazole intermediate in dry MeOH was added TEA (4.0 eq) followed by ethyl haloacetimidate HCl (2.0 eq). The reaction was stirred under N₂ at rt for 3 h. Solvents were then evaporated under reduced pressure and the crude product was purified by reverse phase HPLC using MeCN:H₂O (0.5% TFA) as an eluent to give compounds 6a-j in 52-69% yield.

(N1-(2-Carboxyl)benzol-N5-(2-fluoro-1-iminoethyl)-1-(1H-benzo[d]imidazol-2-yl)-L-ornithine)

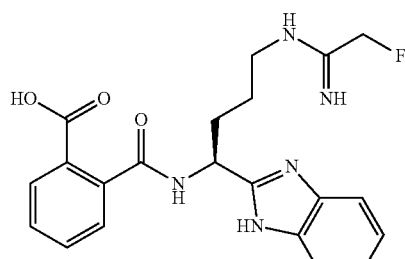

¹H NMR (CD₃OD; 400 MHz): δ 8.06 (dd, J=1.2 Hz, J=8.0 Hz, 2H), 7.84-7.79 (m, 2H), 7.71-7.67 (m, 1H), 7.63-7.56 (m, 4H), 5.59-5.54 (m, 1H), 5.26 (d, J=45.2 Hz, 2H), 3.52-3.48 (m, 2H), 2.38-2.23 (m, 2H), 2.09-1.89 (m, 2H). ¹³C NMR (100 MHz, CD₃OD) δ 173.5, 169.4, 164.8, 162.9, 162.6, 154.6, 139.0, 133.6, 133.3, 131.7, 131.2, 130.3, 128.9, 127.2, 115.2, 79.8, 78.1, 42.8, 30.5, 25.1. HRMS m/z calculated for C₂₁H₂₃FN₅O₃ (M+H⁺–H₂O) 394.1674; found 394.1673.

(N1-(2-Carboxyl)benzol-N5-(2-chloro-1-iminoethyl)-1-(1H-benzo[d]imidazol-2-yl)-L-ornithine) (6b)

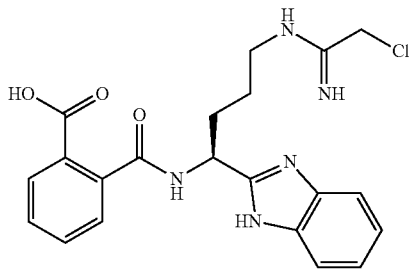 [SMILES: N=C(CCl)NCCC[C@H](NC(=O)c1ccccc1C(=O)O)c1nc2ccccc2[nH]1]

¹H NMR (CD₃OD; 400 MHz): δ 8.07 (dd, J=1.2 Hz, J=8.0 Hz, 2H), 7.83-7.79 (m, 2H), 7.72-7.67 (m, 1H), 7.64-7.57 (m, 4H), 5.57-5.54 (m, 1H), 4.41 (s, 2H), 3.50-3.46 (m, 2H), 2.39-2.24 (m, 2H), 2.09-1.88 (m, 2H). ¹³C NMR (100 MHz, CD₃OD) δ 173.5, 169.4, 164.8, 162.9, 162.6, 154.6, 139.0, 133.6, 133.3, 131.7, 131.2, 130.3, 128.9, 127.2, 115.2 (2C), 43.3, 40.1, 30.2 (2C), 24.9. HRMS m/z calculated for C₂₁H₂₃ClN₅O₃ (M+H–H₂O) 410.1378; found 410.1382.

(N1-(2-Carboxyl)benzoyl-N5-(2-fluoro-1-iminoethyl)-1-(1-methyl-benzo[d]imidazol-2-yl)-L-ornithine) (6c)

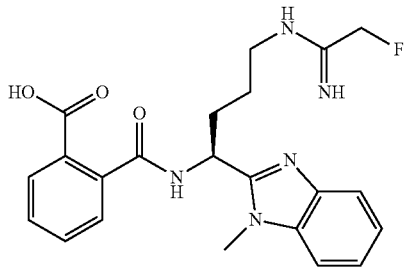 [SMILES: Cn1c([C@H](CCCNC(=N)CF)NC(=O)c2ccccc2C(=O)O)nc2ccccc21]

¹H NMR (CD₃OD; 400 MHz): δ 7.99 (dd, J=1.4 Hz, J=7.8 Hz, 1H), 7.86 (dd, J=2.2 Hz, J=7.1 Hz, 1H), 7.80 (dd, J=2.2 Hz, J=7.2 Hz, 1H), 7.66-7.54 (m, 4H), 7.49 (dd, J=1.4 Hz, J=7.5 Hz, 1H), 5.68-5.64 (m, 1H), 5.28 (d, J=45.3 Hz, 2H), 4.19 (s, 3H), 3.52-3.46 (m, 2H), 2.41-2.31 (m, 1H), 2.29-2.21 (m, 1H), 2.09-1.99 (m, 1H), 1.96-1.86 (m, 1H). ¹³C NMR (100 MHz, CD₃OD) δ 171.7, 166.0, 160.6, 156.0, 151.9, 137.4, 131.8, 130.0, 129.7, 127.3, 125.7, 125.5, 114.9, 111.8, 110.5, 78.3, 76.6, 45.3, 41.3, 30.6, 28.3, 23.6. HRMS m/z calculated for C₂₂H₂₄FN₅O₃ (M+H⁺) 426.1936; found 426.1938.

(N1-(2-Carboxyl)benzoyl-N5-(2-chloro-1-iminoethyl)-1-(1-methyl-benzo[d]imidazol-2-yl)-L-ornithine) (6d)

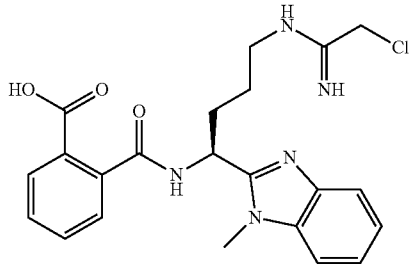 [SMILES: Cn1c([C@H](CCCNC(=N)CCl)NC(=O)c2ccccc2C(=O)O)nc2ccccc21]

$^1$H NMR (CD$_3$OD; 400 MHz): δ 7.99 (dd, J=1.4 Hz, J=7.5 Hz, 1H), 7.83 (dd, J=2.3 Hz, J=7.2 Hz, 1H), 7.78 (dd, J=1.8 Hz, J=7.2 Hz, 1H), 7.66-7.54 (m, 4H), 7.48 (dd, J=1.4 Hz, J=7.4 Hz, 1H), 5.67-5.63 (m, 1H), 4.38 (s, 2H), 4.17 (s, 3H), 3.49-3.45 (m, 2H), 2.41-2.23 (m, 2H), 2.07-1.98 (m, 1H), 1.94-1.87 (m, 1H). $^{13}$C NMR (100 MHz, CD$_3$OD) δ 171.1, 167.3, 161.9, 152.1, 137.5, 133.9, 133.7, 132.0, 130.2, 129.6, 127.3, 125.3, 115.2, 111.6, 109.9, 108.9, 101.1, 100.5, 45.3, 42.0, 30.6, 23.5. HRMS m/z calculated for C$_{22}$H$_{24}$ClN$_5$O$_3$ (M+H$^+$) 442.1640; found 442.1642.

(N1-(2-Carboxyl)benzoyl-N5-(2-fluoro-1-iminoethyl)-1-(1-ethyl-benzo[d]imidazol-2-yl)-L-ornithine) (6e)

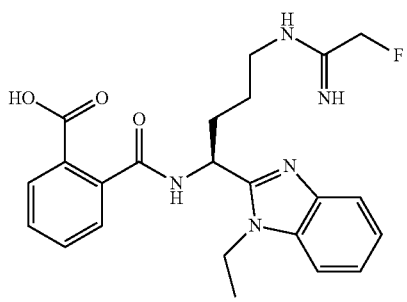 [SMILES: CCn1c([C@H](CCCNC(=N)CF)NC(=O)c2ccccc2C(=O)O)nc2ccccc21]

$^1$H NMR (CD$_3$OD; 400 MHz): δ 7.99 (dd, J=1.6 Hz, J=7.4 Hz, 1H), 7.90 (dd, J=2.2 Hz, J=7.4 Hz, 1H), 7.82 (dd, J=2.2 Hz, J=7.3 Hz, 1H), 7.66-7.54 (m, 4H), 7.48 (dd, J=1.6 Hz, J=7.4 Hz, 1H), 5.66-5.62 (m, 1H), 5.28 (d, J=45.5 Hz, 2H), 4.70-4.61 (m, 2H), 3.52-3.41 (m, 2H), 2.40-2.20 (m, 2H), 2.09-1.98 (m, 1H), 1.94-1.83 (m, 1H), 1.59 (t, J=7.1 Hz, 3H). $^{13}$C NMR (100 MHz, CD$_3$OD) δ 171.3, 167.1, 160.1, 151.5, 137.2, 131.8, 129.8, 129.6, 128.8, 128.4, 126.8, 1260.0, 125.6, 125.6, 114.9, 111.9, 78.0, 45.1, 41.2, 40.2, 29.0, 23.4, 13.2. HRMS m/z calculated for C$_{23}$H$_{26}$FN$_5$O$_3$ (M+H$^+$) 440.2092; found 440.2092.

(N1-(2-Carboxyl)benzoyl-N5-(2-chloro-1-iminoethyl)-1-(1-ethyl-benzo[d]imidazol-2-yl)-L-ornithine) (6f)

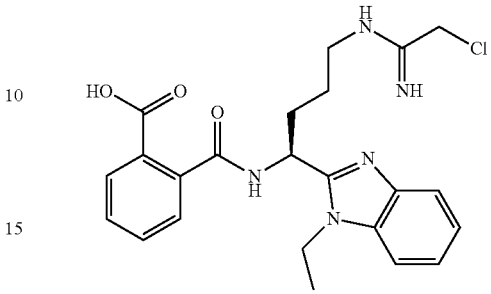

$^1$H NMR (CD$_3$OD; 400 MHz): δ 7.99 (dd, J=1.3 Hz, J=7.4 Hz, 1H), 7.88 (dd, J=1.7 Hz, J=7.1 Hz, 1H), 7.81 (dd, J=2.1 Hz, J=7.1 Hz, 1H), 7.65-7.54 (m, 4H), 7.47 (dd, J=1.7 Hz, J=7.1 Hz, 1H), 5.65-5.61 (m, 1H), 4.68-4.59 (m, 2H), 4.37 (s, 2H), 3.47-3.41 (m, 2H), 2.40-2.21 (m, 2H), 2.09-1.98 (m, 1H), 1.95-1.85 (m, 1H), 1.60 (t, J=7.2 Hz, 3H). $^{13}$C NMR (100 MHz, CD$_3$OD) δ 171.2, 167.0, 151.5, 137.3, 137.1, 132.1, 129.7, 129.1, 128.7, 127.8, 127.2, 125.3, 125.0, 115.1, 111.5, 87.0, 45.0, 41.7, 38.5, 28.5, 28.1, 23.3, 13.5. HRMS m/z calculated for C$_{23}$H$_{26}$ClN$_5$O$_3$ (M+H$^+$) 456.1797; found 456.1799.

(N1-(2-Carboxyl)benzoyl-N5-(2-fluoro-1-iminoethyl)-1-(1-isopropyl-benzo[d]imidazol-2-yl)-L-ornithine) (6g)

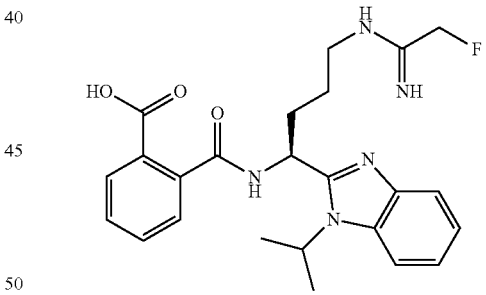

$^1$H NMR (CD$_3$OD; 400 MHz): δ 8.05-8.02 (m, 1H), 7.99 (dd, J=1.7 Hz, J=7.6 Hz, 1H), 7.82-7.78 (m, 2H), 7.65-7.52 (m, 4H), 7.47 (dd, J=1.7 Hz, J=7.5 Hz, 1H), 5.67-5.63 (m, 1H), 5.27 (d, J=45.3 Hz, 2H), 5.31-5.25 (m, 1H), 3.53-3.43 (m, 2H), 2.37-2.20 (m, 2H), 2.07-1.96 (m, 1H), 1.93-1.85 (m, 1H), 1.82 (d, J=2.4 Hz, 3H), 1.80 (d, J=2.3 Hz, 3H). $^{13}$C NMR (100 MHz, CD$_3$OD) δ 171.4, 167.5, 151.3, 137.1, 131.8, 130.1, 129.6, 129.1, 127.2, 125.9, 124.9, 115.7, 115.6, 114.1, 110.0, 78.3, 76.7, 50.5, 45.6, 41.4, 29.0, 23.5, 19.9, 19.8. HRMS m/z calculated for C$_{24}$H$_{28}$FN$_5$O$_3$ (M+H$^+$) 454.2249; found 454.2249.

71

(N1-(2-Carboxyl)benzoyl-N5-(2-chloro-1-imino-ethyl)-1-(1-isopropyl-benzo[d]imidazol-2-yl)-L-ornithine) (6h)

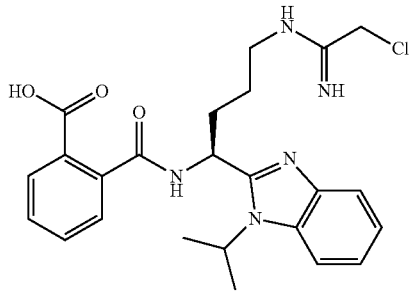 [SMILES: CC(C)n1c([C@H](CCCNC(=N)CCl)NC(=O)c2ccccc2C(=O)O)nc2ccccc21]

¹H NMR (CD₃OD; 400 MHz): δ 8.10-8.07 (m, 1H), 7.99 (dd, J=1.7 Hz, J=7.4 Hz, 1H), 7.86-7.81 (m, 1H), 7.66-7.54 (m, 4H), 7.48 (dd, J=1.6 Hz, J=7.4 Hz, 1H), 5.70-5.66 (m, 1H), 5.37-5.30 (m, 1H), 4.37 (s, 2H), 3.47-3.43 (m, 2H), 2.39-2.19 (m, 2H), 2.09-1.98 (m, 1H), 1.93-1.82 (m, 1H), 1.84 (d, J=2.5 Hz, 3H), 1.82 (d, J=2.5 Hz, 3H). ¹³C NMR (100 MHz, CD₃OD) δ 171.6, 167.4, 163.2, 151.1, 136.9, 131.8, 130.4, 130.1, 129.5, 129.1, 127.2, 125.7, 125.3, 114.9, 114.5, 111.0, 50.8, 45.7, 41.7, 38.4, 28.9, 23.5, 19.8, 19.8. HRMS m/z calculated for $C_{24}H_{28}ClN_5O_3$ (M+H⁺) 470.1953; found 470.1959.

(N1-(2-Carboxyl)benzoyl-N5-(2-fluoro-1-imino-ethyl)-1-(4-methoxy-1-methyl-benzo[d]imidazol-2-yl)-L-ornithine) (6i)

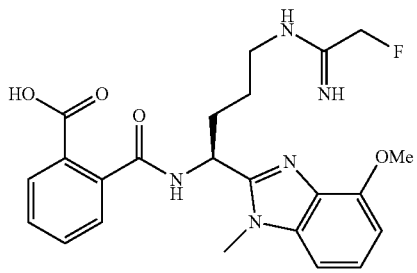 [SMILES: COc1cccc2c1nc([C@H](CCCNC(=N)CF)NC(=O)c1ccccc1C(=O)O)n2C]

¹H NMR (CD₃OD; 400 MHz): δ 7.98 (dd, J=1.6 Hz, J=7.6 Hz, 1H), 7.65-7.61 (m, 1H), 7.57-7.47 (m, 3H), 7.40 (d, J=8.2 Hz, 1H), 7.11 (d, J=8.2 Hz, 1H), 5.63-5.59 (m, 1H), 5.27 (d, J=45.4 Hz, 2H), 4.17 (s, 3H), 4.05 (s, 3H), 3.50-3.45 (m, 2H), 2.40-2.30 (m, 1H), 2.29-2.18 (m, 1H), 2.08-1.96 (m, 1H), 1.89-1.77 (m, 1H). ¹³C NMR (100 MHz, CD₃OD) δ 171.6, 166.7, 162.8, 160.9, 150.8, 148.2, 137.4, 134.5, 131.7, 129.8, 129.3, 128.6, 127.1, 126.6, 105.6, 103.4, 78.0, 76.2, 55.0, 45.5, 41.3, 30.5, 28.1, 23.2. HRMS m/z calculated for $C_{23}H_{26}FN_5O_4$ (M+H⁺) 456.2042; found 456.2039.

(N1-(2-Carboxyl)benzoyl-N5-(2-fluoro-1-imino-ethyl)-1-(4-methoxy-1-methyl-benzo[d]imidazol-2-yl)-L-ornithine) (6j)

¹H NMR (CD₃OD; 400 MHz): δ 7.99 (dd, J=1.6 Hz, J=7.6 Hz, 1H), 7.65-7.61 (m, 1H), 7.58-7.47 (m, 3H), 7.39 (d, J=8.3 Hz, 1H), 7.10 (d, J=8.1 Hz, 1H), 5.63-5.59 (m, 1H), 4.39 (s, 2H), 4.16 (s, 3H), 4.05 (s, 3H), 3.47-3.43 (m, 2H), 2.40-2.30 (m, 1H), 2.29-2.20 (m, 1H), 2.08-1.96 (m, 1H), 1.89-1.78 (m, 1H). ¹³C NMR (100 MHz, CD₃OD) δ 171.7, 167.2, 163.2, 150.9, 147.9, 137.2, 134.5, 132.0, 130.0, 129.6, 128.8, 127.2, 126.9, 115.0, 106.0, 103.6, 55.1, 45.6, 42.0, 38.4, 31.1, 28.0, 23.5. HRMS m/z calculated for $C_{23}H_{26}FN_5O_4$ (M+H⁺) 472.1745; found 472.1746.

3. General Procedure for Synthesis of Benzimidazole Haloacetamidines 7a-v.[a]

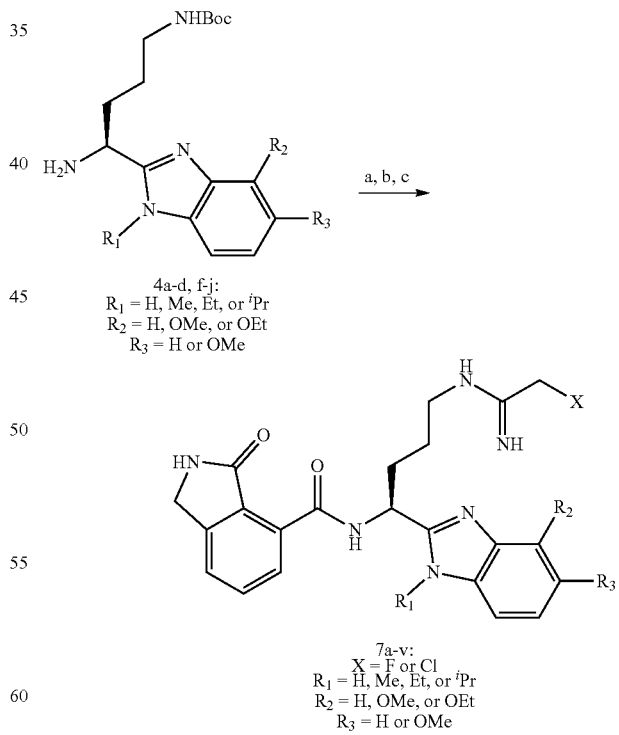

[a]Reagents: (a) 3-oxo-2,3-dihydro-1H-isoindole-4-carboxylic acid, HOBt, HBTU, DIPEA, DMF; (b) 2M HCl/Et₂O; (c) ethyl 2-haloacetimidate, TEA, MeOH To a stirred solution of 4a-d, f-j (1.0 eq) in DMF was added HOBt (2.0 eq), HBTU (2.0 eq), and DIPEA (3.0 eq) followed by 3-oxo-2,3-dihydro-1H-isoindole-4-carboxylic acid (1.0 eq) and allowed to stir at rt for 12 h. The reaction mixture was then diluted with water. The product was filtered, washed with water, dried under vacuum, and obtained in 62-71% yield. This product was then treated with 2 M HCl in Et$_2$O to remove the Boc group giving the Oxoisoindoline-Orn-benzimidazole intermediate. The solvent was then evaporated to dryness and the crude material was dried in vacuo. To a stirred solution of the corresponding Oxoisoindoline-Orn-benzimidazole intermediate in dry MeOH was added TEA (4.0 eq) followed by ethyl haloacetimidate HCl (2.0 eq). The reaction was stirred under N$_2$ at rt for 3 h. Solvents were then evaporated under reduced pressure and the crude product was purified by reverse phase HPLC using MeCN:H$_2$O (0.5% TFA) as an eluent to give compounds 7a-v in 41-57% yield.

(N1-(3-oxoisoindoline)benzol-N5-(2-fluoro-1-iminoethyl)-1-(1H-benzo[d]imidazol-2-yl)-L-ornithine) (7a)

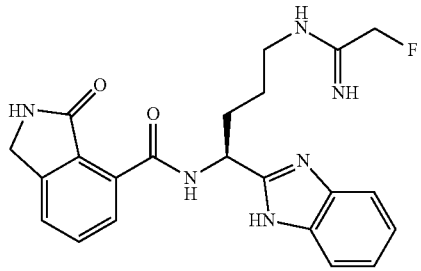 [SMILES: N=C(CF)NCCC[C@H](NC(=O)c1cccc2c1C(=O)NC2)c1nc2ccccc2[nH]1]

$^1$H NMR (CD$_3$OD; 400 MHz): δ 8.18 (d, J=8.3 Hz, 1H), 7.83 (dd, J=1.6 Hz, J=8.3 Hz, 1H), 7.79-7.74 (m, 3H), 7.59-7.55 (m, 2H), 5.59-5.56 (m, 1H), 5.29 (d, J=45.3 Hz, 2H), 4.59 (s, 2H), 3.53-3.45 (m, 2H), 2.38-2.27 (m, 2H), 2.04-1.91 (m, 2H). $^{13}$C NMR (100 MHz, CD$_3$OD) δ 170.1, 166.6, 163.1, 154.3, 146.2, 131.8, 130.7, 130.2, 130.0, 128.8, 127.1, 126.9, 125.9, 118.0, 113.6, 102.5, 78.4, 76.7, 45.5, 41.2, 29.6, 23.7. HRMS m/z calculated for C$_{22}$H$_{23}$FN$_6$O$_2$ (M+H$^+$) 423.1939; found 423.1941.

(N1-(3-oxoisoindoline)benzol-N5-(2-chloro-1-iminoethyl)-1-(1H-benzo[d]imidazol-2-yl)-L-ornithine) (7b)

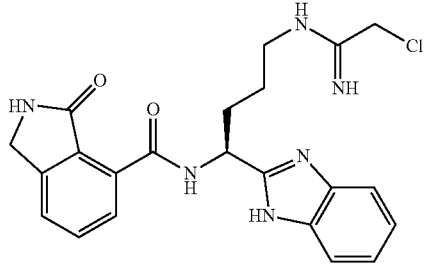 [SMILES: N=C(CCl)NCCC[C@H](NC(=O)c1cccc2c1C(=O)NC2)c1nc2ccccc2[nH]1]

$^1$H NMR (CD$_3$OD; 400 MHz): δ 8.20 (d, J=8.2 Hz, 1H), 7.83 (dd, J=1.6 Hz, J=7.7 Hz, 1H) 7.79-7.70 (m, 3H), 7.54-7.51 (m, 2H), 5.58-5.54 (m, 1H), 4.59 (s, 2H), 4.39 (s, 2H), 3.48-3.43 (m, 2H), 2.44-2.28 (m, 2H), 2.04-1.91 (m, 2H). $^{13}$C NMR (100 MHz, CD$_3$OD) δ 172.0, 163.3, 154.1, 146.1, 131.8, 131.5, 130.7, 130.2, 130.0, 128.8, 127.9, 127.1, 125.9, 125.8, 113.5, 110.0, 45.5, 43.1, 41.8, 38.8, 29.5, 23.6. HRMS m/z calculated for C$_{22}$H$_{23}$ClN$_6$O$_2$ (M+H$^+$) 439.1644; found 439.1646.

(N1-(3-oxoisoindoline)benzol-N5-(2-chloro-1-iminoethyl)-1-(1-methyl-benzo[d]imidazol-2-yl)-L-ornithine) (7c)

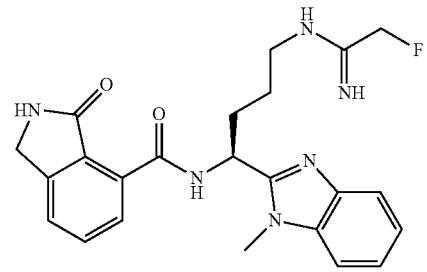 [SMILES: Cn1c([C@H](CCCNC(=N)CF)NC(=O)c2cccc3c2C(=O)NC3)nc2ccccc21]

$^1$H NMR (CD$_3$OD; 400 MHz): δ 8.18 (dd, J=1.3 Hz, J=7.5 Hz, 1H), 7.91 (dd, J=1.6 Hz, J=7.2 Hz, 1H), 7.82 (dd, J=1.6 Hz, J=7.5 Hz, 1H), 7.75 (t, J=7.8 Hz, 2H), 7.67-7.58 (m, 2H), 5.65-5.62 (m, 1H), 5.30 (d, J=45.4 Hz, 2H), 4.58 (s, 2H), 4.21 (s, 3H), 3.54-3.44 (m, 2H), 2.37-2.25 (m, 2H), 2.13-2.03 (m, 1H), 2.02-1.93 (m, 1H). $^{13}$C NMR (100 MHz, CD$_3$OD) δ 171.9, 166.2, 153.2, 146.3, 132.9, 131.7, 130.3, 130.1, 128.8, 127.2, 126.4, 126.0, 113.8, 112.3, 109.8, 78.5, 76.7, 45.4, 41.2, 37.3, 30.7, 28.6, 23.6. HRMS m/z calculated for C$_{23}$H$_{25}$FN$_6$O$_2$ (M+H$^+$) 437.2096; found 437.2095.

(N1-(3-oxoisoindoline)benzol-N5-(2-chloro-1-iminoethyl)-1-(1-methyl-benzo[d]imidazol-2-yl)-L-ornithine) (7d)

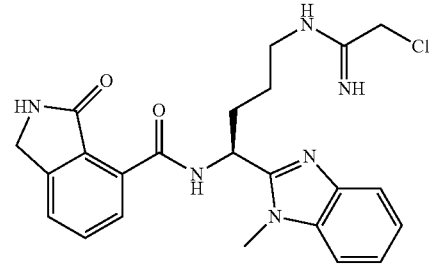 [SMILES: Cn1c([C@H](CCCNC(=N)CCl)NC(=O)c2cccc3c2C(=O)NC3)nc2ccccc21]

$^1$H NMR (CD$_3$OD; 400 MHz): δ 8.18 (dd, J=1.3 Hz, J=7.6 Hz, 1H), 7.91 (dd, J=1.2 Hz, J=7.5 Hz, 1H), 7.82 (dd, J=1.4 Hz, J=7.6 Hz, 1H), 7.74 (t, J=7.8 Hz, 2H), 7.66-7.58 (m, 2H), 5.66-5.62 (m, 1H), 4.58 (s, 2H), 4.41 (s, 2H), 4.21 (s, 3H), 3.51-3.44 (m, 2H), 2.37-2.26 (m, 2H), 2.13-1.93 (m, 2H). $^{13}$C NMR (100 MHz, CD$_3$OD) δ 171.9, 166.3, 163.4, 153.4, 146.3, 132.9, 131.8, 130.8, 130.3, 130.1, 128.9, 127.2, 126.4, 126.0, 114.0, 112.2, 46.7, 45.4, 41.8, 38.8, 30.7, 28.7, 23.6. HRMS m/z calculated for C$_{23}$H$_{25}$ClN$_6$O$_2$ (M+H$^+$) 453.1800; found 453.1799.

75

(N1-(3-oxoisoindoline)benzoyl-N5-(2-fluoro-1-iminoethyl)-1-(1-ethyl-benzo[d]imidazol-2-yl)-L-ornithine) (7e)

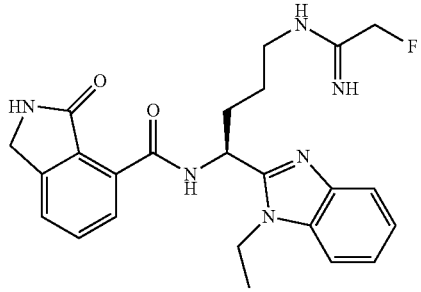 [SMILES: CCn1c([C@H](CCCNC(=N)CF)NC(=O)c2cccc3c2C(=O)NC3)nc2ccccc21]

¹H NMR (CD₃OD; 400 MHz): δ 8.20 (dd, J=1.6 Hz, J=7.6 Hz, 1H), 7.94 (dd, J=1.6 Hz, J=7.4 Hz, 1H), 7.83 (dd, J=1.2 Hz, J=7.6 Hz, 1H), 7.77-7.72 (m, 2H), 7.66-7.58 (m, 2H), 5.65-5.62 (m, 1H), 5.30 (d, J=45.4 Hz, 2H), 4.78-4.65 (m, 2H), 4.58 (s, 2H), 3.54-3.44 (m, 2H), 2.38-2.22 (m, 2H), 2.14-1.95 (m, 2H), 1.62 (t, J=7.4 Hz, 3H). ¹³C NMR (100 MHz, CD₃OD) δ 171.9, 168.7, 165.9, 164.2, 156.4, 152.5, 145.9, 143.4, 131.6, 130.3, 130.1, 128.7, 127.7, 127.1, 126.3, 125.9, 114.1, 112.3, 45.3, 41.2, 40.4, 29.2, 23.8, 13.2. HRMS m/z calculated for $C_{24}H_{27}FN_6O_2$ (M+H⁺) 451.2252; found 451.2250.

(N1-(3-oxoisoindoline)benzol-N5-(2-chloro-1-iminoethyl)-1-(1-ethyl-benzo[d]imidazol-2-yl)-L-ornithine) (7f)

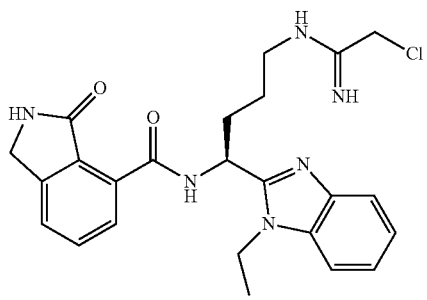 [SMILES: CCn1c([C@H](CCCNC(=N)CCl)NC(=O)c2cccc3c2C(=O)NC3)nc2ccccc21]

¹H NMR (CD₃OD; 400 MHz): δ 8.19 (dd, J=1.5 Hz, J=7.3 Hz, 1H), 7.94 (dd, J=1.5 Hz, J=7.5 Hz, 1H), 7.82 (dd, J=1.3 Hz, J=7.3 Hz, 1H), 7.77-7.72 (m, 2H), 7.66-7.58 (m, 2H), 5.66-5.62 (m, 1H), 4.78-4.65 (m, 2H), 4.58 (s, 2H), 4.41 (s, 2H), 3.52-3.43 (m, 2H), 2.38-2.23 (m, 2H), 2.15-1.96 (m, 2H), 1.62 (t, J=7.4 Hz, 3H). ¹³C NMR (100 MHz, CD₃OD) δ 171.8, 166.1, 163.3, 159.2, 158.2, 153.0, 146.3, 131.8, 130.3, 128.8, 127.4, 126.3, 126.0, 116.5, 114.1, 112.4, 72.1, 45.4, 41.9, 40.5, 38.8, 29.2, 23.6, 13.3. HRMS m/z calculated for $C_{24}H_{27}ClN_6O_2$ (M+H⁺) 467.1957; found 467.1952.

76

(N1-(3-oxoisoindoline)benzol-N5-(2-fluoro-1-iminoethyl)-1-(1-isopropyl-benzo[d]imidazol-2-yl)-L-ornithine) (7g)

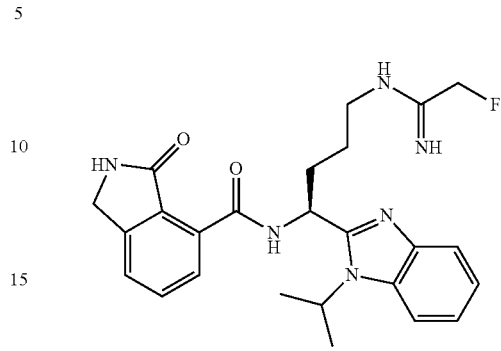

¹H NMR (CD₃OD; 500 MHz): δ 8.21 (dd, J=1.5 Hz, J=7.7 Hz, 1H), 8.14 (dd, J=1.5 Hz, J=7.5 Hz, 1H), 7.85 (dd, J=1.4 Hz, J=7.4 Hz, 1H), 7.80-7.76 (m, 2H), 7.66-7.61 (m, 2H), 5.73-5.70 (m, 1H), 5.37-5.31 (m, 1H), 5.34 (d, J=45.3 Hz, 2H), 4.61 (s, 2H), 3.60-3.49 (m, 2H), 2.40-2.22 (m, 2H), 2.15-2.07 (m, 1H), 2.06-1.99 (m, 1H), 1.88 (d, J=1.8 Hz, 3H), 1.86 (d, J=1.6 Hz, 3H). ¹³C NMR (125 MHz, CD₃OD) δ 171.8, 166.3, 163.2, 160.5, 160.1, 152.8, 146.4, 131.9, 131.3, 130.4, 130.3, 128.9, 127.2, 126.2, 125.7, 114.8, 114.3, 78.3, 77.0, 51.3, 45.5, 41.1, 29.3, 23.8, 19.5. HRMS m/z calculated for $C_{25}H_{29}FN_6O_2$ (M+H⁺) 465.2409; found 465.2409.

(N1-(3-oxoisoindoline)benzol-N5-(2-chloro-1-iminoethyl)-1-(1-isopropyl-benzo[d]imidazol-2-yl)-L-ornithine) (7h)

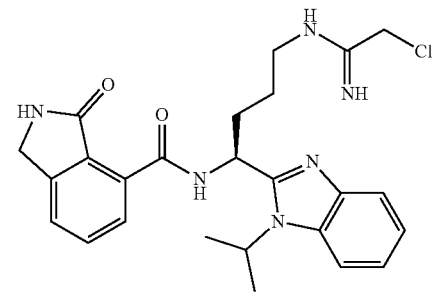 [SMILES: CC(C)n1c([C@H](CCCNC(=N)CCl)NC(=O)c2cccc3c2C(=O)NC3)nc2ccccc21]

¹H NMR (CD₃OD; 500 MHz): δ 8.21 (dd, J=1.3 Hz, J=7.4, Hz, 1H), 8.14 (dd, J=2.0 Hz, J=7.6 Hz, 1H), 7.86 (dd, J=1.6 Hz, J=7.3 Hz, 2H), 7.80-7.76 (m, 2H), 7.66-7.61 (m, 2H), 5.73-5.70 (m, 1H), 5.37-5.32 (m, 1H), 4.61 (s, 2H), 4.45 (s, 2H), 3.57-3.47 (m, 2H), 2.4-2.25 (m, 2H), 2.16-2.08 (m, 1H), 2.07-1.98 (m, 1H), 1.88 (d, J=3.6 Hz, 3H), 1.86 (d, J=3.5 Hz, 3H). ¹³C NMR (125 MHz, CD₃OD) 171.9, 166.3, 163.4, 160.6, 160.4, 152.7, 146.2, 131.9, 131.3, 130.3, 130.2, 128.9, 127.3, 126.2, 125.8, 114.7, 114.4, 51.3, 47.2, 45.4, 41.8, 38.7, 29.3, 23.7, 19.5. HRMS m/z calculated for $C_{25}H_{29}ClN_6O_2$ (M+H⁺) 481.2113; found 481.2112.

77

(N1-(3-oxoisoindoline)benzol-N5-(2-fluoro-1-iminoethyl)-1-(4-methoxy-1H-benzo[d]imidazol-2-yl)-L-omithine) (7i)

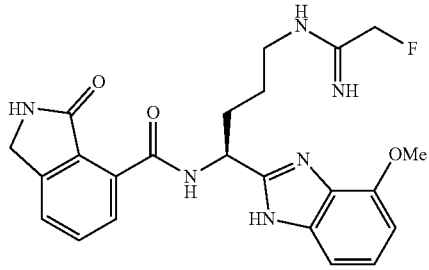

¹H NMR (CD₃OD; 400 MHz): δ 8.10 (dd, J=9.2 Hz, 1H), 7.73 (dd, J=9.3 Hz, 1H), 7.68-7.65 (m, 1H), 7.38-7.35 (m, 1H), 7.17 (dd, J=9.4 Hz, 1H), 6.98 (dd, J=9.2 Hz, 1H), 5.41-5.38 (m, 1H), 5.18 (d, J=45.5 Hz, 2H), 4.49 (s, 2H), 3.95 (s, 3H), 3.41-3.34 (m, 2H), 2.23-2.18 (m, 2H), 1.93-1.79 (m, 2H). ¹³C NMR (100 MHz, CD₃OD) δ 171.9, 166.5, 161.2, 153.6, 147.8, 146.1, 133.0, 131.8, 130.6, 130.2, 128.8, 127.1, 126.9, 105.9, 105.3, 100.0, 78.3, 76.9, 55.3, 45.5, 41.3, 29.9, 23.7. HRMS m/z calculated for C₂₃H₂₅FN₆O₃ (M+H⁺) 453.2045; found 453.2042.

(N1-(3-oxoisoindoline)benzoyl-N5-(2-chloro-1-iminoethyl)-1-(4-methoxy-1H-benzo[d]imidazol-2-yl)-L-ornithine) (7j)

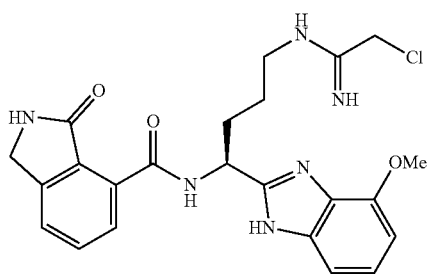 [SMILES: COc1cccc2[nH]c([C@H](CCCNC(=N)CCl)NC(=O)c3cccc4c3C(=O)NC4)nc12]

¹H NMR (CD₃OD; 500 MHz) δ 8.11 (dd, J=1.1 Hz, J=7.8 Hz, 1H), 7.73 (dd, J=1.1 Hz, J=7.6 Hz, 1H), 7.67 (t, J=7.8 Hz 1H), 7.36 (t, J=8.3 Hz, 1H), 7.17 (d, J=8.6 Hz, 1H), 6.97 (d, J=8.1 Hz, 1H), 5.41-5.38 (m, 1H), 4.49 (s, 2H), 4.29 (s, 2H), 3.95 (s, 3H), 3.39-3.33 (m, 2H), 2.23-2.19 (m, 2H), 1.93-1.80 (m, 2H). ¹³C NMR (125 MHz, CD₃OD) δ 171.4, 166.1, 163.6, 154.1, 153.6, 146.1, 131.6, 130.7, 130.3, 129.6, 128.6, 127.2, 126.6, 105.8, 105.5, 100.0, 74.3, 55.1, 45.1, 41.8, 38.4, 29.2, 23.5. HRMS m/z calculated for C₂₃H₂₅ClN₆O₃ (M+H⁺) 469.1749; found 469.1750.

78

(N1-(3-oxoisoindoline)benzoyl-N5-(2-fluoro-1-iminoethyl)-1-(4-methoxy-1-methyl-benzo[d]imidazol-2-yl)-L-ornithine) (7k)

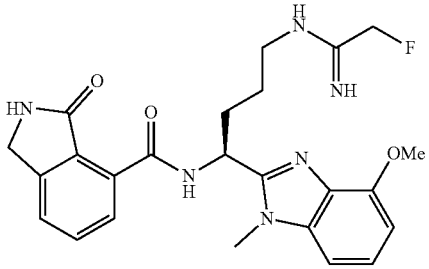 [SMILES: COc1cccc2c1nc([C@H](CCCNC(=N)CF)NC(=O)c1cccc3c1C(=O)NC3)n2C]

¹H NMR (CD₃OD; 400 MHz): δ 8.20 (dd, J=1.2 Hz, J=7.8 Hz, 1H), 7.81 (dd, J=1.3 Hz, J=7.6 Hz, 1H), 7.74 (t, J=7.6 Hz, 1H), 7.53 (t, J=8.2 Hz, 1H), 7.41 (d, J=8.5 Hz, 1H), 7.10 (d, J=8.2 Hz), 5.60-5.56 (m, 1H), 5.30 (d, J=45.3 Hz, 2H), 4.56 (s, 2H), 4.16 (s, 3H), 4.00 (s, 3H), 3.54-3.43 (m, 2H), 2.40-2.23 (m, 2H), 2.12-2.01 (m, 1H), 1.98-1.87 (m, 1H). ¹³C NMR (100 MHz, CD₃OD) δ 171.8, 166.0, 160.8, 152.4, 148.1, 146.1, 134.3, 131.6, 130.3, 130.0, 128.9, 127.2, 126.8, 109.8, 106.2, 103.9, 78.3, 76.7, 55.3, 45.4, 41.2, 30.8, 28.8, 23.6. HRMS m/z calculated for C₂₄H₂₇FN₆O₃ (M+H⁺) 467.2201; found 467.2201.

(N1-(3-oxoisoindoline)benzoyl-N5-(2-chloro-1-iminoethyl)-1-(4-methoxy-1-methyl-benzo[d]imidazol-2-yl)-L-ornithine) (7l)

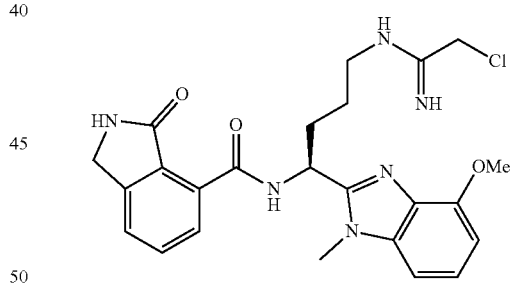

¹H NMR (CD₃OD; 400 MHz): δ 8.20 (dd, J=1.3 Hz, J=7.5 Hz, 1H), 7.77 (dd, J=1.3 Hz, J=7.5 Hz, 1H), 7.74 (t, J=7.6 Hz, 1H), 7.53 (t, J=8.2 Hz, 1H), 7.40 (d, J=8.4 Hz, 1H), 7.09 (d, J=8.1 Hz, 1H), 5.61-5.57 (m, 1H), 4.56 (s, 2H), 4.40 (s, 2H), 4.15 (s, 3H), 4.00 (s, 3H), 3.48-3.44 (m, 2H), 2.40-2.23 (m, 2H), 2.11-2.01 (m, 1H), 1.98-1.87 (m, 1H). ¹³C NMR (100 MHz, CD₃OD) δ 171.8, 165.9, 163.4, 160.8, 152.4, 148.4, 146.2, 134.4, 132.8, 131.8, 130.4, 130.2, 128.9, 127.3, 126.9, 106.2, 103.7, 55.3, 45.4, 41.8, 38.7, 30.7, 28.7, 23.6. HRMS m/z calculated for C₂₄H₂₇ClN₆O₃ (M+H) 483.1906; found 483.1907.

(N1-(3-oxoisoindoline)benzoyl-N5-(2-fluoro-1-iminoethyl)-1-(4-ethoxy-1-ethyl-benzo[d]imidazol-2-yl)-L-ornithine) (7m)

(N1-(3-oxoisoindoline)benzoyl-N5-(2-fluoro-1-iminoethyl)-1-(5-methoxy-1-methyl-benzo[d]imidazol-2-yl)-L-ornithine) (7o)

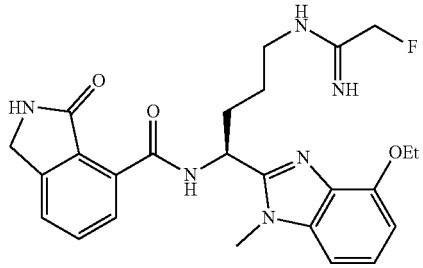 [SMILES: CCOc1cccc2c1nc([C@H](CCCNC(=N)CF)NC(=O)c1cccc3c1C(=O)NC3)n2C]

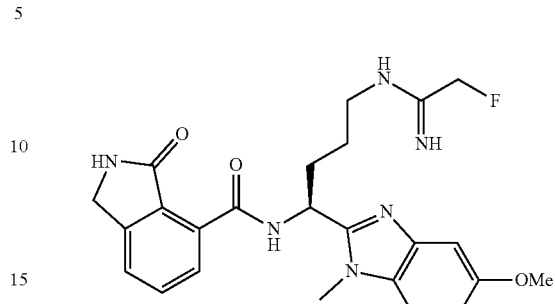

$^1$H NMR (CD$_3$OD; 500 MHz): δ 8.10 (dd, J=1.1 Hz, J=7.7 Hz, 1H), 7.71 (dd, J=1.1 Hz, J=7.7 Hz, 1H), 7.64 (t, J=7.7 Hz, 1H), 7.41 (t, J=8.2 Hz, 1H), 7.30 (d, J=8.1 Hz, 1H), 6.97 (d, J=8.4 Hz, 1H), 5.50-5.47 (m, 1H), 5.21 (d, J=45.4 Hz, 2H), 4.46 (s, 2H), 4.18-4.13 (m, 2H), 4.08 (s, 3H), 3.44-3.36 (m, 2H), 2.32-2.23 (m, 1H), 2.22-2.14 (m, 1H), 2.02-1.94 (m, 1H), 1.89-1.79 (m, 1H), 1.36 (t, J=7.1 Hz, 3H). $^{13}$C NMR (125 MHz, CD$_3$OD) δ 171.9, 166.0, 163.0, 161.3, 152.6, 147.2, 146.3, 134.3, 131.8, 130.5, 130.2, 128.9, 127.3, 127.1, 107.1, 103.7, 78.4, 76.9, 64.5, 45.4, 41.3, 31.0, 28.8, 23.8, 13.5. HRMS m/z calculated for C$_{25}$H$_{29}$FN$_6$O$_3$ (M+H$^+$) 481.2358; found 481.2356.

$^1$H NMR (CD$_3$OD; 500 MHz): δ 8.08 (dd, J=1.2 Hz, J=7.6 Hz, 1H), 7.68 (m, 3H), 7.15 (dd, J=2.4 Hz, J=9.2 Hz, 1H), 7.08 (d, J=2.4 Hz, 1H), 5.50-5.47 (m, 1H), 5.21 (d, J=45.2 Hz, 2H), 4.48 (s, 2H), 4.08 (s, 3H), 3.78 (s, 3H), 3.45-3.35 (m, 2H), 2.27-2.13 (m, 2H), 2.02-1.93 (m, 1H), 1.91-1.82 (m, 1H). $^{13}$C NMR (125 MHz, CD$_3$OD) δ 172.0, 166.3, 161.1, 159.5, 152.2, 146.3, 131.8, 131.5, 130.2, 128.9, 127.3, 127.0, 116.2, 113.0, 95.9, 78.3, 76.9, 55.2, 46.6, 45.5, 41.2, 30.7, 28.8, 23.8. HRMS m/z calculated for C$_{24}$H$_{27}$FN$_6$O$_3$ (M+H$^+$) 467.2201; found 467.2201.

(N1-(3-oxoisoindoline)benzoyl-N5-(2-chloro-1-iminoethyl)-1-(4-ethoxy-1-ethyl-benzo[d]imidazol-2-yl)-L-ornithine) (7n)

(N1-(3-oxoisoindoline)benzoyl-N5-(2-chloro-1-iminoethyl)-1-(5-methoxy-1-methyl-benzo[d]imidazol-2-yl)-L-ornithine) (7p)

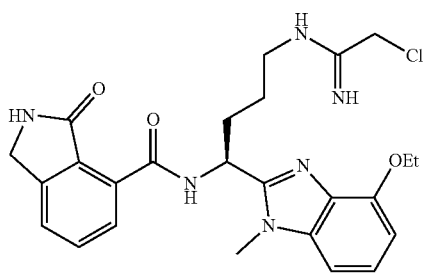 [SMILES: CCOc1cccc2c1nc([C@H](CCCNC(=N)CCl)NC(=O)c1cccc3c1C(=O)NC3)n2C]

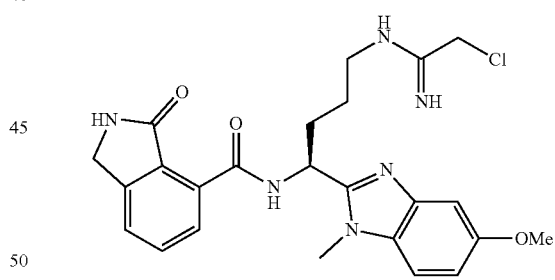

$^1$H NMR (CD$_3$OD; 500 MHz): δ 8.08 (dd, J=1.2 Hz, J=7.7 Hz, 1H), 7.70 (dd, J=1.1 Hz, J=7.6 Hz, 1H), 7.63 (t, J=7.7 Hz, 1H), 7.42 (t, J=8.3 Hz, 1H), 7.29 (d, J=8.1 Hz, 1H), 6.97 (d, J=8.1 Hz, 1H), 5.51-5.47 (m, 1H), 4.45 (s, 2H), 4.32 (s, 2H), 4.17-4.12 (m, 2H), 4.08 (s, 3H), 3.40-3.36 (m, 2H), 2.33-2.24 (m, 1H), 2.23-2.16 (m, 1H), 2.03-1.94 (m, 1H), 1.89-1.80 (m, 1H), 1.34 (t, J=7.1 Hz, 3H). $^{13}$C NMR (125 MHz, CD$_3$OD) δ 171.9, 166.1, 163.5, 161.2, 160.8, 152.6, 147.1, 146.3, 134.3, 131.8, 130.4, 130.2, 129.0, 127.3, 121.5, 107.2, 103.7, 64.6, 45.4, 41.9, 38.8, 30.9, 28.8, 23.7, 13.4. HRMS m/z calculated for C$_{25}$H$_{29}$ClN$_6$O$_3$ (M+H$^+$) 497.2062; found 497.2061.

$^1$H NMR (CD$_3$OD; 500 MHz): δ 8.08 (dd, J=1.1 Hz, J=7.5 Hz, 1H), 7.68 (m, 3H), 7.16 (dd, J=2.5 Hz, J=9.2 Hz, 1H), 7.08 (d, J=2.3 Hz, 1H), 5.51-5.48 (m, 1H), 4.48 (s, 2H), 4.08 (s, 3H), 3.78 (s, 3H), 3.43-3.33 (m, 2H), 2.28-2.14 (m, 2H), 2.01-1.93 (m, 1H), 1.91-1.82 (m, 1H). $^{13}$C NMR (125 MHz, CD$_3$OD) δ 171.9, 166.3, 163.5, 160.8, 159.4, 152.2, 146.3, 131.9, 131.5, 130.2, 128.9, 127.3, 127.0, 116.2, 113.0, 95.9, 55.2, 46.6, 45.5, 41.9, 38.7, 30.8, 28.7, 23.6. HRMS m/z calculated for C$_{24}$H$_{27}$ClN$_6$O$_3$ (M+H$^+$) 483.1906; found 483.1906.

81

(N1-(3-oxoisoindoline)benzoyl-N5-(2-fluoro-1-iminoethyl)-1-(4-methoxy-1-ethyl-benzo[d]imidazol-2-yl)-L-ornithine) (7q)

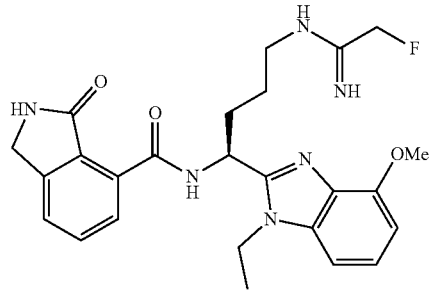 [SMILES: CCn1c([C@H](CCCNC(=N)CF)NC(=O)c2cccc3c2C(=O)NC3)nc2c(OC)cccc21]

¹H NMR (CD₃OD; 500 MHz): δ 8.12 (dd, J=1.1 Hz, J=7.7 Hz, 1H), 7.72 (dd, J=1.1 Hz, J=7.6 Hz, 1H), 7.65 (t, J=7.2 Hz, 1H), 7.44 (t, J=8.4 Hz, 1H), 7.34 (d, J=8.4 Hz, 1H), 7.00 (d, J=8.1 Hz, 1H), 5.52-5.48 (m, 1H), 5.21 (d, J=45.3 Hz, 2H), 4.64-4.57 (m, 1H), 4.56-4.50 (m, 1H), 4.48 (s, 2H), 3.92 (s, 3H), 3.45-3.35 (m, 2H), 2.29-2.21 (m, 1H), 2.20-2.13 (m, 1H), 2.03-1.94 (m, 1H), 1.90-1.83 (m, 1H), 1.49 (t, J=7.2 Hz, 3H). ¹³C NMR (125 MHz, CD₃OD) δ 172.0, 165.9, 161.1, 152.1, 148.2, 146.3, 133.3, 131.9, 130.5, 130.2, 128.9, 127.3, 127.0, 106.4, 104.0, 78.4, 77.0, 55.3, 46.8, 45.5, 41.4, 40.6, 29.4, 23.8, 13.4. HRMS m/z calculated for $C_{25}H_{29}FN_6O_3$ (M+H⁺) 481.2358; found 481.2353.

(N1-(3-oxoisoindoline)benzoyl-N5-(2-chloro-1-iminoethyl)-1-(4-methoxy-1-ethyl-benzo[d]imidazol-2-yl)-L-ornithine) (7r)

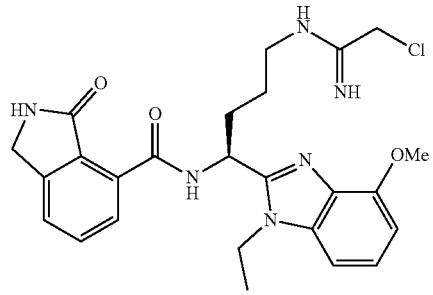

¹H NMR (CD₃OD; 500 MHz): δ 8.11 (dd, J=1.3 Hz, J=7.9 Hz, 1H), 7.72 (dd, J=1.3 Hz, J=7.6 Hz, 1H), 7.64 (t, J=7.6 Hz, 1H), 7.45 (t, J=8.3 Hz, 1H), 7.35 (d, J=8.4 Hz, 1H), 7.02 (d, J=8.2 Hz, 1H), 5.52-5.49 (m, 1H), 4.64-4.58 (m, 1H), 4.57-4.52 (m, 1H), 4.48 (s, 2H), 4.31 (s, 2H), 3.91 (s, 3H), 3.42-3.34 (m, 2H), 2.30-2.22 (m, 1H), 2.20-2.12 (m, 1H), 2.04-1.95 (m, 1H), 1.91-1.82 (m, 1H), 1.49 (t, J=7.5 Hz, 3H). ¹³C NMR (125 MHz, CD₃OD) δ 172.0, 166.0, 163.4, 160.7, 152.1, 148.1, 146.3, 133.1, 131.9, 130.5, 130.2, 128.9, 127.3, 121.9, 106.5, 104.0, 55.3, 46.8, 45.4, 41.8, 40.6, 38.8, 29.2, 23.7, 13.3. HRMS m/z calculated for $C_{25}H_{29}ClN_6O_3$ (M+H⁺) 497.2062; found 497.2060.

82

(N1-(3-oxoisoindoline)benzoyl-N5-(2-fluoro-1-iminoethyl)-1-(5-methoxy-1H-benzo[d]imidazol-2-yl)-L-ornithine) (7s)

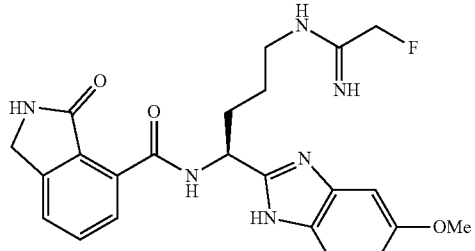

¹H NMR (CD₃OD; 500 MHz): δ 8.22 (d, J=8.3 Hz, 1H), 7.86 (d, J=8.3 Hz, 1H), 7.80 (t, J=6.6 Hz, 1H), 7.65 (d, J=8.8 Hz, 1H), 7.23 (s, 1H), 7.20 (dd, J=2.3 Hz, J=8.8 Hz, 1H), 5.58-5.55 (m, 1H), 5.32 (d, J=45.7 Hz, 2H), 4.62 (s, 2H), 3.92 (s, 3H), 3.57-3.47 (m, 2H), 2.38-2.28 (m, 2H), 2.07-1.93 (m, 2H). ¹³C NMR (125 MHz, CD₃OD) δ 171.9, 169.3, 166.7, 159.0, 153.2, 146.2, 131.9, 130.8, 130.0, 128.9, 127.0, 115.9, 114.4, 99.8, 95.7, 78.3, 76.7, 55.2, 45.4, 41.2, 29.6, 23.7. HRMS m/z calculated for $C_{23}H_{25}FN_6O_3$ (M+H⁺) 453.2045; found 453.2037.

(N1-(3-oxoisoindoline)benzoyl-N5-(2-chloro-1-iminoethyl)-1-(5-methoxy-1H-benzo[d]imidazol-2-yl)-L-ornithine) (7t)

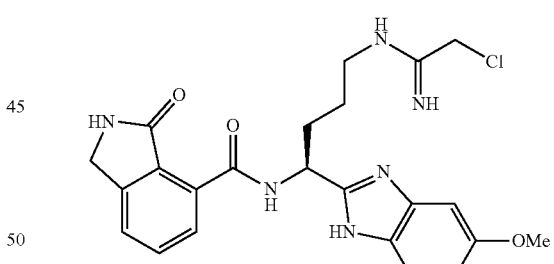

¹H NMR (CD₃OD; 500 MHz): δ 8.05 (d, J=8.1 Hz, 1H), 7.71 (d, J=8.2 Hz, 1H), 7.65 (t, J=7.6 Hz, 1H), 7.52 (d, J=8.9 Hz, 1H), 7.11 (s, 1H), 7.07 (dd, J=2.2 Hz, J=8.4 Hz, 1H), 5.48-5.45 (m, 1H), 4.48 (s, 2H), 4.31 (s, 2H), 3.78 (s, 3H), 3.40-3.33 (m, 2H), 2.26-2.16 (m, 2H), 1.94-1.82 (m, 2H). ¹³C NMR (125 MHz, CD₃OD) 171.8, 166.8, 163.5, 159.2, 153.2, 146.1, 132.2, 131.9, 130.8, 130.0, 128.8, 127.0, 125.2, 116.2, 114.4, 95.8, 55.0, 45.4, 41.8, 38.8, 29.6, 23.5. HRMS m/z calculated for $C_{23}H_{25}ClN_6O_3$ (M+H⁺) 469.1749; found 469.1741.

(N1-(3-oxoisoindoline)benzoyl-N5-(2-fluoro-1-iminoethyl)-1-(5-methoxy-1-ethyl-benzo[d]imidazol-2-yl)-L-ornithine) (7u)

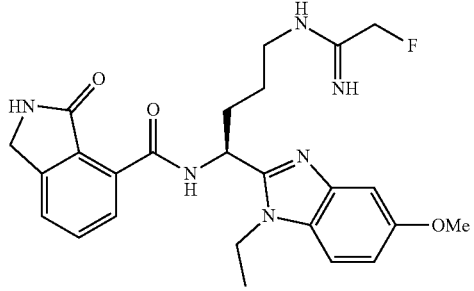 [SMILES: CCn1c([C@H](CCCNC(=N)CF)NC(=O)c2cccc3c2C(=O)NC3)nc2cc(OC)ccc21]

¹H NMR (CD₃OD; 500 MHz): δ 8.20 (d, J=7.7 Hz, 1H), 7.84 (d, J=8.4 Hz, 2H), 7.77 (t, J=7.7 Hz, 1H), 7.26 (dd, J=2.2 Hz, J=8.4 Hz, 1H), 7.22 (d, J=2.3 Hz, 1H), 5.64-5.61 (m, 1H), 5.34 (d, J=45.5 Hz, 2H), 4.78-4.64 (m, 2H), 4.61 (s, 2H), 3.90 (s, 3H), 3.59-3.48 (m, 2H), 2.41-2.24 (m, 2H), 2.19-1.98 (m, 2H), 1.84-1.80 (m, 1H), 1.75-1.69 (m, 1H), 1.64 (t, J=7.2 Hz, 3H). ¹³C NMR (125 MHz, CD₃OD) 171.9, 166.2, 163.2, 161.1, 159.4, 151.8, 146.3, 131.8, 130.4, 128.9, 127.2, 125.7, 116.2, 113.3, 96.1, 78.3, 77.0, 55.0, 46.7, 45.5, 41.4, 40.7, 29.4, 23.7, 13.4. HRMS m/z calculated for $C_{25}H_{29}FN_6O_3$ (M+H⁺) 481.2358; found 481.2358.

(N1-(3-oxoisoindoline)benzol-N5-(2-chloro-1-iminoethyl)-1-(5-methoxy-1-ethyl-benzo[d]imidazol-2-yl)-L-ornithine) (7v)

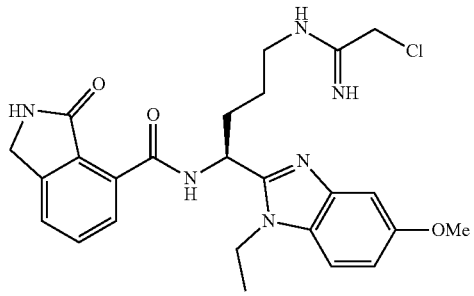 [SMILES: CCn1c([C@H](CCCNC(=N)CCl)NC(=O)c2cccc3c2C(=O)NC3)nc2cc(OC)ccc21]

¹H NMR (CD₃OD; 500 MHz): δ 8.07 (d, J=8.0 Hz, 1H), 7.71 (d, J=8.6 Hz, 2H), 7.64 (t, J=7.9 Hz, 1H), 7.13 (dd, J=2.6 Hz, J=8.8 Hz, 1H), 7.08 (d, J=2.3 Hz, 1H), 5.51-5.48 (m, 1H), 4.64-4.50 (m, 2H), 4.47 (s, 2H), 4.33 (s, 2H), 3.77 (s, 3H), 3.42-3.35 (m, 2H), 2.28-2.11 (m, 2H), 2.03-1.83 (m, 2H), 1.72-1.67 (m, 1H), 1.62-1.58 (m, 1H), 1.51 (t, J=8.1 Hz, 3H). ¹³C NMR (125 MHz, CD₃OD) δ 171.9, 166.2, 163.4, 161.2, 161.0, 159.5, 151.9, 146.3, 131.8, 130.3, 128.8, 127.2, 125.8, 125.6, 116.2, 113.2, 96.0, 55.2, 46.6, 45.5, 41.8, 40.6, 38.8, 29.4, 23.7, 13.4. HRMS m/z calculated for $C_{25}H_{29}ClN_6O_3$ (M+H⁺) 497.2062; found 497.2065.

5. General Procedure for Synthesis of Benzimidazole Haloacetamidines 8a-b'.[a]

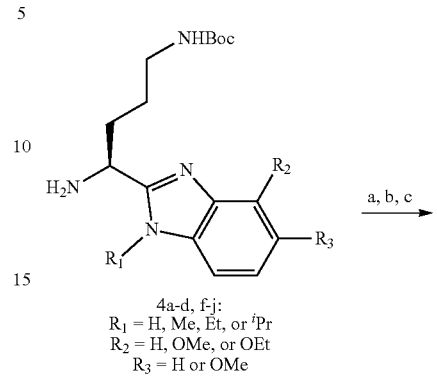

4a-d, f-j:
$R_1$ = H, Me, Et, or $^iPr$
$R_2$ = H, OMe, or OEt
$R_3$ = H or OMe

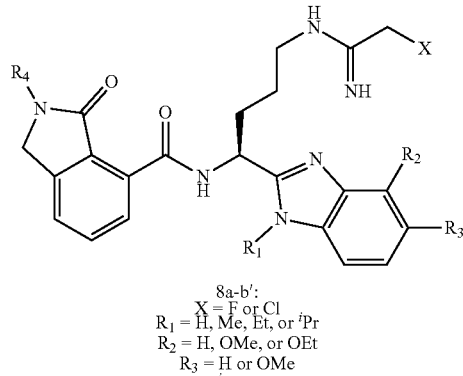

8a-b':
X = F or Cl
$R_1$ = H, Me, Et, or $^iPr$
$R_2$ = H, OMe, or OEt
$R_3$ = H or OMe
$R_4$ = Me, Et, $^iPr$, or cyclopropyl

[a]Reagents: (a) 2-alkyl-3-oxo-4-isoindoline carboxylic acid, HOBt, HBTU, DIPEA, DMF; (b) 2M HCl/Et₂O; (c) ethyl 2-haloacetimidate, TEA, MeOH To a stirred solution of 4a-d, f-j (1.0 eq) in DMF was added HOBt (2.0 eq), HBTU (2.0 eq), and DIPEA (3.0 eq) followed by 2-alkyl-3-oxo-4-isoindoline carboxylic acid (1.0 eq) and allowed to stir at rt for 12 h. The reaction mixture was then diluted with water. The product was filtered, washed with water, dried under vacuum, and obtained in 62-71% yield. This product was then treated with 2 M HCl in Et₂O to remove the Boc group giving the N-alkyl-Oxoisoindoline-Orn-benzimidazole intermediate. The solvent was then evaporated to dryness and the crude material was dried in vacuo. To a stirred solution of the corresponding N-alkyl-Oxoisoindoline-Orn-benzimidazole intermediate in dry MeOH was added TEA (4.0 eq) followed by ethyl haloacetimidate HCl (2.0 eq). The reaction was stirred under N₂ at rt for 3 h. Solvents were then evaporated under reduced pressure and the crude product was purified by reverse phase HPLC using MeCN:H₂O (0.5% TFA) as an eluent to give compounds 8a-b' in 56-74% yield.

(N1-(2-ethyl-3-oxoisoindoline)benzol-N5-(2-fluoro-1-iminoethyl)-1-(1H-benzo[d]imidazol-2-yl)-L-ornithine) (8a)

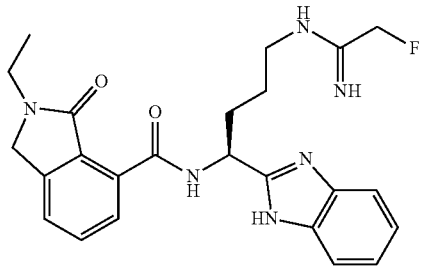 [SMILES: CCN1Cc2cccc(C(=O)N[C@@H](CCCNC(=N)CF)c3nc4ccccc4[nH]3)c2C1=O]

¹H NMR (CD₃OD; 400 MHz): δ 8.11 (dd, J=1.1 Hz, J=7.7 Hz, 1H), 7.80-7.70 (m, 4H), 7.60-7.55 (m, 2H), 5.64-5.59 (m, 1H), 5.28 (d, J=45.4 Hz, 2H), 4.63 (s, 2H), 3.80-3.74 (m, 2H), 3.52-3.48 (m, 2H), 2.39-2.28 (m, 2H), 2.06-1.92 (m, 2H), 1.35 (t, J=7.3 Hz, 3H). ¹³C NMR (100 MHz, CD₃OD) δ 168.3, 166.4, 163.1, 162.9, 160.7, 154.0, 143.3, 131.3, 131.1, 130.2, 129.8, 129.1, 126.4, 126.1 (2C), 113.5, 78.3, 76.6, 49.2, 41.2, 37.5, 29.5, 23.7, 11.9. HRMS m/z calculated for $C_{24}H_{27}FN_6O_2$ (M+H⁺) 451.2252; found 451.2249.

(N1-(2-ethyl-3-oxoisoindoline)benzol-N5-(2-chloro-1-iminoethyl)-1-(1H-benzo[d]imidazol-2-yl)-L-ornithine) (8b)

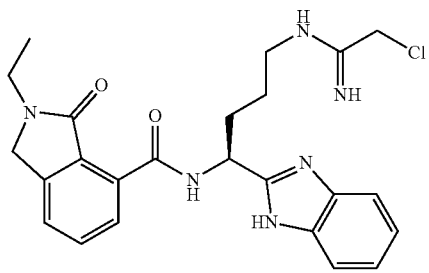 [SMILES: CCN1Cc2cccc(C(=O)N[C@@H](CCCNC(=N)CCl)c3nc4ccccc4[nH]3)c2C1=O]

¹H NMR (CD₃OD; 400 MHz): δ 8.12 (dd, J=1.2 Hz, J=7.8 Hz, 1H), 7.81-7.70 (m, 4H), 7.60-7.56 (m, 2H), 5.63-5.59 (m, 1H), 4.63 (s, 2H), 4.38 (s, 2H), 3.80-3.75 (m, 2H), 3.50-3.45 (m, 2H), 2.41-2.31 (m, 2H), 2.08-1.92 (m, 2H), 1.35 (t, J=7.2 Hz, 3H). ¹³C NMR (100 MHz, CD₃OD) δ 168.3, 166.5, 163.2, 161.1, 160.8, 154.1, 143.4, 131.3, 131.1, 130.2, 129.8, 129.0, 126.5, 125.9 (2C), 113.5 (2C), 49.2, 41.7, 38.7, 37.4, 29.4, 23.4, 12.0. HRMS m/z calculated for $C_{24}H_{27}ClN_6O_2$ (M+H⁺) 467.1957; found 467.1954.

(N1-(2-ethyl-3-oxoisoindoline)benzoyl-N5-(2-fluoro-1-iminoethyl)-1-(1-methyl-benzo[d]imidazol-2-yl)-L-ornithine) (8c)

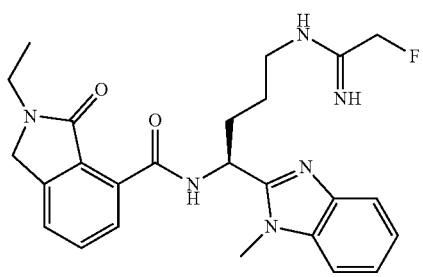 [SMILES: CCN1Cc2cccc(C(=O)N[C@@H](CCCNC(=N)CF)c3nc4ccccc4n3C)c2C1=O]

¹H NMR (CD₃OD; 400 MHz): δ 8.17 (dd, J=1.2 Hz, J=7.9 Hz, 1H), 7.88 (dd, J=1.5 Hz, J=7.7 Hz, 1H), 7.80 (dd, J=1.2 Hz, J=7.8 Hz, 1H), 7.74-7.70 (m, 2H), 7.64-7.56 (m, 2H), 5.67-5.63 (m, 1H), 5.28 (d, J=45.5 Hz, 2H), 4.64 (s, 2H), 4.19 (s, 3H), 3.79-3.72 (m, 2H), 3.56-3.45 (m, 2H), 2.41-2.25 (m, 2H), 2.14-2.03 (m, 1H), 2.01-1.89 (m, 1H), 1.34 (t, J=7.5 Hz, 3H). ¹³C NMR (100 MHz, CD₃OD) δ 168.1, 166.0, 162.9, 158.3, 152.8, 143.4, 133.1, 131.3, 130.3, 129.8, 129.3, 126.8, 126.1, 125.6, 114.1, 111.9, 109.8, 78.4, 76.5, 49.2, 41.3, 37.5, 30.5, 28.8, 23.6. 12.0. HRMS m/z calculated for $C_{25}H_{29}FN_6O_2$ (M+H⁺) 465.2409; found 465.2404.

(N1-(2-ethyl-3-oxoisoindoline)benzoyl-N5-(2-chloro-1-iminoethyl)-1-(1-methyl-benzo[d]imidazol-2-yl)-L-ornithine) (8d)

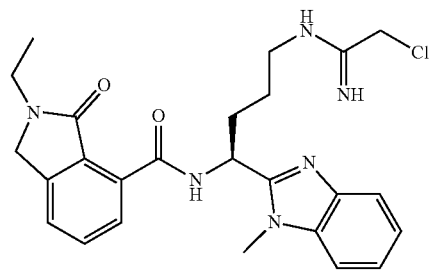 [SMILES: CCN1Cc2cccc(C(=O)N[C@@H](CCCNC(=N)CCl)c3nc4ccccc4n3C)c2C1=O]

¹H NMR (CD₃D; 400 MHz): δ 8.16 (dd, J=1.5 Hz, J=7.7 Hz, 1H), 7.91 (dd, J=1.1 Hz, J=7.6 Hz, 1H), 7.80 (dd, J=1.5 Hz, J=7.6 Hz, 1H), 7.75-7.70 (m, 2H), 7.66-7.58 (m, 2H), 5.68-5.63 (m, 1H), 4.64 (s, 2H), 4.38 (s, 2H), 4.21 (s, 3H), 3.79-3.73 (m, 2H), 3.50-3.46 (m, 2H), 2.42-2.26 (m, 2H), 2.16-2.05 (m, 1H), 2.02-1.91 (m, 1H), 1.34 (t, J=7.2 Hz, 3H). ¹³C NMR (100 MHz, CD₃OD) δ 168.4, 165.9, 163.2, 160.8, 153.3, 143.5, 132.5, 131.2, 130.1, 129.5, 129.2, 126.7, 126.3, 125.7, 113.9, 112.1, 109.9, 49.2, 41.7, 38.7, 37.5, 30.6, 28.7, 23.4, 11.9. HRMS m/z calculated for $C_{25}H_{29}ClN_6O_2$ (M+H⁺) 481.2113; found 481.2118.

(N1-(2-ethyl-3-oxoisoindoline)benzoyl-N5-(2-fluoro-1-iminoethyl)-1-(1-ethyl-benzo[d]imidazol-2-yl)-L-ornithine) (8e)

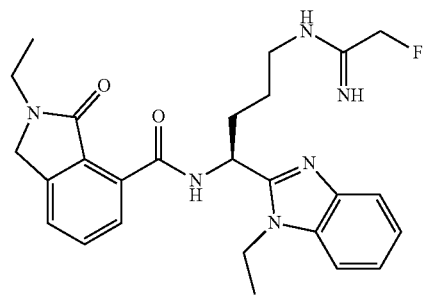 [SMILES: CCN1Cc2cccc(C(=O)N[C@@H](CCCNC(=N)CF)c3nc4ccccc4n3CC)c2C1=O]

¹H NMR (CD₃OD; 400 MHz): δ 8.15 (dd, J=1.1 Hz, J=7.8 Hz, 1H), 7.95 (dd, J=1.2 Hz, J=7.2 Hz, 1H), 7.80 (dd, J=1.2 Hz, J=7.7 Hz, 1H), 7.76-7.69 (m, 2H), 7.67-7.59 (m, 2H), 5.67-5.63 (m, 1H), 5.29 (d, J=45.4 Hz, 2H), 4.82-4.66 (m, 2H), 4.64 (s, 2H), 3.81-3.72 (m, 3H), 3.56-3.46 (m, 2H), 2.42-2.23 (m, 2H), 2.18-2.08 (m, 1H), 2.05-1.93 (m, 1H), 1.64 (t, J=7.2 Hz, 3H), 1.35 (t, J=7.3 Hz, 3H). $^{13}$C NMR (100 MHz, CD$_3$OD) δ 168.1, 165.9, 163.0, 153.1, 143.5, 131.6, 131.3, 130.6, 130.1, 129.6, 129.2, 126.7, 126.4, 126.1, 113.9, 112.5, 78.4, 76.7, 49.2, 41.2, 40.6, 37.6, 29.2, 23.8, 13.2, 12.1. HRMS m/z calculated for C$_{26}$H$_{31}$FN$_6$O$_2$ (M+H$^+$) 479.2565; found 479.2565.

(N1-(2-ethyl-3-oxoisoindoline)benzoyl-N5-(2-chloro-1-iminoethyl)-1-(1-ethyl-benzo[d]imidazol-2-yl)-L-ornithine) (8f)

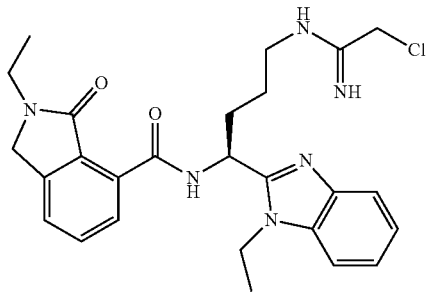 [SMILES: CCN1Cc2cccc(C(=O)N[C@@H](CCCNC(=N)CCl)c3nc4ccccc4n3CC)c2C1=O]

$^1$H NMR (CD$_3$OD; 400 MHz): δ 8.15 (dd, J=1.2 Hz, J=7.8 Hz, 1H), 7.94 (dd, J=1.1 Hz, J=7.1 Hz, 1H), 7.80 (dd, J=1.1 Hz, 7.4 Hz, 1H), 7.76-7.69 (m, 2H), 7.66-7.58 (m, 2H), 5.68-5.64 (m, 1H), 4.81-4.66 (m, 2H), 4.63 (s, 2H), 4.40 (s, 2H), 3.79-3.74 (m, 3H), 3.52-3.47 (m, 2H), 2.43-2.33 (m, 1H), 2.31-2.25 (m, 1H), 2.18-2.07 (m, 1H), 2.05-1.94 (m, 1H), 1.63 (t, J=7.3 Hz, 3H), 1.34 (t, J=7.3 Hz, 3H). $^{13}$C NMR (100 MHz, CD$_3$OD) δ 168.3, 166.3, 163.1, 161.2, 152.8, 143.8, 131.6, 131.2, 130.5, 130.0, 129.6, 129.0, 126.7, 126.3, 125.7, 114.0, 112.2, 49.2, 42.0, 40.4, 38.5, 37.4, 29.0, 23.3, 13.3, 11.9. HRMS m/z calculated for C$_{26}$H$_{31}$ClN$_6$O$_2$ (M+H$^+$) 495.2270; found 495.2273.

(N1-(2-ethyl-3-oxoisoindoline)benzol-N5-(2-fluoro-1-iminoethyl)-1-(1-isopropyl-benzo[d]imidazol-2-yl)-L-ornithine) (82)

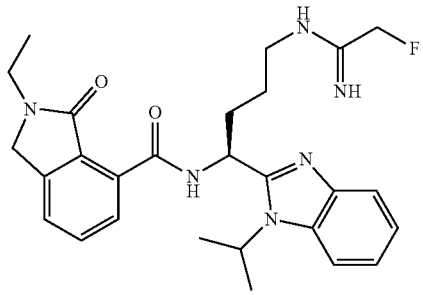 [SMILES: CCN1Cc2cccc(C(=O)N[C@@H](CCCNC(=N)CF)c3nc4ccccc4n3C(C)C)c2C1=O]

$^1$H NMR (CD$_3$OD; 400 MHz): δ 8.16-8.10 (m, 2H), 7.81-7.69 (m, 3H), 7.62-7.57 (m, 2H), 5.72-5.68 (m, 1H), 5.34-5.29 (m, 1H), 5.28 (d, J=45.4 Hz, 2H), 4.64 (s, 2H), 3.80-3.73 (m, 2H), 3.56-3.47 (m, 2H), 2.42-2.21 (m, 2H), 2.16-2.05 (m, 1H), 2.03-1.92 (m, 1H), 1.85 (d, J=2.7 Hz, 3H), 1.83 (d, J=2.7 Hz, 3H), 1.35 (t, J=7.3 Hz, 3H). $^{13}$C NMR (100 MHz, CD$_3$OD) 168.4, 166.1, 163.2, 162.7, 161.2, 160.8, 152.7, 143.6, 131.4, 130.1, 129.7, 129.1, 126.6, 126.0, 125.6, 114.7, 114.3, 78.4, 76.6, 51.2, 49.2, 41.3, 37.4, 29.3, 23.8, 19.4, 12.0. HRMS m/z calculated for C$_{27}$H$_{33}$FN$_6$O$_2$ (M+H$^+$) 493.2722; found 493.2723.

(N1-(2-ethyl-3-oxoisoindoline)benzoyl-N5-(2-chloro-1-iminoethyl)-1-(1-isopropyl-benzo[d]imidazol-2-yl)-L-ornithine) (8h)

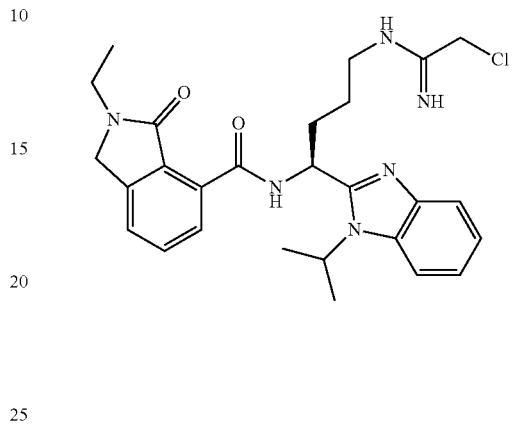

$^1$H NMR (CD$_3$OD; 400 MHz): δ 8.16-8.09 (m, 2H), 7.81-7.69 (m, 3H), 7.61-7.57 (m, 2H), 5.72-5.68 (m, 1H), 5.36-5.29 (m, 1H), 4.64 (s, 2H), 4.40 (s, 2H), 3.79-3.74 (m, 2H), 3.52-3.48 (m, 2H), 2.42-2.22 (m, 2H), 2.17-2.06 (m, 1H), 2.05-1.92 (m, 1H), 1.85 (d, J=3.4 Hz, 3H), 1.83 (d, J=3.4 Hz, 3H), 1.34 (t, J=7.2 Hz, 3H). $^{13}$C NMR (100 MHz, CD$_3$OD) 168.5, 166.3, 163.4, 161.2, 160.9, 160.5, 152.8, 143.6, 131.3, 130.2, 129.8, 129.2, 126.8, 126.2, 125.7, 115.0, 114.7, 114.3, 51.3, 49.3, 41.9, 38.7, 37.5, 29.4, 23.6, 19.6, 12.1. HRMS m/z calculated for C$_{27}$H$_{33}$ClN$_6$O$_2$ (M+H$^+$) 509.2426; found 509.2426.

(N1-(2-ethyl-3-oxoisoindoline)benzoyl-N5-(2-fluoro-1-iminoethyl)-1-(4-methoxy-1H-benzo[d]imidazol-2-yl)-L-ornithine) (8i)

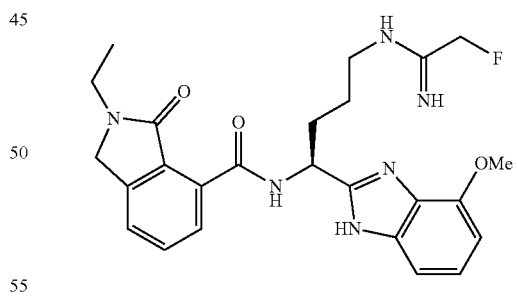

$^1$H NMR (CD$_3$OD; 500 MHz): δ 8.04 (d, J=7.8 Hz, 1H), 7.70 (d, J=7.9 Hz, 1H), 7.63 (t, J=8.7 Hz, 1H), 7.39 (t, J=7.8 Hz, 1H), 7.19 (d, J=8.7 Hz, 1H), 6.99 (d, J=8.7 Hz, 1H), 5.45-5.42 (m, 1H), 5.18 (d, J=45.3 Hz, 2H), 4.55 (s, 2H), 3.95 (s, 3H), 3.71-3.64 (m, 2H), 3.43-3.37 (m, 2H), 2.26-2.21 (m, 2H), 1.96-1.79 (m, 2H), 1.26 (t, J=7.9 Hz, 3H). $^{13}$C NMR (125 MHz, CD$_3$OD) δ 168.6, 166.7, 163.2, 153.5, 147.7, 143.6, 132.6, 131.4, 130.4, 130.0, 129.2, 127.2, 126.6, 122.0, 106.2, 105.4, 78.3, 76.8, 55.3, 49.4, 41.4, 37.5, 29.7, 23.8, 12.1. HRMS m/z calculated for C$_{25}$H$_{29}$FN$_6$O$_3$ (M+H$^+$) 481.2358; found 481.2358.

89

(N1-(2-ethyl-3-oxoisoindoline)benzoyl-N5-(2-chloro-1-iminoethyl)-1-(4-methoxy-1H-benzo[d]imidazol-2-yl)-L-ornithine) (8)

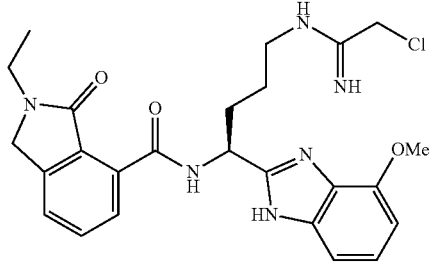 [SMILES: CCN1Cc2cccc(C(=O)N[C@@H](CCCNC(=N)CCl)c3nc4c(OC)cccc4[nH]3)c2C1=O]

$^1$H NMR (CD$_3$OD; 500 MHz): δ 8.16 (d, J=7.4 Hz, 1H), 7.83 (d, J=7.2 Hz, 1H), 7.76 (d, J=7.8 Hz, 1H), 7.52 (t, J=7.5 Hz, 1H), 7.32 (d, J=8.1 Hz, 1H), 7.12 (d, J=7.8 Hz, 1H), 5.58-5.55 (m, 1H), 4.67 (s, 2H), 4.41 (s, 2H), 4.07 (s, 3H), 3.83-3.79 (m, 2H), 3.52-3.48 (m, 2H), 2.39-2.34 (m, 2H), 2.09-1.93 (m, 2H), 1.38 (t, J=7.5 Hz, 3H). $^{13}$C NMR (125 MHz, CD$_3$OD) δ 168.6, 166.5, 163.5, 153.7, 147.6, 143.5, 132.6, 131.3, 130.4, 129.9, 129.1, 127.3, 126.7, 125.6, 121.9, 106.2, 105.2, 55.3, 49.4, 41.9, 38.8, 37.6, 29.7, 23.6, 11.9. HRMS m/z calculated for C$_{25}$H$_{29}$ClN$_6$O$_3$ (M+H$^+$) 497.2062; found 497.2060.

(N1-(2-ethyl-3-oxoisoindoline)benzoyl-N5-(2-fluoro-1-iminoethyl)-1-(4-methoxy-1-methyl-benzo[d]imidazol-2-yl)-L-ornithine) (8k)

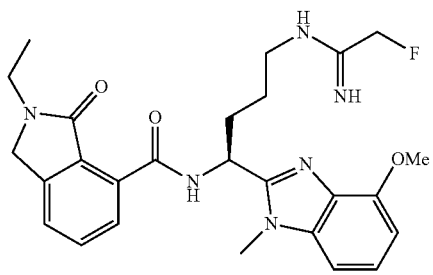 [SMILES: CCN1Cc2cccc(C(=O)N[C@@H](CCCNC(=N)CF)c3nc4c(OC)cccc4n3C)c2C1=O]

$^1$H NMR (CD$_3$OD; 400 MHz): δ 8.16 (dd, J=1.4 Hz, J=7.8 Hz, 1H), 7.80 (dd, J=1.3 Hz, J=7.8 Hz, 1H), 7.71 (t, J=7.5 Hz, 1H), 7.55 (t, J=8.3 Hz, 1H), 7.42 (dd, J=1.1 Hz, J=8.6 Hz, 1H), 7.11 (d, J=8.2 Hz, 1H), 5.62-5.58 (m, 1H), 5.19 (d, J=45.5 Hz, 2H), 4.63 (s, 2H), 4.18 (s, 3H), 4.01 (s, 3H), 3.81-3.70 (m, 2H), 3.52-3.48 (m, 2H), 2.43-2.24 (m, 2H), 2.14-2.03 (m, 1H), 1.98-1.86 (m, 1H), 1.34 (t, J=7.1 Hz, 3H). $^{13}$C NMR (100 MHz, CD$_3$OD) δ 168.5, 166.1, 160.7, 152.5, 147.9, 143.7, 134.4, 131.3, 130.3, 129.7, 129.3, 127.1, 126.7, 115.0, 106.5, 103.9, 78.4, 76.6, 55.3, 49.2, 41.3, 37.6, 30.9, 28.8, 23.8, 12.0. HRMS m/z calculated for C$_{26}$H$_{31}$FN$_6$O$_3$ (M+H$^+$) 495.2514; found 495.2512.

90

(N1-(2-ethyl-3-oxoisoindoline)benzoyl-N5-(2-chloro-1-iminoethyl)-1-(4-methoxy-1-methyl-benzo[d]imidazol-2-yl)-L-ornithine)(81)

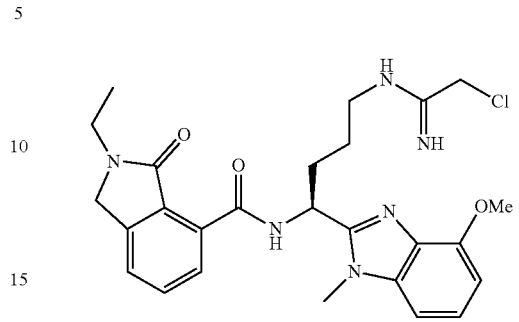

$^1$H NMR (CD$_3$OD; 400 MHz): δ 8.17 (dd, J=1.1 Hz, J=7.8 Hz, 1H), 7.79 (dd, J=1.3 Hz, J=7.9 Hz, 1H), 7.72 (t, J=7.6 Hz, 1H), 7.56 (t, J=8.4 Hz, 1H), 7.43 (dd, J=1.1 Hz, J=8.7 Hz, 1H), 7.12 (d, J=8.1 Hz, 1H), 5.62-5.59 (m, 1H), 4.63 (s, 2H), 4.39 (s, 2H), 4.19 (s, 3H), 4.01 (s, 3H), 3.82-3.71 (m, 2H), 3.50-3.46 (m, 2H), 2.44-2.26 (m, 2H), 2.15-2.05 (m, 1H), 2.00-1.87 (m, 1H), 1.34 (t, J=7.3 Hz, 3H). $^{13}$C NMR (100 MHz, CD$_3$OD) δ 168.4, 166.1, 163.3, 152.5, 148.4, 147.8, 143.7, 134.2, 131.4, 130.2, 129.9, 129.2, 127.2, 126.8, 106.5, 103.8, 55.2, 49.4, 46.8, 41.9, 38.6, 37.5, 30.9, 28.7, 23.6, 11.9. HRMS m/z calculated for C$_{26}$H$_{31}$ClN$_6$O$_3$ (M+H$^+$) 511.2219; found 511.2220.

(N1-(2-ethyl-3-oxoisoindoline)benzoyl-N5-(2-fluoro-1-iminoethyl)-1-(4-ethoxy-1-methyl-benzo[d]imidazol-2-yl)-L-ornithine) (8m)

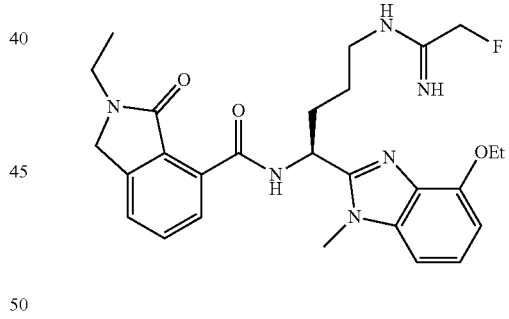

$^1$H NMR (CD$_3$OD; 500 MHz): δ 8.06 (dd, J=1.1 Hz, J=8.1 Hz, 1H), 7.69 (dd, J=1.2 Hz, J=7.6 Hz, 1H), 7.60 (t, J=7.5 Hz, 1H), 7.42 (t, J=8.4 Hz, 1H), 7.30 (dd, J=1.0 Hz, J=8.2 Hz, 1H), 6.98 (d, J=8.2 Hz, 1H), 5.52-5.48 (m, 1H), 5.18 (d, J=45.6 Hz, 2H), 4.52 (s, 2H), 4.19-4.14 (m, 2H), 4.08 (s, 3H), 3.70-3.62 (m, 2H), 3.43-3.39 (m, 2H), 2.35-2.26 (m, 1H), 2.24-2.16 (m, 1H), 2.04-1.95 (m, 1H), 1.87-1.78 (m, 1H), 1.36 (t, J=7.1 Hz, 3H), 1.25 (t, J=7.1 Hz, 3H). $^{13}$C NMR (125 MHz, CD$_3$OD) δ 168.5, 166.2, 152.5, 147.2, 143.8, 134.3, 131.4, 130.3, 129.8, 129.4, 127.1, 126.7, 121.6, 107.2, 103.7, 78.3, 76.9, 64.5, 49.3, 46.8, 41.5, 37.5, 30.9, 28.8, 23.8, 13.4, 12.0. HRMS m/z calculated for C$_{27}$H$_{33}$FN$_6$O$_3$ (M+H$^+$) 509.2671; found 509.2676.

91

(N1-(2-ethyl-3-oxoisoindoline)benzoyl-N5-(2chloro-1-iminoethyl)-1-(4-ethoxy-1-methyl-benzo[d]imidazol-2-yl)-L-ornithine) (8n)

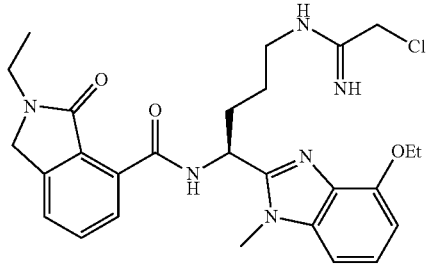 [SMILES: CCOc1cccc2c1nc([C@H](CCCNC(=N)CCl)NC(=O)c1cccc3c1C(=O)N(CC)C3)n2C]

¹H NMR (CD₃OD; 500 MHz): δ 8.05 (dd, J=1.1 Hz, J=8.0 Hz, 1H), 7.68 (dd, J=1.1 Hz, J=7.6 Hz, 1H), 7.60 (t, J=7.8 Hz, 1H), 7.41 (t, J=8.2 Hz, 1H), 7.28 (dd, J=1.0 Hz, J=8.6 Hz, 1H), 6.96 (d, J=8.2 Hz, 1H), 5.52-5.49 (m, 1H), 4.51 (s, 2H), 4.30 (s, 2H), 4.17-4.12 (m, 2H), 4.08 (s, 3H), 3.68-3.64 (m, 2H), 3.40-3.37 (m, 2H), 2.35-2.26 (m, 1H), 2.25-2.18 (m, 1H), 2.05-1.95 (m, 1H), 1.87-1.78 (m, 1H), 1.35 (t, J=7.2 Hz, 3H), 1.25 (t, J=7.3 Hz, 3H). ¹³C NMR (125 MHz, CD₃OD) δ 168.5, 166.2, 163.3, 152.6, 147.3, 143.6, 134.4, 131.4, 130.3, 129.8, 129.3, 127.0, 126.6, 121.9, 107.2, 103.7, 64.6, 49.2, 46.9, 42.0, 38.7, 37.5, 30.9, 28.9, 23.7, 13.5, 12.1. HRMS m/z calculated for $C_{27}H_{33}ClN_6O_3$ (M+H⁺) 525.2375; found 525.2378.

(N1-(2-ethyl-3-oxoisoindoline)benzoyl-N5-(2-fluoro-1-iminoethyl)-1-(5-methoxy-1-methyl-benzo[d]imidazol-2-yl)-L-ornithine) (8o)

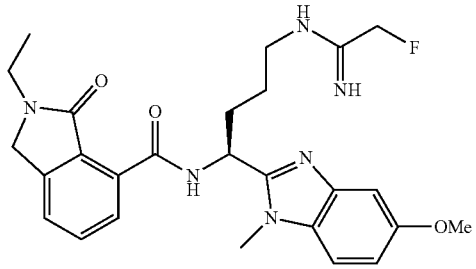 [SMILES: CCN1Cc2cccc(C(=O)N[C@@H](CCCNC(=N)CF)c3nc4cc(OC)ccc4n3C)c2C1=O]

¹H NMR (CD₃OD; 500 MHz): δ 8.06 (dd, J=1.2 Hz, J=7.9 Hz, 1H), 7.70 (m, 2H), 7.63-7.59 (t, J=7.9 Hz, 1H), 7.14 (dd, J=2.4 Hz, J=9.2 Hz, 1H), 7.09 (d, J=2.3 Hz, 1H), 5.52-5.49 (m, 1H), 5.18 (d, J=45.3 Hz, 2H), 4.53 (s, 2H), 4.09 (s, 3H), 3.77 (s, 3H), 3.69-3.64 (m, 2H), 3.47-3.37 (m, 2H), 2.31-2.16 (m, 2H), 2.04-1.95 (m, 1H), 1.90-1.81 (m, 1H), 1.25 (t, J=7.4 Hz, 3H). ¹³C NMR (125 MHz, CD₃OD) δ 168.6, 166.2, 161.0, 159.6, 152.2, 143.7, 131.4, 130.3, 129.8, 129.3, 127.0, 126.7, 116.3, 113.1, 95.9, 78.3, 76.9, 55.1, 49.3, 46.7, 41.4, 37.5, 30.9, 28.7, 23.8, 12.0. HRMS m/z calculated for $C_{26}H_{31}FN_6O_3$ (M+H⁺) 495.2514; found 495.2514.

92

(N1-(2-ethyl-3-oxoisoindoline)benzoyl-N5-(2-chloro-1-iminoethyl)-1-(5-methoxy-1-methyl-benzo[d]imidazol-2-yl)-L-ornithine) (8p)

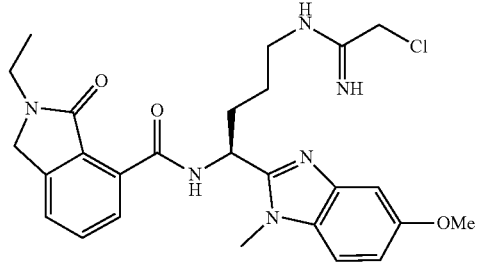 [SMILES: CCN1Cc2cccc(C(=O)N[C@@H](CCCNC(=N)CCl)c3nc4cc(OC)ccc4n3C)c2C1=O]

¹H NMR (CD₃OD; 500 MHz): δ 8.05 (dd, J=1.1 Hz, J=7.7 Hz, 1H), 7.70-7.67 (m, 2H), 7.61 (t, J=7.6 Hz, 1H), 7.13 (dd, J=2.5 Hz, J=9.1 Hz, 1H), 7.09 (d, J=2.4 Hz, 1H), 5.52-5.49 (m, 2H), 4.52 (s, 2H), 4.30 (s, 3H), 4.09 (s, 3H), 3.77 (s, 3H), 3.69-3.63 (m, 2H), 3.41-3.38 (m, 2H), 2.32-2.16 (m, 2H), 2.05-1.96 (m, 1H), 1.91-1.82 (m, 1H), 1.24 (t, J=7.2 Hz, 3H). ¹³C NMR (125 MHz, CD₃OD) δ 168.6, 166.3, 163.4, 160.8, 152.2, 143.7, 131.4, 130.2, 129.8, 129.3, 127.0, 126.7, 125.7, 116.2, 113.1, 95.9, 55.2, 49.3, 46.8, 41.9, 38.7, 37.5, 30.9, 28.8, 23.6, 12.0. HRMS m/z calculated for $C_{26}H_{31}ClN_6O_3$ (M+H⁺) 511.2219; found 511.2218.

(N1-(2-ethyl-3-oxoisoindoline)benzoyl-N5-(2-fluoro-1-iminoethyl)-1-(4-methoxy-1-isopropyl-benzo[d]imidazol-2-yl)-L-ornithine) (8q)

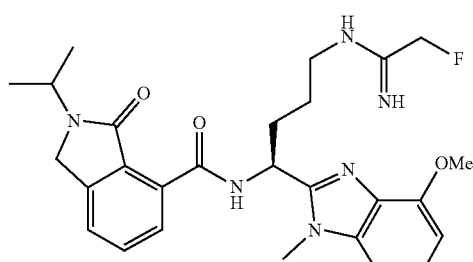

¹H NMR (CD₃OD; 500 MHz): δ 8.06 (d, J=7.9 Hz, 1H), 7.70 (d, J=8.0 Hz, 1H), 7.61 (t, J=8.2 Hz, 1H), 7.44 (t, J=8.2 Hz, 1H), 7.31 (d, J=8.2 Hz, 1H), 7.01 (d, J=8.0 Hz, 1H), 5.52-5.49 (m, 1H), 5.18 (d, J=45.2 Hz, 2H), 4.57-4.51 (m, 1H), 4.49 (s, 2H), 4.07 (s, 3H), 3.91 (s, 3H), 3.44-3.37 (m, 2H), 2.33-2.25 (m, 1H), 2.24-2.17 (m, 1H), 2.04-1.95 (m, 1H), 1.87-1.78 (m, 1H), 1.29 (d, J=2.8 Hz, 3H), 1.28 (d, J=2.7 Hz, 3H). ¹³C NMR (125 MHz, CD₃OD) δ 168.2, 166.1, 152.6, 148.0, 143.8, 134.5, 131.3, 130.3, 129.9, 129.5, 127.1, 126.8, 121.9, 106.5, 103.9, 78.3, 76.9, 55.3, 46.8, 45.4, 44.1, 41.4, 30.9, 28.8, 23.8, 19.3, 19.2. HRMS m/z calculated for $C_{27}H_{33}FN_6O_3$ (M+H⁺) 509.2669; found 509.2674.

93

(N1-(2-ethyl-3-oxoisoindoline)benzoyl-N5-(2-chloro-1-iminoethyl)-1-(4-methoxy-1-isopropyl-benzo[d]imidazol-2-yl)-L-ornithine) (8r)

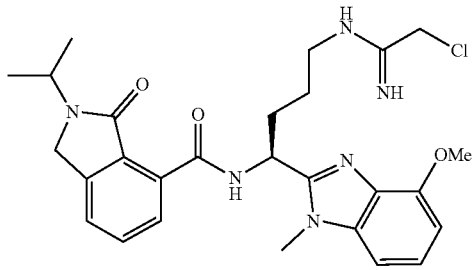 [SMILES: COc1cccc2c1nc([C@H](CCCNC(=N)CCl)NC(=O)c1cccc3c1C(=O)N(C(C)C)C3)n2C]

$^1$H NMR (CD$_3$OD; 500 MHz): δ 8.03 (d, J=8.1 Hz, 1H), 7.68 (d, J=7.7 Hz, 1H), 7.58 (t, J=7.8 Hz, 1H), 7.43 (t, J=7.9 Hz, 1H), 7.31 (d, J=8.1 Hz, 1H), 6.99 (d, J=8.1 Hz, 1H), 5.53-5.50 (m, 1H), 4.59-4.51 (m, 1H), 4.47 (s, 2H), 4.31 (s, 2H), 4.09 (s, 3H), 3.89 (s, 3H), 3.41-3.38 (m, 2H), 2.34-2.27 (m, 1H), 2.25-2.18 (m, 1H), 2.05-1.96 (m, 1H), 1.89-1.79 (m, 1H), 1.29 (d, J=2.5 Hz, 3H), 1.27 (d, J=2.5 Hz, 3H). $^{13}$C NMR (125 MHz, CD$_3$OD) δ 168.1, 166.2, 163.4, 152.6, 147.8, 143.8, 134.2, 131.3, 130.2, 129.8, 129.5, 127.3, 126.8, 121.2, 106.7, 104.0, 55.4, 46.9, 43.6, 44.0, 42.0, 38.7, 31.1, 28.8, 23.7, 19.3, 19.3. HRMS m/z calculated for C$_{27}$H$_{33}$ClN$_6$O$_3$ (M+H$^+$) 525.2374; found 525.2381.

(N1-(2-ethyl-3-oxoisoindoline)benzoyl-N5-(2-fluoro-1-iminoethyl)-1-(4-methoxy-1-cyclopropyl-benzo[d]imidazol-2-yl)-L-ornithine) (8s)

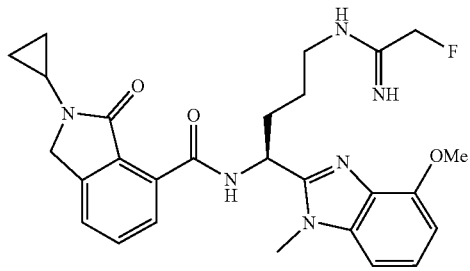 [SMILES: COc1cccc2c1nc([C@H](CCCNC(=N)CF)NC(=O)c1cccc3c1C(=O)N(C1CC1)C3)n2C]

$^1$H NMR (CD$_3$OD; 500 MHz): δ 8.03 (d, J=8.2 Hz, 1H), 7.64 (d, J=8.1 Hz, 1H), 7.58 (t, J=7.5 Hz, 1H), 7.44 (t, J=8.2 Hz, 1H), 7.31 (d, J=8.1 Hz, 1H), 6.99 (d, J=8.2 Hz, 1H), 5.52-5.49 (m, 1H), 5.20 (d, J=45.5 Hz, 2H), 4.42 (s, 2H), 4.09 (s, 3H), 3.90 (s, 3H), 3.47-3.37 (m, 2H), 3.02-2.98 (m, 1H), 2.34-2.26 (m, 1H), 2.25-2.17 (m, 1H), 2.04-1.95 (m, 1H), 1.88-1.79 (m, 1H), 0.93-0.84 (m, 4H). $^{13}$C NMR (125 MHz, CD$_3$OD) δ 170.3, 166.1, 152.6, 147.9, 143.7, 134.3, 131.5, 130.3, 129.8, 129.4, 127.3, 126.7, 121.4, 106.6, 104.0, 78.4, 76.9, 55.4, 50.0, 46.9, 41.4, 31.1, 28.8, 25.6, 23.8, 4.7, 4.5. HRMS m/z calculated for C$_{27}$H$_{31}$FN$_6$O$_3$ (M+H$^+$) 507.2512; found 507.2516.

94

(N1-(2-ethyl-3-oxoisoindoline)benzoyl-N5-(2-chloro-1-iminoethyl)-1-(4-methoxy-1-cyclopropyl-benzo[d]imidazol-2-yl)-L-ornithine)(8t)

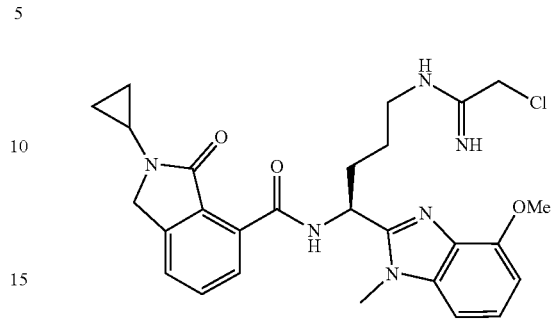

$^1$H NMR (CD$_3$OD; 500 MHz): δ 8.02 (d, J=8.0 Hz, 1H), 7.63 (d, J=8.1 Hz, 1H), 7.58 (t, J=8.1 Hz, 1H), 7.43 (t, J=8.2 Hz, 1H), 7.31 (d, J=8.2 Hz, 1H), 6.99 (d, J=8.2 Hz, 1H), 5.53-5.49 (m, 1H), 4.42 (s, 2H), 4.32 (s, 2H), 4.09 (s, 3H), 3.90 (s, 3H), 3.42-3.38 (m, 2H), 3.02-2.98 (m, 1H), 2.35-2.27 (m, 1H), 2.25-2.18 (m, 1H), 2.05-1.96 (m, 1H), 1.88-1.79 (m, 1H), 0.92-0.85 (m, 4H). $^{13}$C NMR (125 MHz, CD$_3$OD) δ 170.3, 166.2, 163.5, 152.6, 147.8, 143.7, 134.2, 131.5, 130.2, 129.7, 129.3, 127.3, 126.6, 121.3, 106.6, 103.9, 55.3, 49.9, 46.9, 41.8, 38.8, 31.0, 28.7, 25.6, 23.6, 4.8, 4.5. HRMS m/z calculated for C$_{27}$H$_{31}$ClN$_6$O$_3$ (M+H$^+$) 523.2216; found 523.2225.

(N1-(2-ethyl-3-oxoisoindoline)benzoyl-N5-(2-fluoro-1-iminoethyl)-1-(4-methoxy-1-ethyl-benzo[d]imidazol-2-yl)-L-ornithine) (8u)

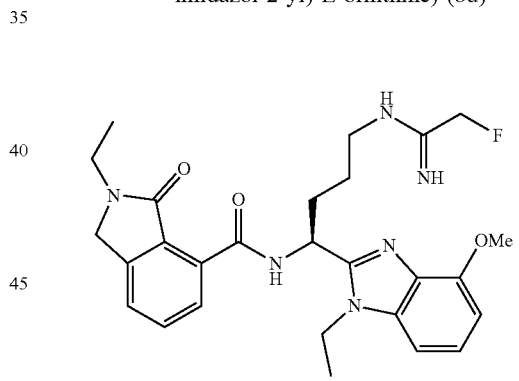

$^1$H NMR (CD$_3$OD; 500 MHz): δ 8.07 (dd, J=1.5 Hz, J=7.9 Hz, 1H), 7.69 (dd, J=1.5 Hz, J=7.4 Hz, 1H), 7.61 (t, J=7.7 Hz, 1H), 7.44 (t, J=8.1 Hz, 1H), 7.34 (dd, J=1.0 Hz, J=8.2 Hz, 1H), 7.01 (d, J=8.3 Hz, 1H), 5.53-5.49 (m, 1H), 5.19 (d, J=45.2 Hz, 2H), 4.66-4.58 (m, 1H), 4.57-4.54 (m, 1H), 4.53 (s, 2H), 3.91 (s, 3H), 3.73-3.61 (m, 2H), 3.43-3.39 (m, 2H), 2.33-2.25 (m, 1H), 2.22-2.14 (m, 1H), 2.05-1.96 (m, 1H), 1.90-1.80 (m, 1H), 1.49 (t, J=7.2 Hz, 3H), 1.25 (t, J=7.4 Hz, 3H). $^{13}$C NMR (125 MHz, CD$_3$OD) δ 168.6, 166.0, 152.2, 148.1, 143.7, 133.3, 131.4, 130.3, 129.8, 129.2, 127.2, 126.8, 121.8, 106.6, 104.1, 78.2, 76.9, 55.2, 49.2, 46.9, 41.5, 40.7, 37.7, 29.3, 23.9, 13.3, 12.2. HRMS m/z calculated for C$_{27}$H$_{33}$FN$_6$O$_3$ (M+H$^+$) 509.2671; found 509.2671.

95

(N1-(2-ethyl-3-oxoisoindoline)benzoyl-N5-(2-chloro-1-iminoethyl)-1-(4-methoxy-1-ethyl-benzo[d]imidazol-2-yl)-L-ornithine) (8v)

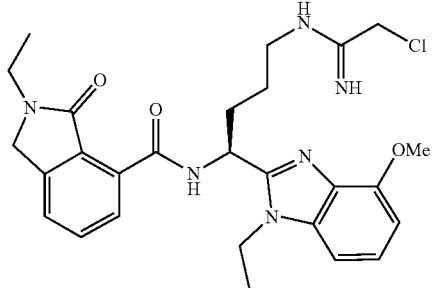 [SMILES: CCN1Cc2cccc(C(=O)N[C@@H](CCCNC(=N)CCl)c3nc4c(OC)cccc4n3CC)c2C1=O]

¹H NMR (CD₃OD; 500 MHz): δ 8.06 (dd, J=1.4 Hz, J=8.1 Hz, 1H), 7.69 (dd, J=1.3 Hz, J=8.1 Hz, 1H), 7.60 (t, J=7.7 Hz, 1H), 7.45 (t, J=8.4 Hz, 1H), 7.34 (dd, J=1.0 Hz, J=8.2 Hz, 1H), 7.00 (d, J=7.7 Hz, 1H), 5.53-5.50 (m, 1H), 4.65-4.59 (m, 1H), 4.58-4.53 (m, 1H), 4.52 (s, 2H), 4.30 (s, 2H), 3.90 (s, 3H), 3.71-3.62 (m, 2H), 3.41-3.37 (m, 2H), 2.33-2.25 (m, 1H), 2.23-2.15 (m, 1H), 2.06-1.97 (m, 1H), 1.91-1.81 (m, 1H), 1.50 (t, J=7.4 Hz, 3H), 1.25 (t, J=7.2 Hz, 3H). ¹³C NMR (125 MHz, CD₃OD) δ 168.5, 166.1, 163.3, 152.2, 148.0, 143.8, 133.2, 131.4, 130.4, 129.8, 129.3, 127.3, 126.8, 121.9, 106.5, 104.0, 55.4, 49.3, 46.9, 42.0, 40.7, 38.8, 37.7, 29.4, 23.8, 13.3, 12.1. HRMS m/z calculated for $C_{27}H_{33}ClN_6O_3$ (M+H⁺) 525.2375; found 525.2374.

(N1-(2-ethyl-3-oxoisoindoline)benzol-N5-(2-fluoro-1-iminoethyl)-1-(5-methoxy-1H-benzo[d]imidazol-2-yl)-L-ornithine) (7w)

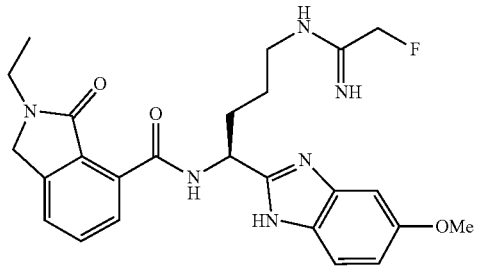 [SMILES: CCN1Cc2cccc(C(=O)N[C@@H](CCCNC(=N)CF)c3nc4cc(OC)ccc4[nH]3)c2C1=O]

¹H NMR (500 MHz, CD₃OD) δ 8.03 (dd, J=2.5 Hz, J=8.7 Hz, 1H), 7.69 (d, J=8.1 Hz, 1H), 7.62 (t, J=8.2 Hz, 1H), 7.53 (d, J=8.8 Hz, 1H), 7.12 (s, 1H), 7.07 (dd, J=2.3 Hz, J=9.1 Hz, 1H), 5.49-5.46 (m, 1H), 5.18 (d, J=45.1 Hz, 2H), 4.53 (s, 2H), 3.78 (s, 3H), 3.69-3.65 (m, 2H), 3.42-3.38 (m, 1H), 3.27-3.22 (m, 1H), 1.95-1.79 (m, 2H), 1.24 (t, J=8.4 Hz, 3H). ¹³C NMR (125 MHz, CD₃OD) δ 168.6, 166.7, 161.7, 161.4, 161.2, 159.0, 153.4, 143.6, 132.3, 131.4, 130.3, 129.9, 129.1, 126.5, 125.3, 116.0, 114.3, 95.7, 78.2, 76.7, 55.0, 49.2, 44.2, 41.3, 38.8, 37.5, 29.6, 26.0, 23.7, 12.0. HRMS m/z calculated for $C_{25}H_{29}FN_6O_3$ (M+H⁺) 481.2358; found 481.2357.

96

(N1-(2-ethyl-3-oxoisoindoline)benzoyl-N5-(2-chloro-1-iminoethyl)-1-(5-methoxy-1H-benzo[d]imidazol-2-yl)-L-ornithine) (7x)

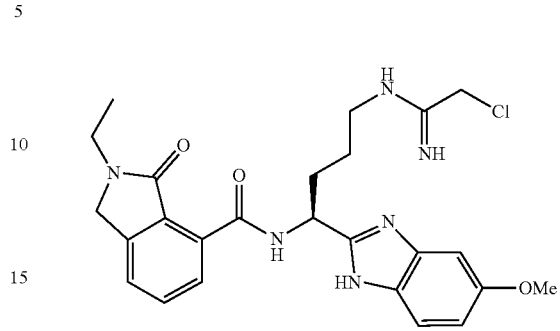

¹H NMR (500 MHz, CD₃OD) δ 8.02 (t, J=6.5 Hz, 1H), 7.68 (d, J=8.1 Hz, 1H), 7.61 (t, J=7.6 Hz, 1H), 7.52 (d, J=8.5 Hz, 1H), 7.11 (s, 1H), 7.06 (dd, J=2.1 Hz, J=8.6 Hz, 1H), 5.50-5.47 (m, 1H), 4.52 (s, 3H), 4.29 (s, 2H), 3.77 (s, 3H), 3.69-3.63 (m, 2H), 3.40-3.36 (m, 1H), 3.28-3.22 (m, 1H), 2.27-2.19 (m, 2H), 1.95-1.80 (m, 2H), 1.24 (t, J=6.9 Hz, 3H). ¹³C NMR (125 MHz, CD₃OD) δ 168.4, 166.7, 163.4, 161.7, 161.2, 161.0, 159.1, 153.5, 143.6, 133.2, 131.3, 130.3, 129.9, 129.1, 126.4, 125.7, 125.2, 116.1, 114.3, 95.8, 55.1, 49.3, 44.1, 41.9, 38.8, 37.5, 29.7, 29.6, 25.9, 23.5, 22.4, 12.1. HRMS m/z calculated for $C_{25}H_{29}ClN_6O_3$ (M+H⁺) 497.2062; found 497.2063.

(N1-(2-ethyl-3-oxoisoindoline)benzoyl-N5-(2-fluoro-1-iminoethyl)-1-(5-methoxy-1-ethyl-benzo[d]imidazol-2-yl)-L-ornithine) (7y)

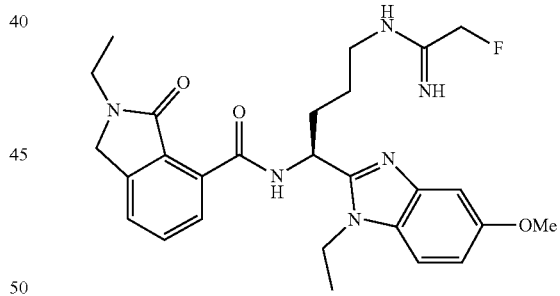

¹H NMR (500 MHz, CD₃OD) δ 8.19 (d, J=8.2 Hz, 1H), 7.82 (t, J=6.6 Hz, 2H), 7.73 (t, J=7.8 Hz, 1H), 7.26-7.22 (m, 2H), 5.65-5.62 (m, 1H), 5.32 (d, J=45.6 Hz, 2H), 4.78-4.67 (m, 2H), 4.65 (s, 2H), 3.90 (s, 3H), 3.82-3.77 (m, 2H), 3.60-3.51 (m, 2H), 2.46-2.37 (m, 1H), 2.35-2.27 (m, 1H), 2.19-2.10 (m, 1H), 2.05-1.96 (m, 1H), 1.64 (t, J=8.0 Hz, 3H), 1.37 (t, J=7.4 Hz, 3H). ¹³C NMR (125 MHz, CD₃OD) δ 168.5, 166.2, 163.1, 163.0, 159.3, 152.0, 143.7, 131.9, 131.3, 130.3, 129.8, 129.3, 126.8, 125.8, 116.3, 113.2, 96.1, 78.3, 76.9, 55.1, 49.3, 46.7, 41.5, 40.6, 37.5, 29.3, 23.8, 13.4, 12.1. HRMS m/z calculated for $C_{27}H_{33}FN_6O_3$ (M+H⁺) 509.2671; found 509.2670.

(N1-(2-ethyl-3-oxoisoindoline)benzoyl-N5-(2-chloro-1-iminoethyl)-1-(5-methoxy-1-ethyl-benzo[d]imidazol-2-yl)-L-ornithine) (7z)

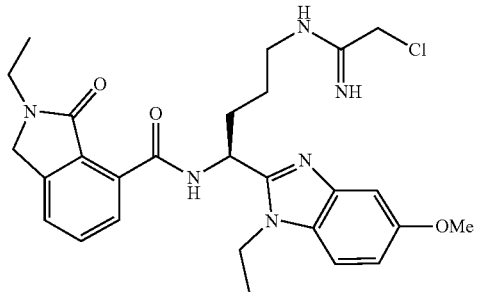 [SMILES: CCN1Cc2cccc(C(=O)N[C@@H](CCCNC(=N)CCl)c3nc4cc(OC)ccc4n3CC)c2C1=O]

$^1$H NMR (500 MHz, CD$_3$OD) δ 8.06 (d, J=7.7 Hz, 1H), 7.70 (t, J=7.0 Hz, 2H), 7.61 (t, J=7.7 Hz, 1H), 7.14-7.09 (m, 2H), 5.53-5.49 (m, 1H), 4.65-4.54 (m, 2H), 4.53 (s, 2H), 4.30 (s, 2H), 3.77 (s, 3H), 3.69-3.64 (m, 2H), 3.42-3.38 (m, 2H), 2.32-2.24 (m, 1H), 2.22-2.15 (m, 1H), 2.06-1.98 (m, 1H), 1.93-1.84 (m, 1H), 1.51 (t, J=7.0 Hz, 3H), 1.24 (t, J=7.0 Hz, 3H). $^{13}$C NMR (125 MHz, CD$_3$OD) δ 168.5, 166.2, 163.4, 161.0, 159.5, 151.9, 143.7, 131.9, 131.4, 130.3, 129.8, 129.3, 126.8, 125.9, 116.3, 113.3, 96.1, 55.1, 49.3, 46.7, 41.9, 40.7, 38.7, 37.5, 29.3, 23.6, 13.4, 12.0. HRMS m/z calculated for C$_{27}$H$_{33}$ClN$_6$O$_3$ (M+H$^+$) 525.2375; found 525.2378.

(N1-(2-methyl-3-oxoisoindoline)benzoyl-N5-(2-fluoro-1-iminoethyl)-1-(4-methoxy-1-ethyl-benzo[d]imidazol-2-yl)-L-ornithine) (8a')

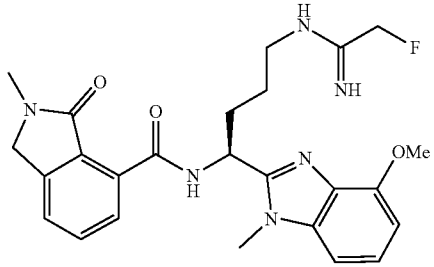 [SMILES: COc1cccc2c1nc([C@H](CCCNC(=N)CF)NC(=O)c1cccc3c1C(=O)N(C)C3)n2C]

$^1$H NMR (500 MHz, CD$_3$OD) δ 8.05 (d, J=8.1 Hz, 1H), 7.67 (d, J=8.1 Hz, 1H), 7.59 (t, J=7.4 Hz, 1H), 7.45 (t, J=9.1 Hz, 1H), 7.32 (d, J=9.1 Hz, 1H), 7.01 (d, J=8.1 Hz, 1H), 5.52-5.49 (m, 1H), 5.19 (d, J=45.6 Hz, 2H), 4.50 (s, 2H), 4.09 (s, 3H), 3.90 (s, 3H), 3.44-3.39 (m, 2H), 3.18 (s, 3H), 2.34-2.26 (m, 1H), 2.23-2.16 (m, 1H), 2.05-1.96 (m, 1H), 1.88-1.80 (m, 1H). $^{13}$C NMR (125 MHz, CD$_3$OD) 168.9, 166.1, 163.2, 163.0, 161.1, 160.8, 152.5, 147.8, 143.6, 134.2, 131.4, 130.3, 129.6, 129.1, 127.3, 126.6, 121.3, 106.7, 104.0, 78.3, 76.9, 55.3, 51.8, 46.8, 41.4, 31.0, 29.0, 28.7, 23.8. HRMS m/z calculated for C$_{25}$H$_{29}$FN$_6$O$_3$ (M+H$^+$) 481.2358; found 481.2359.

(N1-(2-methyl-3-oxoisoindoline)benzoyl-N5-(2-chloro-1-iminoethyl)-1-(4-methoxy-1-ethyl-benzo[d]imidazol-2-yl)-L-ornithine) (8b')

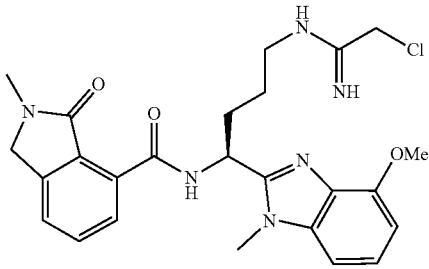 [SMILES: COc1cccc2c1nc([C@H](CCCNC(=N)CCl)NC(=O)c1cccc3c1C(=O)N(C)C3)n2C]

$^1$H NMR (500 MHz, CD$_3$OD) δ 8.05 (d, J=7.6 Hz, 1H), 7.67 (d, J=7.7 Hz, 1H), 7.59 (t, J=7.4 Hz, 1H), 7.44 (t, J=8.3 Hz, 1H), 7.32 (d, J=8.3 Hz, 1H), 7.01 (d, J=8.8 Hz, 1H), 5.52-5.49 (m, 1H), 4.50 (s, 2H), 4.31 (s, 2H), 4.09 (s, 3H), 3.90 (s, 3H), 3.41-3.38 (m, 2H), 3.18 (s, 3H), 2.34-2.26 (m, 1H), 2.25-2.17 (m, 1H), 2.05-1.96 (m, 1H), 1.89-1.80 (m, 1H). $^{13}$C NMR (125 MHz, CD$_3$OD) δ 168.9, 166.1, 163.4, 161.1, 160.7, 152.6, 147.8, 143.6, 134.3, 131.4, 130.3, 129.7, 129.2, 127.3, 126.6, 121.3, 106.7, 103.9, 55.3, 51.8, 46.8, 41.9, 38.7, 31.1, 29.0, 28.8, 23.7. HRMS m/z calculated for C$_{25}$H$_{29}$ClN$_6$O$_3$ (M+H$^+$) 497.2062; found 497.2062.

6. General Procedure for Synthesis of Benzimidazole Haloacetamidines 9a-f.$^a$

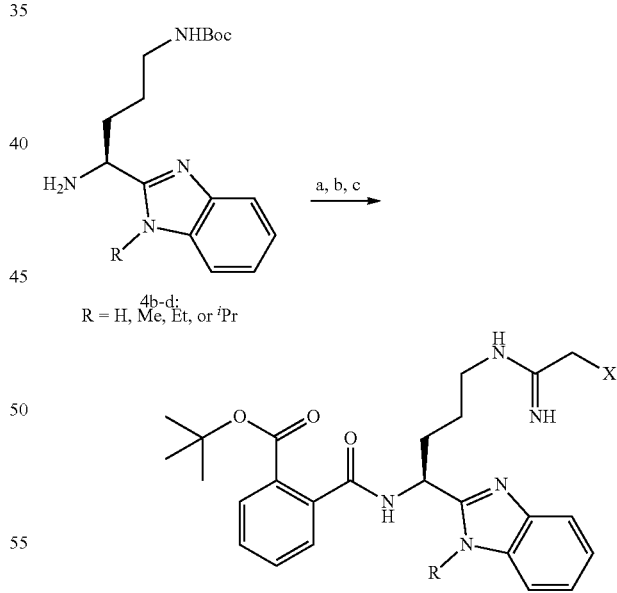

$^a$Reagents: (a) 2-(tert-butoxycarbonyl)benzoic acid, HOBt, HBTU, DIPEA, DMF; (b) 1M HCl/EtOAc; (c) ethyl 2-haloacetimidate, TEA, MeOH To a stirred solution of 4b-d (1.0 eq) in DMF was added HOBt (2.0 eq), HBTU (2.0 eq), and DIPEA (3.0 eq) followed by 2-(tert-butoxycarbonyl)benzoic acid (1.0 eq) and allowed to stir at rt for 12 h. The reaction mixture was then diluted with water. The product was filtered, washed with water, dried under vacuum, and obtained in 62-71% yield. This product was then treated with 1 M HCl in EtOAc to remove the Boc group giving the CO₂ₜBu-Bz-Orn-benzimidazole intermediate. The solvent was then evaporated to dryness and the crude material was dried in vacuo. To a stirred solution of the corresponding CO₂ᵗBu-Bz-Orn-benzimidazole intermediate in dry MeOH was added TEA (4.0 eq) followed by ethyl haloacetimidate HCl (2.0 eq). The reaction was stirred under N₂ at rt for 3 h. Solvents were then evaporated under reduced pressure and the crude product was purified by reverse phase HPLC using MeCN:H₂O (0.5% TFA) as an eluent to give compounds 9a-f in 51-67% yield.

(N1-(2-tert-butylcarboxy)benzoyl-N5-(2-fluoro-1-iminoethyl)-1-(1-methyl-benzo[d]imidazol-2-yl)-L-ornithine) (9a)

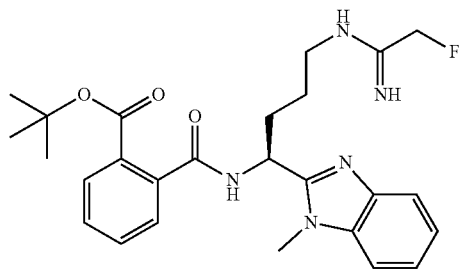 [SMILES: Cn1c([C@H](CCCNC(=N)CF)NC(=O)c2ccccc2C(=O)OC(C)(C)C)nc2ccccc21]

$^1$H NMR (CD$_3$OD; 400 MHz): δ 7.85-7.81 (m, 2H), 7.77 (dd, J=1.7 Hz, J=7.2 Hz, 1H), 7.63-7.51 (m, 4H), 7.48 (dd, J=1.3 Hz, J=7.6 Hz, 1H), 5.68-5.65 (m, 1H), 5.27 (d, J=45.3 Hz, 2H), 4.19 (s, 3H), 3.54-3.46 (m, 2H), 2.42-2.23 (m, 2H), 2.09-1.98 (m, 1H), 1.95-1.85 (m, 1H), 1.32 (s, 9H). $^{13}$C NMR (100 MHz, CD$_3$OD) δ 170.9, 165.0, 151.4, 150.0, 144.4, 143.8, 131.5, 130.4, 129.8, 129.5, 125.4, 125.2, 111.7, 100.2, 82.7, 81.0, 78.4, 76.1, 54.0, 53.2, 45.1, 40.6, 30.6, 28.4, 26.4, 23.2. HRMS m/z calculated for C$_{26}$H$_{32}$FN$_5$O$_3$ (M+H$^+$) 482.2562; found 482.2561.

(N1-(2-tert-butylcarboxy)benzol-N5-(2-chloro-1-iminoethyl)-1-(1-methyl-benzo[d]imidazol-2-yl)-L-ornithine) (9b)

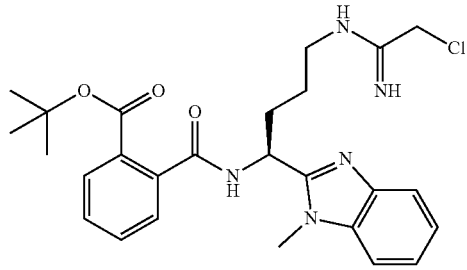 [SMILES: Cn1c([C@H](CCCNC(=N)CCl)NC(=O)c2ccccc2C(=O)OC(C)(C)C)nc2ccccc21]

$^1$H NMR (CD$_3$OD; 400 MHz): δ 7.89-7.78 (m, 3H), 7.63-7.46 (m, 5H), 5.69-5.64 (m, 1H), 4.37 (s, 2H), 4.21 (s, 3H), 3.50-3.44 (m, 2H), 2.43-2.23 (m, 2H), 2.11-1.99 (m, 1H), 1.96-1.85 (m, 1H), 1.32 (s, 9H). $^{13}$C NMR (100 MHz, CD$_3$OD) δ 165.3, 163.6, 152.3, 136.4, 131.5, 131.3, 130.4, 129.7, 129.3, 126.9, 125.3, 114.7, 111.5, 94.6, 81.2, 72.6, 72.0, 66.5, 50.0, 44.8, 42.0, 38.5, 30.2, 28.4, 26.3, 23.3. HRMS m/z calculated for C$_{26}$H$_{32}$ClN$_5$O$_3$ (M+H$^+$) 498.2266; found 498.2268.

(N1-(2-tert-butylcarboxy)benzoyl-N5-(2-fluoro-1-iminoethyl)-1-(1-ethyl-benzo[d]imidazol-2-yl)-L-ornithine) (9c)

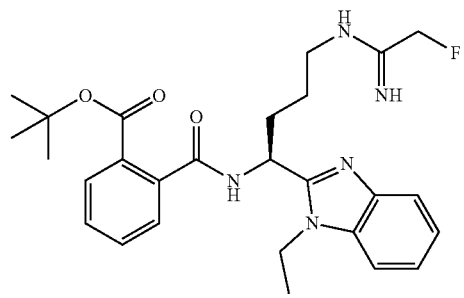 [SMILES: CCn1c([C@H](CCCNC(=N)CF)NC(=O)c2ccccc2C(=O)OC(C)(C)C)nc2ccccc21]

$^1$H NMR (CD$_3$OD; 400 MHz): δ 7.97 (dd, J=2.3 Hz, J=6.8 Hz, 1H), 7.85-7.81 (m, 2H), 7.68-7.58 (m, 3H), 7.56-7.49 (m, 2H), 5.70-5.65 (m, 1H), 5.26 (d, J=45.3 Hz, 2H), 4.89-4.81 (m, 1H), 4.76-4.68 (m, 1H), 3.50-3.45 (m, 2H), 2.42-2.20 (m, 2H), 2.12-2.00 (m, 1H), 1.94-1.81 (m, 1H), 1.64 (t, J=7.5 Hz, 3H), 1.32 (s, 9H). $^{13}$C NMR (100 MHz, CD$_3$OD) δ 171.6, 165.2, 163.3, 163.2, 162.4, 161.0, 151.7, 136.7, 131.8, 130.4, 129.7, 129.5, 127.1, 126.6, 126.3, 114.3, 112.7, 81.6, 78.6, 76.7, 45.6, 41.8, 40.4, 28.8, 26.9, 23.8, 13.4. HRMS m/z calculated for C$_{27}$H$_{34}$FN$_5$O$_3$ (M+H$^+$) 496.2718; found 496.2718.

(N1-(2-tert-butylcarboxy)benzoyl-N5-(2-chloro-1-iminoethyl)-1-(1-ethyl-benzo[d]imidazol-2-yl)-L-ornithine) (9d)

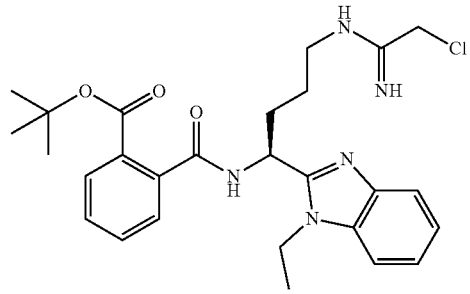 [SMILES: CCn1c([C@H](CCCNC(=N)CCl)NC(=O)c2ccccc2C(=O)OC(C)(C)C)nc2ccccc21]

$^1$H NMR (CD$_3$OD; 400 MHz): δ 7.98 (dd, J=2.1 Hz, J=7.2 Hz, 1H), 7.86-7.81 (m, 2H), 7.68-7.62 (m, 2H), 7.60 (dd, J=1.3 Hz, J=7.5 Hz, 1H), 7.56-7.49 (m, 2H), 5.70-5.65 (m, 1H), 4.90-4.82 (m, 1H), 4.77-4.68 (m, 1H), 4.38 (s, 2H), 3.48-3.43 (m, 2H), 2.43-2.21 (m, 2H), 2.15-2.02 (m, 1H), 1.95-1.83 (m, 1H), 1.64 (t, J=7.3 Hz, 3H), 1.32 (s, 9H). $^{13}$C NMR (100 MHz, CD$_3$OD) δ 171.6, 165.3, 163.3, 160.4, 160.1, 159.8, 151.4, 136.1, 132.2, 130.5, 130.2, 128.4, 127.3, 126.3, 108.9, 88.7, 81.4, 50.4, 45.9, 44.5, 38.2, 36.4, 31.7, 28.4, 27.0, 25.3, 13.8. HRMS m/z calculated for C$_{27}$H$_{34}$ClN$_5$O$_3$ (M+H$^+$) 512.2423; found 512.2422.

(N1-(2-tert-butylcarboxy)benzoyl-N5-(2-fluoro-1-iminoethyl)-1-(1-isopropyl-benzo[d]imidazol-2-yl)-L-ornithine) (9e)

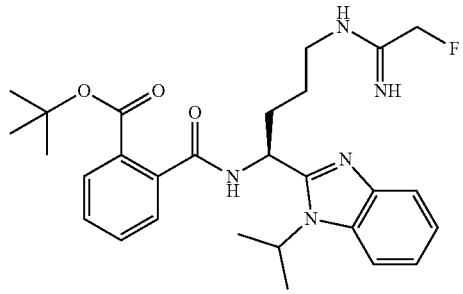 [SMILES: CC(C)n1c([C@H](CCCNC(=N)CF)NC(=O)c2ccccc2C(=O)OC(C)(C)C)nc2ccccc21]

$^1$H NMR (CD$_3$OD; 400 MHz): δ 8.12 (m, 1H), 7.86-7.81 (m, 2H), 7.64-7.58 (m, 3H), 7.55 (dd, J=1.4 Hz, J=7.7 Hz, 1H), 7.52-7.48 (m, 1H), 5.74-5.69 (m, 1H), 5.47-5.39 (m, 1H), 5.26 (d, J=45.4 Hz, 2H), 3.52-3.44 (m, 2H), 2.42-2.20 (m, 2H), 2.11-1.99 (m, 1H), 1.94-1.86 (m, 1H), 1.85 (d, J=3.3 Hz, 3H), 1.83 (d, J=3.4 Hz, 3H), 1.34 (s, 9H). $^{13}$C NMR (100 MHz, CD$_3$OD) δ 171.5, 165.3, 163.0, 161.8, 151.2, 136.3, 132.3, 131.7, 130.6, 130.2, 129.8, 129.4, 127.4, 126.0, 125.4, 114.9, 114.7, 81.4, 78.5, 76.1, 51.0, 45.1, 41.4, 28.7, 26.3, 23.7, 19.9, 19.8. HRMS m/z calculated for C$_{28}$H$_{36}$FN$_5$O$_3$ (M+H$^+$) 510.2875; found 510.2878.

(N1-(2-tert-butylcarboxy)benzoyl-N5-(2-chloro-1-iminoethyl)-1-(1-isopropyl-benzo[d]imidazol-2-yl)-L-ornithine) (9f)

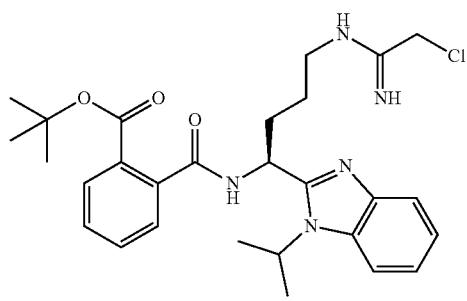 [SMILES: CC(C)n1c([C@H](CCCNC(=N)CCl)NC(=O)c2ccccc2C(=O)OC(C)(C)C)nc2ccccc21]

$^1$H NMR (CD$_3$OD; 400 MHz): δ 8.12-8.07 (m, 1H), 7.85-7.81 (m, 2H), 7.63-7.57 (m, 3H), 7.55 (dd, J=1.3 Hz, J=7.8 Hz, 1H), 7.52-7.48 (m, 1H), 5.73-5.68 (m, 1H), 5.43-5.46 (m, 1H), 4.37 (s, 2H), 3.47-3.42 (m, 2H), 2.41-2.21 (m, 2H), 2.10-1.98 (m, 1H), 1.93-1.85 (m, 1H), 1.84 (d, J=3.1 Hz, 3H), 1.82 (d, J=3.2 Hz, 3H), 1.36 (9H). $^{13}$C NMR (100 MHz, CD$_3$OD) δ 170.9, 168.8, 165.0, 163.1, 151.0, 136.4, 131.4, 130.5, 130.3, 129.7, 129.3, 127.1, 125.6, 125.2, 115.1, 114.4, 81.5, 77.0, 76.1, 50.9, 45.5, 41.8, 38.7, 28.9, 26.7, 23.4, 19.9, 19.8. HRMS m/z calculated for C$_{28}$H$_{36}$ClN$_5$O$_3$ (M+H$^+$) 526.2579; found 526.2577.

6. General Procedure for Synthesis of Benzimidazole Haloacetamidines 10a-h and 11a-h

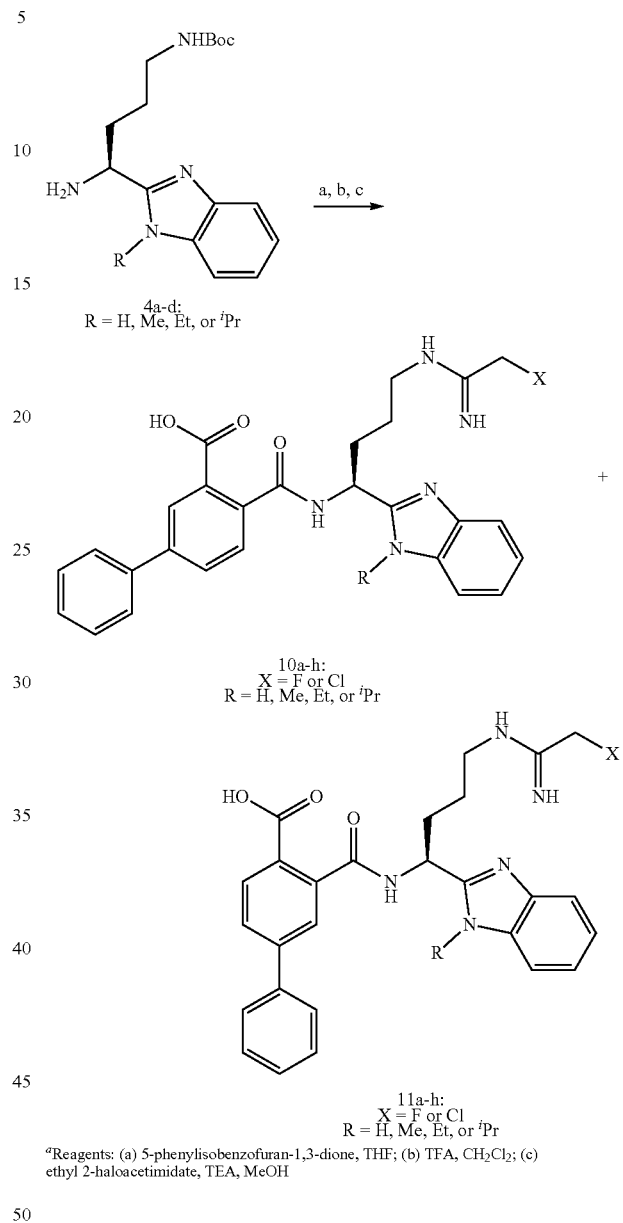

$^a$Reagents: (a) 5-phenylisobenzofuran-1,3-dione, THF; (b) TFA, CH$_2$Cl$_2$; (c) ethyl 2-haloacetimidate, TEA, MeOH To a stirred solution of 4a-d (1.0 eq) in THF was added 5-phenylisobenzofuran-1,3-dione (1.0 eq) and allowed to stir at rt under N$_2$ for 18 h. Solvents were evaporated and the crude product was purified by reverse phase HPLC using MeCN:H$_2$O (0.5% TFA) as the eluent to give the product in 78-86% yield. This product was then treated with TFA to remove the Boc group giving the 4-Ph-2-CO$_2$H-Bz-Orn-benzimidazole and 3-Ph-2-CO$_2$H-Bz-Orn intermediates as a 50:50 mixture. The solvent was then evaporated to dryness and the crude material was dried in vacuo. To a stirred solution of the corresponding 4-Ph-2-CO$_2$H-Bz-Orn-benzimidazole and 3-Ph-2-CO$_2$H-Bz-Orn mixture in dry MeOH was added TEA (4.0 eq) followed by ethyl haloacetimidate HCl (2.0 eq). The reaction was stirred under N$_2$ at rt for 3 h. Solvents were then evaporated under reduced pressure and the crude product was purified by reverse phase HPLC using MeCN:H₂O (0.5% TFA) as an eluent to give compounds 10a-h and 11a-h in 55-69% yield.

(N1-[1,4'-Phenyl](2-carboxyl)benzol-N5-(2-fluoro-1-iminoethyl)-1-(1H-benzo[d]imidazol-2-yl)-L-ornithine) (10a) and (N1-[1,3'-Phenyl](2-carboxyl)benzol-N5-(2-fluoro-1-iminoethyl)-1-(1H-benzo[d]imidazol-2-yl)-L-ornithine) (11a)

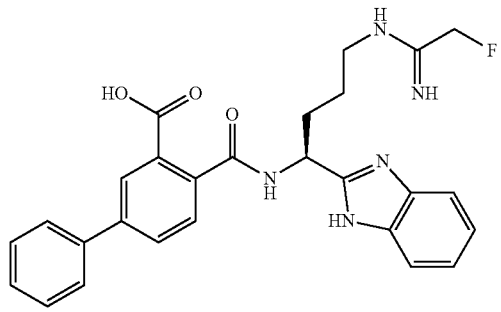

10a

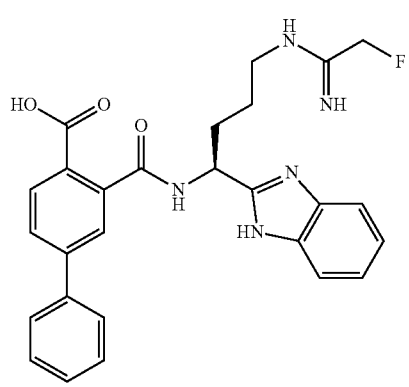

11a

Compounds 10a and 11a were isolated as a ~40:60 mixture, respectively.

¹H NMR (CD₃OD; 400 MHz): δ 8.27 (d, J=1.6 Hz, 0.4H), 8.14 (d, J=8.2 Hz, 0.6H), 7.93 (dd, J=1.4 Hz, J=7.8 Hz, 0.4H), 7.86 (dd, J=1.5 Hz, J=7.9 Hz, 0.6H), 7.81-7.63 (m, 5H), 7.54-7.48 (m, 4H), 7.43 (t, J=7.4 Hz, 1H), 5.56-5.52 (m, 1H), 5.29 (d, J=45.3 Hz, 0.4H), 5.26 (d, J=45.4 Hz, 0.6H), 3.52-3.45 (m, 2H), 2.38-2.21 (m, 2H), 2.07-1.87 (m, 2H). ¹³C NMR (125 MHz, CD₃OD) δ 171.8, 168.1, 167.9, 162.1, 154.7, 154.4, 154.2, 153.5, 145.3, 142.8, 138.9, 138.8, 138.4, 133.6, 131.0, 130.2, 129.8, 128.8, 128.5, 128.4, 128.1, 127.8, 126.9, 126.6, 126.0, 125.6, 124.8, 114.0, 99.9, 78.3, 76.9, 67.3, 41.5, 28.9, 25.1, 23.5. HRMS m/z calculated for $C_{27}H_{26}FN_5O_3$ (M+H⁺) 488.2092; found 488.2091.

(N1-[1,4'-Phenyl](2-carboxyl)benzoyl-N5-(2-chloro-1-iminoethyl)-1-(1H-benzo[d]imidazol-2-yl-L-ornithine) (10b) and (N1-[1,3'-Phenyl](2-carboxyl)benzoyl-N5-(2-chloro-1-iminoethyl)-1-(1H-benzo[d]imidazol-2-yl)-L-ornithine) (11b)

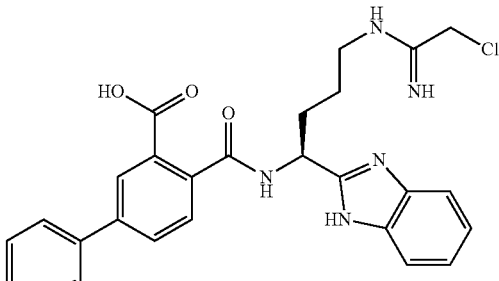

10b

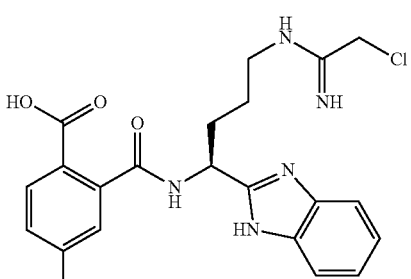

11b

Compounds 10b and 11b were isolated as a 40:60 mixture, respectively.

¹H NMR (CD₃OD; 400 MHz): δ 8.26 (d, J=1.9 Hz, 0.4H), 8.13 (d, J=8.2 Hz, 0.6H), 7.93 (dd, J=2.1 Hz, J=8.1 Hz, 0.4H), 7.85 (dd, J=1.8 Hz, J=8.2 Hz, 0.6H), 7.81-7.63 (m, 5H), 7.55-7.48 (m, 4H), 7.44 (J=7.06 Hz, 1H), 5.56-5.52 (m, 1H), 4.39 (s, 0.8H), 4.37 (s, 1.2H), 3.49-3.43 (m, 2H), 2.36-2.23 (m, 2H), 2.07-1.87 (m, 2H). ¹³C NMR (125 MHz, CD₃OD) δ 171.9, 171.8, 168.2, 167.8, 167.4, 163.2, 161.6, 161.1, 153.2, 145.1, 138.9, 138.5, 138.0, 135.9, 132.3, 131.0, 130.3, 129.8, 128.8, 128.3, 127.8, 127.3, 126.8, 126.6, 125.8, 125.3, 113.7, 41.9, 38.5, 28.9, 23.4, 20.2. HRMS m/z calculated for $C_{27}H_{26}ClN_5O_3$ (M+H⁺) 504.1797; found 504.1798.

(N1-[1,4'-Phenyl](2-carboxyl)benzol-N5-(2-fluoro-1-iminoethyl)-1-(1-methyl-benzo[d]imidazol-2-yl)-L-ornithine) (10c) and (N1-[1,3'-Phenyl](2-carboxyl)benzol-N5-(2-fluoro-1-iminoethyl)-1-(1-methyl-benzo[d]imidazol-2-yl)-L-ornithine) (11c)

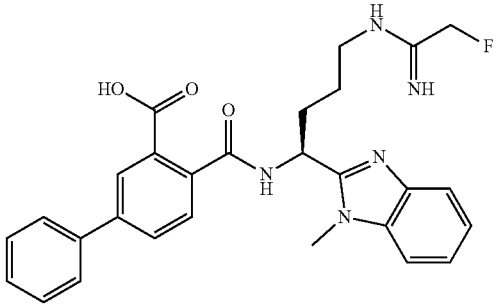

10c

-continued

11c

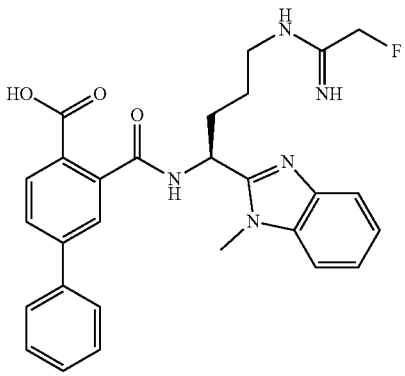

Compounds 10c and 11c were isolated as a 20:80 mixture, respectively.

$^1$H NMR (CD$_3$OD; 400 MHz): δ 8.21 (d, J=2.1 Hz, 0.2H), 8.07 (d, J=8.1 Hz, 0.8H), 7.92-7.78 (m, 3H), 7.72-7.57 (m, 5H), 7.50-7.38 (m, 2H), 5.71-5.67 (m, 1H), 5.28 (d, J=45.3 Hz, 0.2H), 5.26 (d, J=45.4 Hz, 0.8H), 4.24 (s, 3H), 3.55-3.43 (m, 2H), 2.43-2.33 (m, 1H), 2.31-2.21 (m, 1H), 2.13-2.01 (m, 1H), 1.96-1.84 (m, 1H). $^{13}$C NMR (100 MHz, CD$_3$OD) δ 171.6, 166.8, 163.1, 151.7, 145.1, 138.6, 137.6, 132.5, 130.8, 128.8, 128.3, 127.8, 127.4, 126.8, 126.6, 126.3, 125.9, 125.7, 114.9, 114.3, 112.2, 78.3, 76.6, 45.5, 41.3, 30.8, 28.3, 25.3. HRMS m/z calculated for C$_{28}$H$_{28}$FN$_5$O$_3$ (M+H$^+$) 502.2249; found 502.2255.

(N1-[1,4'-Phenyl](2-carboxyl)benzoyl-N5-(2-chloro-1-iminoethyl)-1-(1-methyl-benzo[d]imidazol-2-yl)-L-ornithine) (10d) and (N1-[1,3'-Phenyl](2-carboxyl)benzoyl-N5-(2-chloro-1-iminoethyl)-1-(1-methyl-benzo[d]imidazol-2-yl)-L-ornithine) (11d)

10d

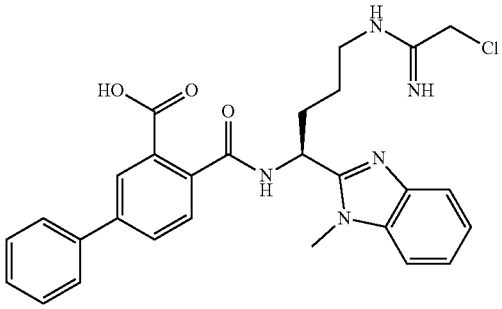

11d

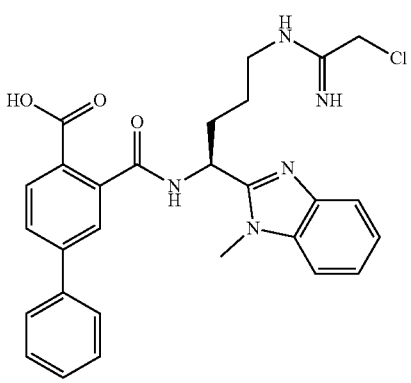

Compounds 10d and 11d were isolated as a 20:80 mixture, respectively.

$^1$H NMR (CD$_3$OD; 400 MHz): δ 8.20 (d, J=2.0 Hz, 0.2H), 8.08 (d, J=8.4 Hz, 0.8H), 7.90-7.78 (m, 3H), 7.72-7.62 (m, 2H), 7.60-7.55 (m, 3H), 7.51-7.38 (m, 2H), 5.70-5.66 (m, 1H), 4.39 (s, 1.6H), 4.38 (s, 0.4H), 4.22 (s, 2.4H), 4.21 (s, 0.6H), 3.52-3.43 (m, 2H), 2.44-2.23 (m, 1H), 2.11-1.85 (m, 1H). $^{13}$C NMR (100 MHz, CD$_3$OD) 171.9, 171.7, 168.1, 167.8, 163.3, 161.7, 161.3, 153.3, 145.2, 142.8, 138.9, 138.7, 138.3, 136.0, 132.2, 131.1, 130.2, 129.8, 128.7, 128.4, 128.3, 128.2, 128.0, 127.9, 127.4, 126.8, 126.7, 125.9, 125.5, 113.8, 41.9, 38.7, 28.9, 23.5. HRMS m/z calculated for C$_{28}$H$_{28}$ClN$_5$O$_3$ (M+H$^+$) 518.1953; found 518.1957.

(N1-[1,4'-Phenyl](2-carboxyl)benzol-N5-(2-fluoro-1-iminoethyl)-1-(1-ethyl-benzo[d]imidazol-2-yl)-L-ornithine) (10e) and (N1-[1,3'-Phenyl](2-carboxyl)benzol-N5-(2-fluoro-1-iminoethyl)-1-(1-ethyl-benzo[d]imidazol-2-yl)-L-ornithine) (11e)

10e

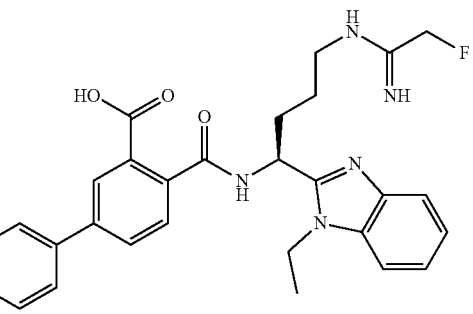

11e

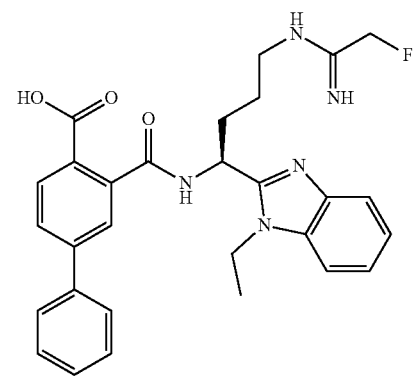

Compounds 10e and 11e were isolated as a 40:60 mixture, respectively.

$^1$H NMR (CD$_3$OD; 400 MHz): δ 8.20 (d, 0.4H), 8.07 (d, J=9.6 Hz, 0.6H), 7.94-7.80 (m, 3H) 7.73-7.57 (m, 5H), 7.48 (t, J=8.0 Hz, 2H), 7.43-7.37 (m, 1H), 5.69-5.65 (m, 1H), 5.27 (d, J=45.2 Hz, 0.8H), 5.26 (d, J=45.4 Hz, 1.2H), 4.85-4.77 (m, 1H), 4.74-4.65 (m, 1H), 3.53-3.41 (m, 2H), 2.42-2.30 (m, 1H), 2.29-2.19 (m, 1H), 2.13-2.01 (m, 1H), 1.96-1.84 (m, 1H), 1.64 (t, J=8.0 Hz, 3H). $^{13}$C NMR (100 MHz, CD$_3$OD) δ 171.7, 171.5, 167.3, 167.0, 163.0, 162.8, 161.4, 161.2, 151.6, 145.0, 142.9, 138.9, 138.8, 137.8, 135.6, 131.6, 131.5, 130.9, 130.0, 129.8, 128.7, 128.3, 128.1, 128.0, 127.9, 127.6, 126.8, 126.6, 126.3, 126.0, 125.7, 118.0, 115.1, 114.6, 112.4, 78.4, 76.7, 45.6, 41.4, 40.6, 29.0, 23.7, 13.6. HRMS m/z calculated for $C_{29}H_{30}FN_5O_3$ (M+H$^+$) 516.2405; found 516.2405.

(N1-[1,4'-Phenyl](2-carboxyl)benzol-N5-(2-chloro-1-iminoethyl)-1-(1-ethyl-benzo[d]imidazol-2-yl)-L-ornithine) (10f) and (N1-[1,3'-Phenyl](2-carboxyl)benzol-N5-(2-chloro-1-iminoethyl)-1-(1-ethyl-benzo[d]imidazol-2-yl)-L-ornithine) (11f)

(N1-[1,4'-Phenyl](2-carboxyl)benzol-N5-(2-fluoro-1-iminoethyl)-1-(1-isopropyl-benzo[d]imidazol-2-yl)-L-ornithine) (102) and (N1-[1,3'-Phenyl](2-carboxyl)benzol-N5-(2-fluoro-1-iminoethyl)-1-(1-isopropyl-benzo[d]imidazol-2-yl)-L-ornithine) (112)

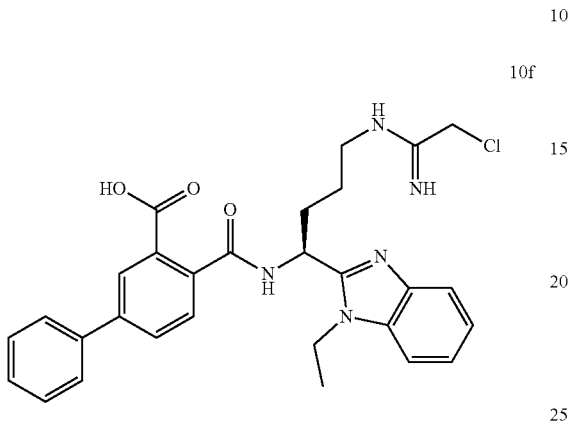

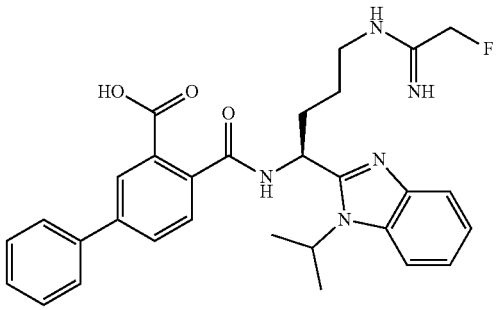

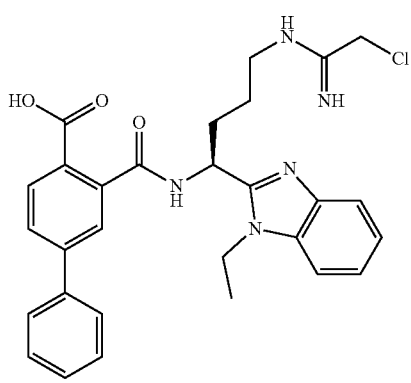

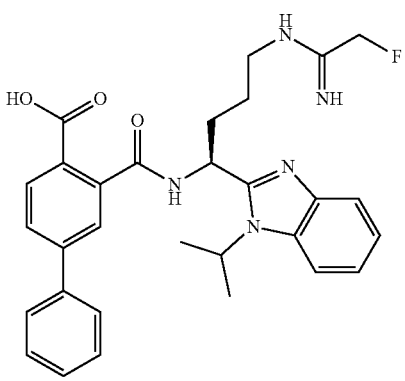

Compounds 10f and 11f were isolated as a ~40:60 mixture, respectively.

$^1$H NMR (CD$_3$OD; 400 MHz): δ 8.20 (d, J=2.3 Hz, 0.4H), 8.07 (dd, J=1.9 Hz, J=9.6 Hz, 0.6H), 7.94-7.80 (m, 3H), 7.73-7.57 (m, 5H), 7.48 (t, J=7.4 Hz, 2H), 7.43-7.38 (m, 1H), 5.70-5.65 (m, 1H), 4.86-4.76 (m, 1H), 4.73-4.65 (m, 1H), 4.39 (s, 0.8H), 4.38 (s, 1.2H), 4.37 (s, 0.4H), 4.36 (s, 0.6H), 3.50-3.40 (m, 2H), 2.41-2.31 (m, 1H), 2.29-2.20 (m, 1H), 2.13-2.02 (m, 1H), 1.96-1.85 (m, 1H), 1.64 (t, J=7.5 Hz, 3H). $^{13}$C NMR (100 MHz, CD$_3$OD) δ 171.7, 171.5, 167.4, 167.1, 163.3, 161.5, 161.2, 151.7, 145.0, 142.9, 138.9, 138.8, 137.9, 135.7, 131.7, 130.9, 130.1, 129.9, 128.8, 128.4, 128.3, 128.0, 128.0, 127.9, 127.6, 126.8, 126.6, 126.3, 126.0, 125.8, 118.0, 115.1, 114.6, 112.4, 45.6, 45.5, 41.9, 40.6, 38.7, 29.0, 28.9, 23.6, 13.6. HRMS m/z calculated for $C_{29}H_3ClN_5O_3$ (M+H$^+$) 532.2110; found 532.2112.

Compounds 10g and 11g were isolated as a 40:60 mixture, respectively.

$^1$H NMR (CD$_3$OD; 400 MHz): δ 8.20 (d, J=2.2 Hz, 0.4H), 8.11-8.04 (m, 1.6H), 7.90-7.79 (m, 2H), 7.72-7.63 (m, 3H), 7.60-7.54 (m, 2H), 7.50-7.45 (m, 2H), 7.44-7.37 (m, 1H), 5.72-5.66 (m, 1H), 5.40-5.33 (m, 1H), 5.27 (d, J=45.3 Hz, 0.4H), 5.21 (d, J=45.2 Hz, 0.6H), 3.53-3.43 (m, 2H), 2.40-2.29 (m, 1H), 2.28-2.19 (m, 1H), 2.10-1.98 (m, 1H), 1.94-1.85 (m, 1H), 1.85 (d, J=7.3 Hz, 6H). $^{13}$C NMR (100 MHz, CD$_3$OD) 171.6, 171.3, 167.4, 167.2, 163.1, 161.4, 161.0, 161.4, 151.4, 145.0, 143.0, 138.9, 138.8, 137.8, 135.6, 130.9, 130.4, 130.1, 130.0, 128.8, 128.4, 128.3, 128.0, 128.0, 127.6, 126.8, 126.6, 125.8, 125.8, 125.4, 115.1, 114.6, 78.4, 76.6, 51.1, 45.9, 45.8, 41.4, 29.2, 29.1, 23.7, 19.8, 19.8. HRMS m/z calculated for $C_3H_{32}FN_5O_3$ (M+H$^+$) 530.2562; found 530.2562.

(N1-[1,4'-Phenyl](2-carboxyl)benzol-N5-(2-chloro-1-iminoethyl)-1-(1-isopropyl-benzo[d]imidazol-2-yl)-L-ornithine) (10h) and (N1-[1,3'-Phenyl](2-carboxyl)benzol-N5-(2-chloro-1-iminoethyl)-1-(1-isopropyl-benzo[d]imidazol-2-yl)-L-ornithine) (11h)

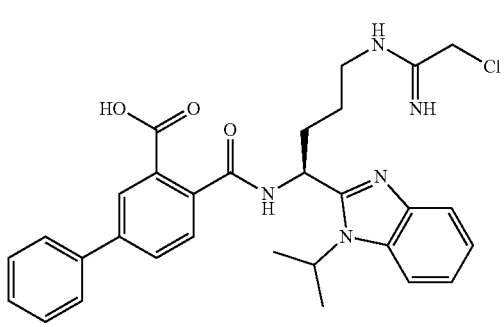

10h

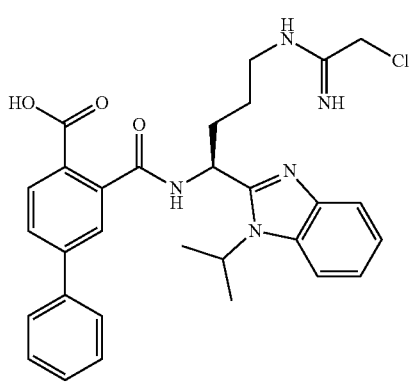

11h

Compounds 10h and 11h were isolated as a 40:60 mixture, respectively. $^1$H NMR (CD$_3$OD; 400 MHz): δ 8.20 (d, J=2.2 Hz, 0.4H), 8.10-8.06 (m, 1.6H), 7.90-7.80 (m, 2H), 7.72-7.64 (m, 3H), 7.60-7.55 (m, 2H), 7.50-7.45 (m, 2H), 7.43-7.38 (m, 1H), 5.72-5.68 (m, 1H), 5.41-5.31 (m, 1H), 4.38 (s, 0.8H), 4.37 (s, 1.2H), 3.49-3.41 (m, 2H), 2.41-2.31 (m, 1H), 2.29-2.20 (m, 1H), 2.11-1.98 (m, 1H), 1.94-1.86 (m, 1H), 1.84-1.82 (d, J=7.1 Hz, 6H). $^{13}$C NMR (100 MHz, CD$_3$OD) δ 171.6, 167.5, 167.1, 164.8, 163.3, 161.5, 161.0, 151.4, 146.7, 145.0, 142.9, 141.8, 138.8, 137.9, 137.3, 135.6, 130.9, 130.5, 130.2, 130.0, 128.7, 128.4, 128.2, 128.0, 127.9, 127.6, 126.8, 126.6, 125.7, 125.4, 115.1, 114.6, 110.0, 51.0, 45.9, 45.8, 41.9, 38.7, 29.1, 23.6, 19.9, 19.8. HRMS m/z calculated for C$_{30}$H$_{32}$FN$_5$O$_3$ (M+H$^+$) 546.2266; found 546.2270.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

The invention claimed is:

1. A compound having the structural formula (I),

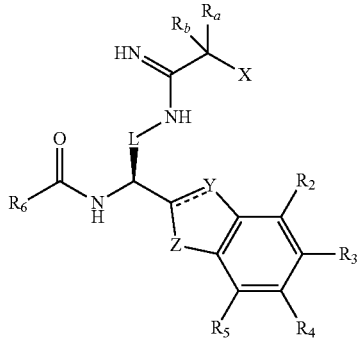

(I)

wherein
each of $R_a$ and $R_b$ is independently selected from the group consisting of H, D and F;
L is a bivalent hydrocarbyl linker, optionally with one or more carbon atoms replaced by a heteroatom selected from the group consisting of O, S and N;
X is a halogen atom;
Y is N, O or S; provided that when Y is S or O, its bonding to the adjacent carbons are single bonds;
Z is N—$R_1$, O or S;
$R_1$ is selected from the group consisting of: H, a $C_{1-6}$ alkyl, OH, a $C_{1-3}$ alkoxy, $CF_3$, $COCH_3$, or $COCF_3$ groups;
each of $R_2$, $R_3$, $R_4$ and $R_5$ is independently selected from the group consisting of: H, hydroxyl, halogen atom, $C_{1-6}$ alkyl, $C_{1-6}$ alkoxy, alkynyl, $CF_2R_c$, or $OCF_2R_c$ groups, where $R_c$ is H, F or alkyl, provided at least one of $R_2$, $R_3$, $R_4$ and $R_5$ is a group selected from the group consisting of hydroxyl, F, Cl, $C_{1-6}$ alkyl, $C_{1-6}$ alkoxy, alkynyl, $CF_2R_c$ and $OCF_2R_c$ groups; and
$R_6$ is a group comprising a cyclic alkyl or aryl moiety, or a pharmaceutically acceptable form thereof.

2. The compound of claim 1, wherein each of $R_a$ and $R_b$ is H.

3. The compound of claim 1, wherein L is a $-(CH_2)_n-$, wherein n is an integer from 1 to about 4.

4. The compound of claim 1, wherein Y is N and Z is N-$R_1$ with the compound having the structural formula (II):

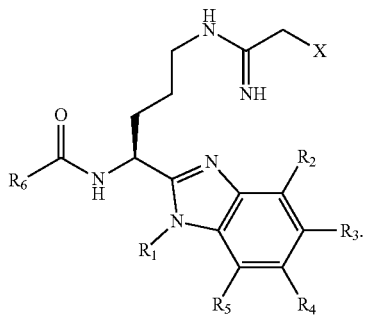

5. The compound of claim 1, wherein $R_1$ is a $C_{1-6}$ alkyl group or H.

6. The compound of claim 1, wherein one of $R_2$ and $R_3$ is a group selected from the group consisting of hydroxyl, F, Cl, $C_{1-6}$ alkyl, $C_{1-6}$ alkoxy, alkynyl, $CF_2R_c$, and $OCF_2R_c$ groups, where $R_c$ is H, F or alkyl.

7. The compound of claim 1, wherein $R_6$ is selected from the group consisting of:

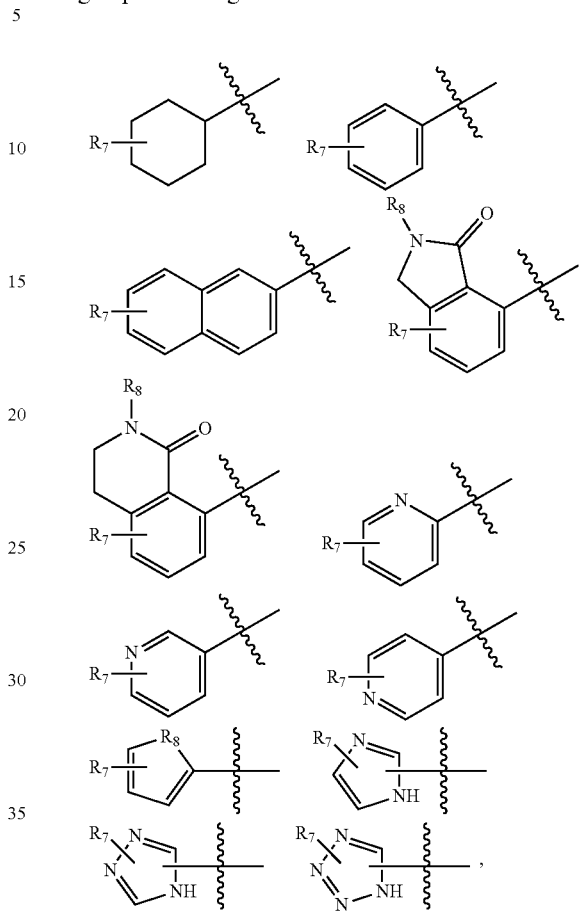

wherein
$R_7$ is independently selected from the group consisting of H, $C_{1-6}$ alkyl, $C_{1-6}$ alkoxy, hydroxyl, halogen atoms, aryl, —$COOR_8$, ethynyl, alkynyl, $CF_2R_c$, and $OCF_2R_c$, where $R_c$ is H, F or alkyl;
$R_8$ is independently selected from the group consisting of H and $C_{1-6}$ alkyl; and
$R_9$ is $CH_2$, O, $NH_2$ or S.

8. The compound of claim 7, wherein $R_7$ is H.

9. The compound of claim 7, wherein $R_8$ is a $C_{1-6}$ alkyl group.

10. A pharmaceutical composition comprising a compound of claim 1, and a pharmaceutically acceptable excipient, carrier, or diluent.

11. A unit dosage form comprising a pharmaceutical composition according to claim 1.

12. A method for treating or reducing a disease or disorder, comprising administering to a subject in need thereof an effective amount of a pharmaceutical composition comprising a compound of claim 1 and a pharmaceutically acceptable excipient, carrier, or diluent, wherein the diseases or disorder is selected from the group consisting of cancer.

13. A method for inhibiting or inactivating a protein arginine deiminase, comprising administering to a subject in need thereof a pharmaceutical composition comprising a compound of claim 1 and a pharmaceutically acceptable excipient, carrier, or diluent, effective to inhibit or inactivate a biological function of a protein arginine deiminase, in a mammal, including a human.

14. The method of claim 13, wherein the protein arginine deiminase is selected from the group consisting of: PAD1, PAD2, PAD3 and PAD4.

15. A compound having the structural formula (I),

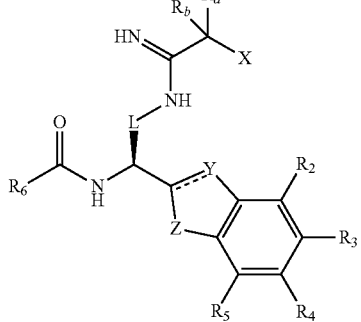
(I)

wherein
each of $R_a$ and $R_b$ is independently selected from the group consisting of H, D and F;
L is a bivalent hydrocarbyl linker, optionally with one or more carbon atoms replaced by a heteroatom selected from the group consisting of O, S and N;
X is a halogen atom;
Y is N, O or S; provided that when Y is S or O, its bonding to the adjacent carbons are single bonds;
Z is N—$R_1$, O or S;
$R_1$ is selected from the group consisting of: H, a $C_{1-6}$ alkyl, OH, a $C_{1-3}$ alkoxy, $CF_3$, $COCH_3$, or $COCF_3$ groups;
each of $R_2$, $R_3$, $R_4$ and $R_5$ is independently selected from the group consisting of: H, hydroxyl, halogen atom, $C_{1-6}$ alkyl, $C_{1-6}$ alkoxy, alkynyl, $CF_2R_c$, or $OCF_2R_c$ groups, where $R_c$ is H, F or alkyl; and
$R_6$ is a group selected from the group consisting of:

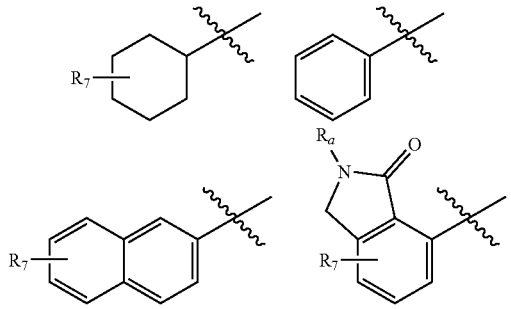

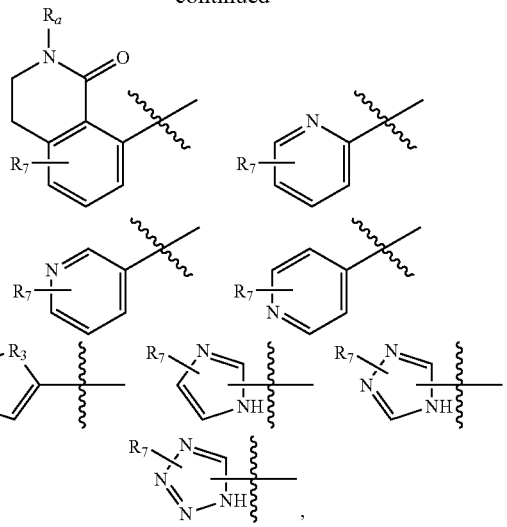

wherein
$R_7$ is independently selected from the group consisting of H, $C_{1-6}$ alkyl, $C_{1-6}$ alkoxy, hydroxyl, halogen atoms, aryl, —$COOR_8$, ethynyl, alkynyl, $CF_2R_c$, and $OCF_2R_c$, where $R_c$ is H, F or alkyl;
$R_8$ is independently selected from the group consisting of H and $C_{1-6}$ alkyl; and
$R_9$ is $CH_2$, O, $NH_2$ or S,
or a pharmaceutically acceptable form thereof.

16. The compound of claim 15, wherein each of $R_a$ and $R_b$ is H.

17. The compound of claim 15, wherein L is a —$(CH_2)_{n-}$, wherein n is an integer from 1 to about 4.

18. The compound of claim 15, wherein Y is N and Z is N-$R_1$ with the compound having the structural formula (II):

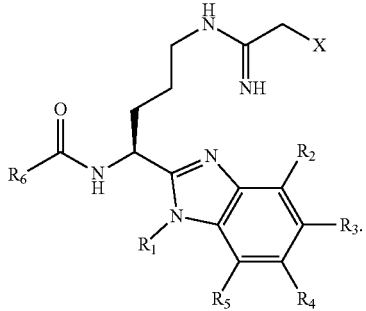

19. The compound of claim 15, wherein $R_7$ is H.
20. The compound of claim 15, wherein $R_8$ is a $C_{1-6}$ alkyl group.

* * * * *